United States Patent
Forman et al.

(10) Patent No.: US 10,611,729 B2
(45) Date of Patent: Apr. 7, 2020

(54) FARNESOID X RECEPTOR ANTAGONISTS

(71) Applicant: City of Hope, Duarte, CA (US)

(72) Inventors: Barry Forman, Irvine, CA (US); Donna Yu, Arcadia, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/926,564

(22) Filed: Mar. 20, 2018

(65) Prior Publication Data
US 2018/0334437 A1 Nov. 22, 2018

Related U.S. Application Data

(60) Division of application No. 15/214,282, filed on Jul. 19, 2016, now Pat. No. 9,944,605, which is a continuation of application No. PCT/US2015/013596, filed on Jan. 29, 2015.

(60) Provisional application No. 61/933,095, filed on Jan. 29, 2014.

(51) Int. Cl.
*C07D 231/14* (2006.01)
*C07D 231/12* (2006.01)

(52) U.S. Cl.
CPC ......... *C07D 231/14* (2013.01); *C07D 231/12* (2013.01)

(58) Field of Classification Search
CPC ............................ C07D 231/12; C07D 231/14
See application file for complete search history.

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 7,405,230 B2 | 7/2008 | Schumacher et al. |
| 9,944,605 B2 | 4/2018 | Foreman et al. |
| 2008/0300260 A1 | 12/2008 | Geneste et al. |

FOREIGN PATENT DOCUMENTS

WO WO-2007/052843 A1 5/2007

OTHER PUBLICATIONS

Nakamura, I. et al. Transition-Metal-Catalyzed Reactions in Heterocyclic Synthesis. Chem. Rev. 2004, vol. 104, p. 2127.*
Anderson (Chem and Biol 10:787-797, 2003).*
Thiel (Nature Biotechnol 2:513-519, 2004).*
Akwabi-Ameyaw, A. et al. (Oct. 15, 2011, e-published Aug. 11, 2011). "Conformationally constrained farnesoid X receptor (FXR) agonists: alternative replacements of the stilbene," *Bioorg. Med. Chem. Lett.* 21(20):6154-6160.
Anderson, A.C. (Sep. 2003). "The Process of Structure Based Drug Design," *Chemistry & Biology* 10:787-797.

(Continued)

*Primary Examiner* — Savitha M Rao
(74) *Attorney, Agent, or Firm* — Mintz Levin; Irina Britva; Kenneth Jenkins

(57) ABSTRACT

Provided herein are Farnesoid X receptor (FXR) antagonists having the structure of formula (I), and pharmaceutical compositions comprising the compound of formula (I) and a pharmaceutically acceptable excipient. Also provided are methods of antagonizing FXR, and methods of treating metabolic disease in a subject in need thereof, comprising administering an effective amount of the FXR antagonists of formula (I) to a subject.

10 Claims, 8 Drawing Sheets

Compound: 4j

FXR: $IC_{50}$ = 7.5 nM

(56) References Cited

OTHER PUBLICATIONS

Babaoglu, K. et al. (Dec. 2006, e-published Oct. 29, 2006). "Deconstructing fragment-based inhibitor discovery," *Nat. Chem. Biol.* 2(12):720-723.
Baraldi, P. G. et al. (Jul. 28, 2005). "New 2-arylpyrazolo[4,3-c]quinoline derivatives as potent and selective human A3 adenosine receptor antagonists," *J. Med. Chem.* 48(15):5001-5008.
Bebernitz, G. R. et al. (Aug. 2, 2001). "The effect of 1,3-diaryl-[1H]-pyrazole-4-acetamides on glucose utilization in ob/ob mice," *J. Med. Chem.* 44(16):2601-2611.
Chen, W.D et al. (Mar. 2010). "Farnesoid X receptor alleviates age-related proliferation defects in regenerating mouse livers by activating forkhead box m1b transcription," *Hepatology* 51(3):953-962.
Di Leva, F. S. et al. (Jun. 13, 2013, e-published May 24, 2013). "Binding mechanism of the farnesoid X receptor marine antagonist suvanine reveals a strategy to forestall drug modulation on nuclear receptors. Design, synthesis, and biological evaluation of novel ligands," *J. Med. Chem.* 56:(11):4701-4717.
Dussault, I. et al. (Feb. 28, 2003, e-published Dec. 19, 2002). "Identification of gene-selective modulators of the bile acid receptor FXR," *J. Biol. Chem.* 278(9):7027-7033.
Fiorucci, S. et al. (Apr. 2010, e-published Dec. 2, 2009). "Bile acidactivated receptors in the treatment of dyslipidemia and related disorders," *Prog. Lipid Res.* 49(2):171-185.
Fiorucci, S. et al. (2010). "Targetting farnesoid-X-receptor: from medicinal chemistry to disease treatment," *Curr. Med. Chem.* 17(2):139-159.
Fiorucci, S. et al. (2012). "Development of FXR, PXR and CAR agonists and antagonists for treatment of liver disorders," *Curr Top Med Chem.* 12(6):605-624.
Fiorucci, S. et al. (May 2009). "Farnesoid X receptor agonists in biliary tract disease," *Curr. Opin. Gastroenterol* 25(3):252-259.
Forman, B. M. et al. (Jun. 1995). "Identification of a nuclear receptor that is activated by farnesol metabolites," *Cell* 81(5): 687-693.
Hashimoto, Y. (Apr. 1991). "Retinobenzoic acids and nuclear retinoic acid receptors," *Cell Struct. Funct.* 16(2):113-123.
Huang, H. et al. (Aug. 23, 2012, e-published Aug. 10, 2012). "Discovery and optimization of 1,3,4-trisubstituted-pyrazolone derivatives as novel, potent, and nonsteroidal farnesoid X receptor (FXR) selective antagonists," *J. Med. Chem.* 55(16):7037-7053.
International Search Report dated Jul. 20, 2015, for PCT Application No. PCT/US2015/013596, filed on Jan. 29, 2015, 5 pages.
Lamberth, C. (2007). "Pyrazole chemistry in crop protection," *Heterocycles* 71:1467.
Lepore, S. D. et al. (Oct. 17, 2003). "Use of sonication for the coupling of sterically hindered substrates in the phenolic Mitsunobu reaction," *J. Org. Chem.* 68(21):8261-8263.
Li, G. et al. (Jan. 15, 2012, e-published Dec. 4, 2011). "A tea catechin, epigallocatechin-3-gallate, is a unique modulator of the farnesoid X receptor," *Toxicol Appl Pharmacol.* 258(2): 268-274.
Makishima, M. et al. (May 21, 1999). "Identification of a nuclear receptor for bile acids," *Science* 284(5418):1362-1365.
Modica, S. et al (Oct. 9, 2006, e-published Aug. 8, 2006). "Nuclear bile acid receptor FXR as pharmacological target: are we there yet?" *FEBS Lett.* 580(23):5492-5499.

Nakamura, I. et al. (May 2004). "Transition-metal-catalyzed reactions in heterocyclic synthesis," *Chem Rev* 104(5):2127-2198.
Nam, S.J. et al. (Oct. 15, 2006, e-published Aug. 14, 2006). "Farnesoid X-activated receptor antagonists from a marine sponge *Spongia* sp," *Bioorg. Med. Chem. Lett.* 16(20):5398-5402.
Ozers, M. S. et al. (Jan. 23, 2007). "The androgen receptor T877A mutant recruits LXXLL and FXXLF peptides differently than wild-type androgen receptor in a time-resolved fluorescence resonance energy transfer assay," *Biochemistry* 46(3): 683-695.
Pellicciari, R. et al. (Aug. 25, 2005). "Farnesoid X receptor: from structure to potential clinical applications," *J. Med. Chem.* 48(17):5383-5403.
Petzinger, E. et al. (Nov. 1999). "Hepatobiliary transport of bile acid amino acid, bile acid peptide, and bile acid oligonucleotide conjugates in rats," *Hepatology* 30(5):1257-1268.
PubChem CID-16277427, created Jul. 30, 2007, located at <https://pubchem.ncbi.nlm.nih.gov/compound/16277427>, last visited Jun. 20, 2017, 11 pages.
PubChem CID-65197318, created Oct. 23, 2012, located at <https://pubchem.ncbi.nlm.nih.gov/compound/65197318>, last visited Jun. 20, 2017, 10 pages.
Renga, B. et al. (Mar. 2011, e-published Feb. 4, 2011). "Farnesoid X receptor suppresses constitutive androstane receptor activity at the multidrug resistance protein-4 promoter," *Biochim. Biophys. Acta* 1809(3):157-165.
Rengal, B. et al. (2012). "Discovery that theonellasterol a marine sponge sterol is a highly selective FXR antagonist that protects against liver injury in cholestasis," *PLoS ONE* 7, e30443.
Sayin, S. I. et al. (Feb. 5, 2013). "Gut microbiota regulates bile acid metabolism by reducing the levels of tauro-beta-muricholic acid, a naturally occurring FXR antagonist," *Cell Metabolism* 17(2):225-235.
Sepe, V. et al. (Mar. 10, 2011, e-published Feb. 10, 2011). "Discovery of sulfated sterols from marine invertebrates as a new class of marine natural antagonists of farnesoid-X-receptor," *J Med Chem* 54(5):1314-1320.
Soisson, S. M. et al. (Apr. 8, 2008). "Identification of a potent synthetic FXR agonist with an unexpected mode of binding and activation," *Proc Natl Acad Sci U S A.* 105(14): 5337-5342.
Thiel, K.A. (May 2004). "Structure-aided drug design's next generation," *Nature Biotechnology* 22(5):513-519.
Urizar, N. L. et al. (May 31, 2002, e-published May 2, 2002). "A natural product that lowers cholesterol as an antagonist ligand for FXR," *Science* 296(5573):1703-1706.
Urizar, N. L. et al. (2003). "GUGULIPID: a natural cholesterol-lowering agent," *Annu. Rev.Nutr.* 23:303-313.
Wang, H. et al. (May 1999). "Endogenous bile acids are ligands for the nuclear receptor FXR/BAR," *Mol. Cell* 3(5):543-553.
Written Opinion dated Jul. 20, 2015, for PCT Application No. PCT/US2015/013596, filed on Jan. 29, 2015, 5 pages.
Yu, D. et al. (Nov. 2012, e-published Sep. 21, 2012). "An improved synthesis of 6α-ethylchenodeoxycholic acid (6ECDCA), a potent and selective agonist for the Farnesoid X Receptor (FXR)," *Steroids* 77(13):1335-1338.
Yu, D. et al. (Jul. 15, 2013). "Development of Time Resolved Fluorescence Resonance Energy Transfer-based Assay for FXR Antagonist Discovery," *Bioorganic & Medicinal Chemistry* 21(14):4266-4278.

\* cited by examiner

Compound: 4j
FXR: IC$_{50}$ = 7.5 nM 1,3,4-trisubstituted pyrazole
carboxamides

F1

F2

FARNESOID X RECEPTOR ANTAGONISTS

CROSS-REFERENCES TO RELATED APPLICATIONS

This application is a division application of U.S. patent application Ser. No. 15/214,282, filed Jul. 19, 2016, which is a continuation application of PCT Application No. PCT/US2015/013596, filed Jan. 29, 2015, which claims the benefit of U.S. Provisional Patent Application No. 61/933,095, filed Jan. 29, 2014, all of which are incorporated herein by reference in their entireties and for all purposes.

BACKGROUND OF THE INVENTION

Farnesoid X receptor (FXR, NRIH4),[1] a member of the bile acid nuclear hormone receptor superfamily, is a ligand-dependent transcription factor that regulates gene networks involved in regulating lipid and cholesterol homeostasis.[2] FXR is expressed primarily in tissues exposed to high concentrations of bile acids, such as the intestine, kidney, adrenal gland, and liver.[3] Consistent with the role of FXR, bile acids are the primary activating endogenous ligands of FXR.[3-4] As the bile acid sensor, FXR regulates the expression of transporters and biosynthetic enzymes crucial for the physiological maintenance of bile acid homeostasis.

BRIEF SUMMARY OF THE INVENTION

In a first aspect is a compound of formula (I):

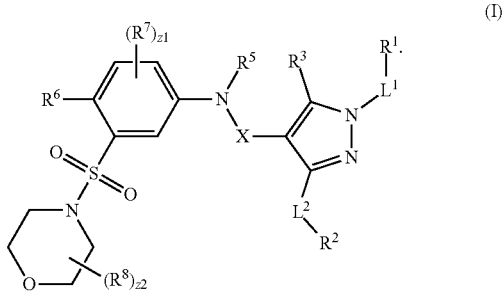

(I)

In formula (I), X is —$CH_2$— or —C(O)— or —CY(OH)—. Y is hydrogen, halogen, —$N_3$, —$NO_2$, —$CF_3$, —$CCl_3$, —$CBr_3$, —$CI_3$, —CN, —$OR^{9A}$, —$NHR^{9A}$, —$COOR^{9A}$, —$CONHR^{9A}$, —SH, —$SO_3H$, —$SO_4H$, —$SO_2NH_2$, —$NHNH_2$, —$ONH_2$, —$OCH_3$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^1$ is independently a bond, —C(O)—, —O—, —S—, —$NR^{9B}$—, —C(O)$NR^{9B}$—, —S(O)$_n$—, —S(O)$NR^{9B}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ is independently a bond, —C(O)—, —O—, —S—, —$NR^{9C}$—, —C(O)$NR^{9C}$—, —S(O)$_n$—, —S(O)$NR^{9C}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ and $R^2$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$, —$COOR^{3A}$, —C(O)$NR^{3B}R^{3C}$, —$NO_2$, —$SR^{3D}$, —S(O)$_{n3}R^{3B}$, —S(O)$_{n3}OR^{3B}$, —S(O)$_{n3}NR^{3B}R^{3C}$, —$NHNR^{3B}R^{3C}$, —$ONR^{3B}R^{3C}$, —NHC(O)$NHNR^{3B}R^{3C}$, or substituted or unsubstituted alkyl. $R^5$ is hydrogen or substituted or unsubstituted alkyl. $R^6$ is halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{n6}OR^{6B}$, —$SO_{n6}NR^{6B}R^{6C}$, —$NHNR^{6B}R^{6C}$, —$ONR^{6B}R^{6C}$, —NHC(O)$NHNR^{6B}R^{6C}$, substituted or unsubstituted alkyl, or substituted or unsubstituted heteroalkyl. $R^7$ is independently hydrogen, halogen, —$N_3$, —$CF_3$, —$CCl_3$, —$CBr_3$, —$CI_3$, —CN, —CHO, —$OR^{7A}$, —$NR^{7B}R^{7C}$, —$COOR^{7A}$, —C(O)$NR^{7B}R^{7C}$, —$NO_2$, —$SR^{7D}$, —S(O)$_{n7}R^{7B}$, —S(O)$_{n7}OR^{7B}$, —S(O)$_{n7}NR^{7B}R^{7C}$, —$NHNR^{7B}R^{7C}$, —$ONR^{7B}R^{7D}$, —NHC(O)$NHNR^{7B}R^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^8$ is independently hydrogen, halogen, —$N_3$, —$CF_3$, —$CCl_3$, —$CBr_3$, —$CI_3$, —CN, —CHO, —$OR^{8A}$, —$NR^{8B}R^{8C}$, —$COOR^{8A}$, —C(O)$NR^{8B}R^{8C}$, —$NO_2$, —$SR^{8D}$, —S(O)$_{n8}R^{8B}$, —S(O)$_{n8}OR^{8B}$, —S(O)$_{n8}NR^{8B}R^{8C}$, —$NHNR^{8B}R^{8C}$, —$ONR^{8B}R^{8C}$, —NHC(O)$NHNR^{8B}R^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{9A}$, $R^{9B}$, $R^{9C}$ are independently hydrogen, halogen, —$N_3$, —$NO_2$, —$CF_3$, —$CCl_3$, —$CBr_3$, —$CI_3$, —CN, —OH, —$NH_2$, —COOH, —$CONH_2$, —SH, —$SO_3H$, —$SO_4H$, —$SO_2NH_2$, —$NHNH_2$, —$ONH_2$, —$OCH_3$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3A}$, $R^{6A}$, $R^{7A}$, and $R^{8A}$ are independently hydrogen or unsubstituted alkyl. $R^{3B}$, $R^{6B}$, $R^{7B}$, $R^{8B}R^{3C}$, $R^{6C}$, $R^{7C}$, $R^{8C}$, $R^{3D}$, $R^{6D}$, $R^{7D}$, and $R^{8D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol z1 is 1, 2, 3, 4, 5 or 6. The symbol z2 is 1, 2, 3, 4, 5, 6, 7 or 8. The symbols n, n3, n6, n7, and n8 are independently 1 or 2. In embodiments, if X is —C(O)— and -$L^1$-$R^1$ is unsubstituted phenyl, then -$L^2$-$R^2$ is not methyl, p-substituted or unsubstituted phenyl, or unsubstituted pyridine.

In another aspect a pharmaceutical composition is provided. The pharmaceutical composition includes a pharmaceutically acceptable excipient and a compound having formula:

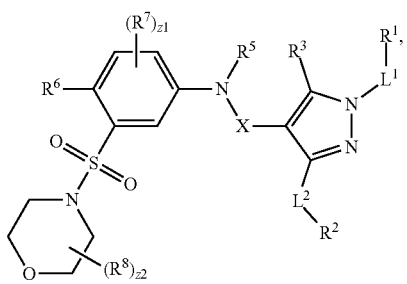

(I)

X is —C($R^{4A}$)($R^{4B}$)—, —C(O)—, —CY(OH)—. Y is hydrogen, halogen, —$N_3$, —$NO_2$, —$CF_3$, —$CCl_3$, —$CBr_3$, —$CI_3$, —CN, —$OR^{9A}$, —$NHR^{9A}$, —$COOR^{9A}$, —$CONHR^{9A}$, —SH, —$SO_3H$, —$SO_4H$, —$SO_2NH_2$, —$NHNH_2$, —$ONH_2$, —$OCH_3$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^1$ is independently a bond, —C(O)—, —O—, —S—, —$NR^{9B}$—, —C(O)$NR^{9B}$—, —S(O)$_n$—, —S(O)$NR^{9B}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ are independently a bond, —C(O)—, —O—, —S—, —$NR^{9C}$—, —C(O)$NR^{9C}$—, —S(O)$_n$—, —S(O)$NR^{9C}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$, $R^2$, $R^3$, $R^{4A}$, $R^{4B}$, $R^5$, $R^6$, $R^7$, and $R^8$ are independently hydrogen, halogen, —$N_3$, —$CF_3$, —$CCl_3$, —$CBr_3$, —$CI_3$, —CN, —CHO, —$OR^{11A}$, —$NR^{11B}R^{11C}$, —$COOR^{11A}$, —C(O)$NR^{11B}R^{11C}$, —$NO_2$, —$SR^{11D}$, —S(O)$_{n11}R^{11B}$, —S(O)$_{n11}OR^{11B}$, —S(O)$_{n11}NR^{11B}R^{11C}$, —$NHNR^{11B}R^{11C}$, —$ONR^{11B}R^{11C}$, —NHC(O)$NHNR^{11B}R^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{9A}$, $R^{9B}$, $R^{9C}$ are independently hydrogen, halogen, —$N_3$, —$NO_2$, —$CF_3$, —$CCl_3$, —$CBr_3$, —$CI_3$, —CN, —OH, —$NH_2$, —COOH, —$CONH_2$, —SH, —$SO_3H$, —$SO_4H$, —$SO_2NH_2$, —$NHNH_2$, —$ONH_2$, —$OCH_3$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n and n11 are independently 1 or 2. The symbol z1 is 1, 2, 3, 4, 5, or 6. The symbol z2 is 1, 2, 3, 4, 5, 6, 7, or 8. $R^{11A}$, $R^{11B}$, $R^{11C}$, and $R^{11D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The pharmaceutical compositions contemplated herein include pharmaceutically acceptable salts thereof, as described herein, including embodiments thereof.

In another aspect is a method of treating metabolic disease in a subject in need thereof. The method includes administering to the subject in need thereof, a compound of formula (I), (II), or (III), including embodiments thereof.

In another aspect is provided a method of antagonizing an FXR receptor protein. The method includes contacting an FXR receptor protein with a compound disclosed herein (e.g. formula (I), (II), or (III)), thereby antagonizing the FXR receptor protein.

DETAILED DESCRIPTION OF THE INVENTION

Figure 1:
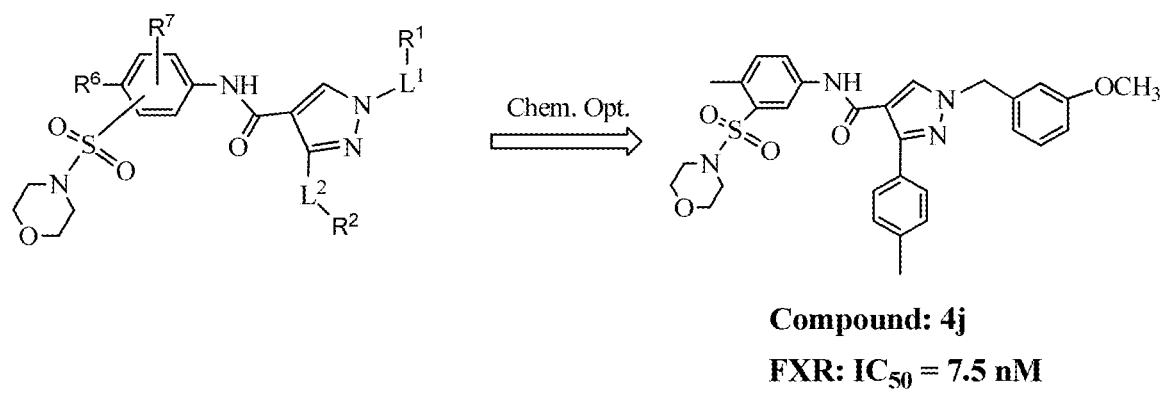
FIG. 1: Chemical structures of compounds synthesized herein.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—OCH$_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—OCH$_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "thio," as used herein, means a sulfur that is single bonded to carbon or to another sulfur.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, —NR'SO$_2$R", —NR'C=(O)R", —NR'C(O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C=(O)R", —NR'C(O)—OR", —NR'OR", in a number ranging from zero to the total number of open valences on the aromatic ring system; and where R, R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein include those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

A "therapeutically effective amount" or "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

"Patient," "subject," "patient in need thereof," and "subject in need thereof" are herein used interchangeabley and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., *Gao Pharm. Res.* 12:857-863, 1995); or, as microspheres for oral administration (see, e.g., Eyles, *J Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

The term "associated" or "associated with" in the context of a substance or substance activity or function associated with a disease means that the disease is caused by (in whole or in part), a symptom of the disease is caused by (in whole or inpart) the substance or substance activity or function, or a side-effect of the compound (e.g. toxicity) is caused by (in whole or inpart) the substance or substance activity or function.

The term "metabolic syndrome" as used herein refers to a group of conditions including, but not limited to, dyslipidemia (e.g. hyperlipidemia), insulin-resistance, increased blood pressure, visceral obesity and hypercoagubility, where at least two of the conditions occur simultaneously. The term "cholestasis" refers to a condition characterized by elevated levels of bile acid in the liver. The term "hypertriglyceridemia" refers to a condition characterized by elevated levels of triglycerides in the blood.

Farnesoid X Receptor or "FXR" refers to a nuclear hormone receptor found in the liver, intestines, adrenal glands, and kidneys. FXR is involved in regulation of lipid and carbohydrate metabolism and trigyceride homeostasis. FXR also regulates bile acid synthesis (e.g. through induced expression of small heterodimer partner (SHP) protein).

An "agonist," as used herein, refers to a compound capable of detectably increasing the expression or activity of a given protein or receptor. The agonist can increase expression or activity 10%, 20%, 30%, 40%, 50%, 60%, 70%, 80%, 90%, 100% or more in comparison to a control in the absence of the agonist. In embodiments, expression or activity is 1.5-fold, 2-fold, 3-fold, 4-fold, 5-fold, 10-fold or more higher than the expression or activity in the absence of the agonist. An "FXR agonist" is a compound which increases FXR activity. In embodiments, the increased FXR activity indirectly represses synthesis of bile acid. In embodiments the increased FXR activity reduces triglyceride levels in hypertriglyceridemic subjects.

The term "antagonist" refers to a substance capable of detectably lowering expression or activity of a given protein. The antagonist can inhibit expression or activity 10%, 20%, 30%, 40%, 50%, 60%, 70%, 80%, 90%, 100% or less in comparison to a control in the absence of the antagonist. In embodiments, the inhibition is 1.5-fold, 2-fold, 3-fold, 4-fold, 5-fold, 10-fold, or more than the expression or activity in the absence of the antagonist. An "FXR antagonist" is a compound which decreases FXR activity. In embodiments, decreased FXR activity increases conversion of cholesterol to bile acids. The increased conversion may decrease low density lipoprotein (LDL) levels in hyperlipidemic subjects. In embodiments decreased FXR activity reduces the amount of bile acid returning to the liver In a first aspect is a compound of formula (I):

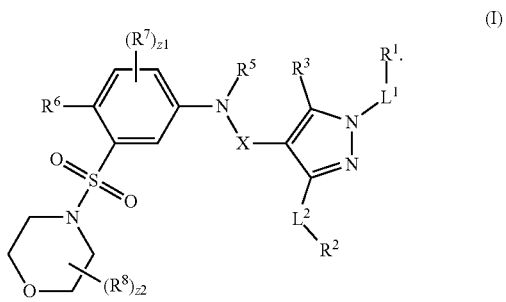

In formula (I), X is —CH$_2$— or —C(O)— or —CY(OH)—. Y is hydrogen, halogen, —N$_3$, —NO$_2$, —CF$_3$, —CCl$_3$, —CBr$_3$, —CI$_3$, —CN, —OR$^{9A}$, —NHR$^{9A}$, —COOR$^{9A}$, —CONHR$^{9A}$, —SH, —SO$_3$H, —SO$_4$H, —SO$_2$NH$_2$, —NHNH$_2$, —ONH$_2$, —OCH$_3$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^1$ is independently a bond, —C(O)—, —C(O)O—, —O—, —S—, —$NR^{9B}$—, —C(O)$NR^{9B}$—, —S(O)$_n$—, —S(O)$NR^{9B}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ is independently a bond, —C(O)—, —C(O)O—, —O—, —S—, —$NR^{9C}$—, —C(O)$NR^{9C}$—, —S(O)$_n$—, —S(O)$NR^{9C}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ and $R^2$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$, —$COOR^{3A}$, —C(O)$NR^{3B}R^{3C}$, —$NO_2$, —$SR^{3D}$, —S(O)$_{n3}R^{3B}$, —S(O)$_{n3}OR^{3B}$, —S(O)$_{n3}NR^{3B}R^{3C}$, —$NHNR^{3B}R^{3C}$, —$ONR^{3B}R^{3C}$, —NHC(O)$NHNR^{3B}R^{3C}$, or substituted or unsubstituted alkyl. $R^5$ is hydrogen or substituted or unsubstituted alkyl. $R^6$ is halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{n6}OR^{6B}$, —$SO_{n6}NR^{6B}R^{6C}$, —$NHNR^{6B}R^{6C}$, —$ONR^{6B}R^{6C}$, —NHC(O)$NHNR^{6B}R^{6C}$, substituted or unsubstituted alkyl, or substituted or unsubstituted heteroalkyl. $R^7$ is independently hydrogen, halogen, —$N_3$, —$CF_3$, —$CCl_3$, —$CBr_3$, —$CI_3$, —CN, —CHO, —$OR^{7A}$, —$NR^{7B}R^{7C}$, —$COOR^{7A}$, —C(O)$NR^{7B}R^{7C}$, —$NO_2$, —$SR^{7D}$, —S(O)$_{n7}R^{7B}$, —S(O)$_{n7}OR^{7B}$, —S(O)$_{n7}NR^{7B}R^{7C}$, —$NHNR^{7B}R^{7C}$, —$ONR^{7B}R^{7D}$, —NHC(O)$NHNR^{7B}R^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^8$ is independently hydrogen, halogen, —$N_3$, —$CF_3$, —$CCl_3$, —$CBr_3$, —$CI_3$, —CN, —CHO, —$OR^{8A}$, —$NR^{8B}R^{8C}$, —$COOR^{8A}$, C(O)$NRBR^{8C}$, —$NO_2$, —$SR^{8D}$, —S(O)$_{n8}R^{8B}$, —S(O)$_{n8}OR^{8B}$, —S(O)$_{n8}NR^{8B}R^{8C}$, —$NHNR^{8B}R^{8C}$, —$ONR^{8B}R^{8C}$, —NHC(O)$NHNR^{8B}R^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{9A}$, $R^{9B}$, and $R^{9C}$ are independently hydrogen, halogen, —$N_3$, —$NO_2$, —$CF_3$, —$CCl_3$, —$CBr_3$, —$CI_3$, —CN, —OH, —$NH_2$, —COOH, —$CONH_2$, —SH, —$SO_3H$, —$SO_4H$, —$SO_2NH_2$, —$NHNH_2$, —$ONH_2$, —$OCH_3$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3A}$, $R^{6A}$, $R^{7A}$, and $R^{8A}$ are independently hydrogen or substituted alkyl. $R^{3B}$, $R^{6B}$, $R^{7B}$, $R^{8B}$, $R^{3C}$, $R^{6C}$, $R^{7C}$, $R^{8C}$, $R^{3D}$, $R^{6D}R^{7D}$, and $R^{8D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol z1 is 1, 2, 3, 4, 5 or 6. The symbol z2 is 1, 2, 3, 4, 5, 6, 7 or 8. The symbols n, n3, n6, n7, and n8 are independently 1 or 2. In embodiments, if X is —C(O)— and -$L^1$-$R^1$ is unsubstituted phenyl, then -$L^2$-$R^2$ is not methyl, p-substituted or unsubstituted phenyl, or unsubstituted pyridine.

X may be —$CH_2$—. X may be —C(O)—. X may be —CY(OH)—. In embodiments, Y is hydrogen or substituted or unsubstituted alkyl. Y may be hydrogen (e.g. X is —C(H)OH—). Y may be substituted or unsubstituted $C_1$-$C_{10}$ alkyl. Y may be substituted or unsubstituted $C_1$-$C_{10}$ alkyl. In embodiments, Y is methyl. In embodiments, Y is halogen, —$N_3$, —$NO_2$, —$CF_3$, —$CCl_3$, —$CBr_3$, —$CI_3$, —CN, —$OR^{9A}$, —$NHR^{9A}$, —$COOR^{9A}$, —$CONHR^{9A}$, —SH, —$SO_3H$, —$SO_4H$, —$SO_2NH_2$, —$NHNH_2$, —$ONH_2$, —$OCH_3$, —NHC(O)$NHNH_2$. Y may be halogen, —$N_3$, —$NO_2$, —$CF_3$, —$CCl_3$, —$CBr_3$, —$CI_3$, —CN, —$OR^9A$ —$NHR^{9A}$, —COOH, or —$CONH_2$. Y may be halogen, —$OR^{9A}$, —$NHR^{9A}$, —$COOR^{9A}$, —$CONHR^{9A}$. $R^{9A}$ may be hydrogen or $C_1$-$C_5$ substituted or unsubstituted alkyl (e.g. methyl). In embodiments, Y is substituted or unsubstituted heteroalkyl, substituted or unsubstituted cycloalkyl, substituted or unsubstituted heterocycloalkyl, substituted or unsubstituted aryl, or substituted or unsubstituted heteroaryl. Y may be substituted or unsubstituted heteroalkyl (e.g. 2 to 10 membered or 2 to 6 membered heteroalkyl). Y may be substituted or unsubstituted cycloalkyl (e.g. 3 to 10 membered or 3 to 6 membered cycloalkyl). Y may be substituted or unsubstituted heterocycloalkyl (e.g. 3 to 10 membered or 3 to 6 membered heterocycloalkyl). Y may be substituted or unsubstituted aryl (e.g. 6 membered aryl). Y may be substituted or unsubstituted heteroaryl (e.g. 5 or 6 membered heteroaryl).

$L^1$ may independently be a bond, —C(O)—, —O—, —S—, —$NR^{9B}$—, —C(O)$NR^9B$—, —S(O)$_n$—, —S(O)$NR^{9B}$-. $L^1$ may independently be a bond, —C(O)—, —O—. $L^1$ may independently be a bond, —C(O)—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^1$ may independently be a bond, —C(O)—, substituted or unsubstituted alkylene, substituted or unsubstituted heteroarylene, or substituted or unsubstituted arylene. $L^1$ may independently be a bond. $L^1$ may independently be substituted or unsubstituted alkylene (e.g. substituted or unsubstituted $C_1$ to $C_{10}$ alkyl). $L^1$ may independently be substituted or unsubstituted heteroarylene (e.g. substituted or unsubstituted 6 membered arylene). $L^1$ may independently be substituted or unsubstituted heteroarylene (e.g. substituted or unsubstituted 5 or 6 membered heteroarylene). In embodiments $L^1$ may independently be substituted or unsubstituted fused ring arylene or substituted or unsubstituted fused ring heteroaryl. $L^1$ may independently be a bond. $L^2$ may independently be a bond, —C(O)—, —O—, —S—, —$NR^{9C}$—, —C(O)$NR^{9C}$—, —S(O)$_n$—, —S(O)$NR^{9C}$-. $L^2$ may independently be a bond, —C(O)—, —O—. $L^2$ may independently be a bond, —C(O)—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ may independently be a bond, —C(O)—, substituted or unsubstituted alkylene, substituted or unsubstituted heteroarylene, or substituted or unsubstituted arylene. $L^2$ may independently be a bond. $L^2$ may independently be substituted or unsubstituted alkylene (e.g. substituted or unsubstituted $C_1$ to $C_{10}$ alkyl). $L^2$ may independently be substituted or unsubstituted heteroarylene (e.g. substituted or unsubstituted 6 membered arylene). $L^2$ may independently be substituted or unsubstituted heteroarylene (e.g. substituted or unsubstituted 5 or 6 membered heteroarylene). In embodiments $L^2$ may independently be substituted or unsubstituted fused ring arylene or substituted or unsubstituted fused ring heteroaryl. $L^2$ may independently be a bond. $L^1$ and $L^2$ may independently be a bond.

$L^1$ may independently be substituted or unsubstituted alkylene. $L^1$ may independently be substituted or unsubstituted $C_1$-$C_{10}$ alkylene. $L^1$ may independently be substituted or unsubstituted $C_1$-$C_5$ alkylene. $L^1$ may independently be $R^{12A}$-substituted or unsubstituted alkylene. $L^1$ may independently be $R^{12A}$-substituted or unsubstituted $C_1$-$C_{10}$ alkylene. $L^1$ may independently be $R^{12A}$-substituted or unsubstituted $C_1$-$C_5$ alkylene. $L^2$ may independently be substituted or unsubstituted alkylene. $L^2$ may independently be substituted or unsubstituted $C_1$-$C_{10}$ alkylene. $L^2$ may independently be substituted or unsubstituted $C_1$-$C_5$ alkylene. $L^2$ may independently be $R^{12B}$-substituted or unsubstituted alkylene. $L^2$ may independently be $R^{12B}$-substituted or unsubstituted $C_1$-$C_{10}$ alkylene. $L^2$ may independently be $R^{12B}$-substituted or unsubstituted $C_1$-$C_5$ alkylene.

$L^1$ may independently be substituted or unsubstituted heteroalkylene. $L^1$ may independently be substituted or unsubstituted 2 to 10 membered heteroalkylene. $L^1$ may independently be substituted or unsubstituted 2 to 6 membered heteroalkylene. $L^1$ may independently be $R^{12A}$-substituted or unsubstituted heteroalkylene. $L^1$ may independently be $R^{12A}$-substituted or unsubstituted 2 to 10 membered heteroalkylene. $L^1$ may independently be $R^{12A}$-substituted or unsubstituted 2 to 6 membered heteroalkylene. $L^2$ may independently be substituted or unsubstituted heteroalkylene. $L^2$ may independently be substituted or unsubstituted 2 to 10 membered heteroalkylene. $L^2$ may independently be substituted or unsubstituted 2 to 6 membered heteroalkylene. $L^2$ may independently be $R^{12B}$-substituted or unsubstituted heteroalkylene. $L^2$ may independently be $R^{12B}$-substituted or unsubstituted 2 to 10 membered heteroalkylene. $L^2$ may independently be $R^{12B}$-substituted or unsubstituted 2 to 6 membered heteroalkylene.

$L^1$ may independently be substituted or unsubstituted cycloalkylene. $L^1$ may independently be $R^{12A}$-substituted or unsubstituted cycloalkylene. $L^1$ may independently be substituted or unsubstituted heterocycloalkylene. $L^1$ may independently be $R^{12A}$-substituted or unsubstituted heterocycloalkylene. $L^1$ may independently be a substituted or unsubstituted arylene. $L^1$ may independently be a $R^{12A}$-substituted or unsubstituted arylene. $L^1$ may independently be a substituted or unsubstituted heteroarylene. $L^1$ may independently be a $R^{12A}$-substituted or unsubstituted heteroarylene. $L^2$ may independently be substituted or unsubstituted cycloalkylene. $L^2$ may independently be $R^{12B}$-substituted or unsubstituted cycloalkylene. $L^2$ may independently be substituted or unsubstituted heterocycloalkylene. $L^2$ may independently be $R^{12B}$-substituted or unsubstituted heterocycloalkylene. $L^2$ may independently be a substituted or unsubstituted arylene. $L^2$ may independently be a $R^{12B}$-substituted or unsubstituted arylene. $L^2$ may independently be a substituted or unsubstituted heteroarylene. $L^2$ may independently be a $R^{12B}$-substituted or unsubstituted heteroarylene.

In embodiments, X is —C(O)— and at least one of $L^1$ and $L^2$ is a bond. In embodiments, X is —C(O)— and $L^1$ and $L^2$ are a bond. X may be —C(O)— and $L^1$ may be a bond, substituted or unsubstituted alkylene, or substituted or unsubstituted heteroarylene. In embodiments, X is —C(O)—, $L^1$ is substituted or unsubstituted alkylene, and $L^2$ is a bond. In embodiments, X is —C(O)—, and $L^1$ and $L^2$ are substituted or unsubstituted alkylene. In embodiments, X is —CH$_2$—, and $L^1$ and $L^2$ are independently a bond or substituted or unsubstituted alkylene. In embodiments, X is —CH$_2$—, and $L^1$ and $L^2$ are independently a bond or substituted or unsubstituted alkylene. In embodiments, X is —CY(OH)—, and $L^1$ and $L^2$ are independently a bond or substituted or unsubstituted alkylene. In embodiments, X is —CY(OH)—, and $L^1$ and $L^2$ are independently a bond or substituted or unsubstituted alkylene.

$R^{12}$ is halogen, —N$_3$, —NO$_2$, —CF$_3$, —CCl$_3$, —CBr$_3$, —CI$_3$, —CN, —OH, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl. $R^{12}$ may be halogen, —CF$_3$, —OH, —COOH, or unsubstituted alkyl. $R^{12A}$ is halogen, —N$_3$, —NO$_2$, —CF$_3$, —CCl$_3$, —CBr$_3$, —CI$_3$, —CN, —OH, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl. $R^{12A}$ may be halogen, —CF$_3$, —OH, —COOH, or unsubstituted alkyl. $R^{12B}$ is halogen, —N$_3$, —NO$_2$, —CF$_3$, —CCl$_3$, —CBr$_3$, —CI$_3$, —CN, —OH, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl. $R^{12B}$ may be halogen, —CF$_3$, —OH, —COOH, or unsubstituted alkyl.

$R^1$ may be substituted or unsubstituted alkyl. $R^1$ may be unsubstituted alkyl. $R^1$ may be $R^{10}$-substituted or unsubstituted alkyl. $R^1$ may be substituted or unsubstituted alkyl. $R^1$ may be substituted or unsubstituted $C_1$-$C_{20}$ alkyl. $R^1$ may be $R^{10}$-substituted or unsubstituted $C_1$-$C_{20}$ alkyl. $R^1$ may be substituted or unsubstituted $C_1$-$C_{10}$ alkyl. $R^1$ may be $R^{10}$-substituted or unsubstituted $C_1$-$C_{10}$ alkyl. $R^1$ may be substituted or unsubstituted $C_1$-$C_5$ alkyl. $R^1$ may be $R^{10}$-substituted or unsubstituted $C_1$-$C_5$ alkyl. $R^1$ may be unsubstituted $C_1$-$C_3$ alkyl.

$R^1$ may be substituted or unsubstituted heteroalkyl. $R^1$ may be unsubstituted heteroalkyl. $R^1$ may be substituted or unsubstituted 2 to 20 membered heteroalkyl. $R^1$ may be $R^{10}$-substituted or unsubstituted 2 to 20 membered heteroalkyl. $R^1$ may be substituted or unsubstituted 2 to 10 membered heteroalkyl. $R^1$ may be $R^{10}$-substituted or unsubstituted 2 to 10 membered heteroalkyl. $R^1$ may be substituted or unsubstituted 2 to 6 membered heteroalkyl. $R^1$ may be $R^{10}$-substituted or unsubstituted 2 to 6 membered heteroalkyl.

$R^1$ may be substituted or unsubstituted cycloalkyl. $R^1$ may be unsubstituted cycloalkyl. $R^1$ may be $R^{10}$-substituted or unsubstituted 3 to 20 membered cycloalkyl. $R^1$ may be substituted or unsubstituted 3 to 20 membered cycloalkyl. $R^1$ may be substituted or unsubstituted 3 to 10 membered cycloalkyl. $R^1$ may be $R^{10}$-substituted or unsubstituted 3 to 10 membered cycloalkyl. $R^1$ may be substituted or unsubstituted 3 to 6 membered cycloalkyl. $R^1$ may be $R^{10}$-substituted or unsubstituted 3 to 6 membered cycloalkyl.

$R^1$ may be substituted or unsubstituted heterocycloalkyl. $R^1$ may be unsubstituted heterocycloalkyl. $R^1$ may be substituted or unsubstituted 3 to 20 membered heterocycloalkyl. $R^1$ may be $R^{10}$-substituted or unsubstituted 3 to 20 membered heterocycloalkyl. $R^1$ may be substituted or unsubstituted 3 to 10 membered heterocycloalkyl. $R^1$ may be $R^{10}$-substituted or unsubstituted 3 to 10 membered heterocycloalkyl. $R^1$ may be substituted or unsubstituted 3 to 6 membered heterocycloalkyl. $R^1$ may be $R^{10}$-substituted or unsubstituted 3 to 6 membered heterocycloalkyl.

$R^1$ may be substituted or unsubstituted aryl. $R^1$ may be unsubstituted aryl. $R^1$ may be substituted or unsubstituted 5 to 10 membered aryl. $R^1$ may be $R^{10}$-substituted or unsubstituted 5 to 10 membered aryl. $R^1$ may be substituted or unsubstituted 5 to 8 membered aryl. $R^1$ may be $R^{10}$-substituted or unsubstituted 5 to 8 membered aryl. $R^1$ may be substituted or unsubstituted 6 membered aryl. $R^1$ may be $R^{10}$-substituted or unsubstituted 6 membered aryl.

$R^1$ may be substituted or unsubstituted fused ring aryl (e.g. a 5,6-; 6,5-; or 6,6-fused ring aryl). $R^1$ may be $R^{10}$-substituted or unsubstituted fused ring aryl (e.g. a 5,6-; 6,5-; or 6,6-fused ring aryl). $R^1$ may be substituted or unsubstituted 5,6-fused ring aryl. $R^1$ may be $R^{10}$-substituted or unsubstituted 5,6-fused ring aryl. $R^1$ may be $R^{10}$-substituted or unsubstituted 6,5-fused ring aryl. $R^1$ may be $R^{10}$-substituted or unsubstituted 6,5-fused ring aryl. $R^1$ may be $R^{10}$-substituted or unsubstituted 6,6-fused ring aryl. $R^1$ may be $R^{10}$-substituted or unsubstituted 6,6-fused ring aryl.

$R^1$ may be substituted or unsubstituted heteroaryl. $R^1$ may be unsubstituted heteroaryl. $R^1$ may be substituted or unsubstituted 5 to 10 membered heteroaryl. $R^1$ may be $R^{10}$-substituted or unsubstituted 5 to 10 membered heteroaryl. $R^1$ may be substituted or unsubstituted 5 to 8 membered heteroaryl. $R^1$ may be $R^{10}$-substituted or unsubstituted 5 to 8 membered heteroaryl. $R^1$ may be substituted or unsubstituted 5 or 6 membered heteroaryl. $R^1$ may be $R^{10}$-substituted or unsubstituted 5 or 6 membered heteroaryl.

$R^1$ may be substituted or unsubstituted fused ring heteroaryl (e.g. a 5,6-; 6,5-; or 6,6-fused ring heteroaryl). $R^1$ may be $R^{10}$-substituted or unsubstituted fused ring heteroaryl (e.g. a 5,6-; 6,5-; or 6,6-fused ring heteroaryl). $R^1$ may be substituted or unsubstituted 5,6-fused ring heteroaryl. $R^1$ may be $R^{10}$-substituted or unsubstituted 5,6-fused ring heteroaryl. $R^1$ may be $R^{10}$-substituted or unsubstituted 6,5-fused ring heteroaryl. $R^1$ may be $R^{10}$-substituted or unsubstituted 6,5-fused ring heteroaryl. $R^1$ may be $R^{10}$-substituted or unsubstituted 6,6-fused ring heteroaryl. $R^1$ may be $R^{10}$-substituted or unsubstituted 6,6-fused ring heteroaryl.

$R^{10}$ is hydrogen, halogen, $-N_3$, $-CF_3$, $-CCl_3$, $-CBr_3$, $-CI_3$, $-CN$, $-CHO$, $-OR^{10A}$, $-NR^{10B}R^{10C}$, $-COOR^{10A}$, $-C(O)NR^{10B}R^{10C}$, $-NO_2$, $-SR^{10D}$, $-S(O)_{n10}R^{10B}$, $-S(O)_{n10}OR^{10B}$, $-S(O)_{n10}NR^{1B}R^{10C}$, $-NHNR^{10B}R^{10C}$, $-ONR^{10B}R^{10C}$, $-NHC(O)NHNR^{1B}R^{10C}$, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl. $R^{10}$ may be halogen, $-CF_3$, $-OR^{10A}$, $-NR^{10B}R^{10C}$, $-COOR^{10A}$, or $R^{13}$-substituted or unsubstituted alkyl. $R^{10}$ may be $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl.

$R^{10A}$, $R^{10B}$, $R^{11C}$, and $R^{10D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The symbol n10 is 1 or 2. $R^{10A}$, $R^{10B}$, $R^{11C}$, and $R^{10D}$ may independently be hydrogen or substituted or unsubstituted alkyl.

$R^{13}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{14}$-substituted or unsubstituted alkyl, $R^{14}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl, or $R^{14}$-substituted or unsubstituted heteroaryl. $R^{13}$ may be halogen, $-CF_3$, $-OH$, $-COOH$, or unsubstituted alkyl. $R^{13}$ may be $R^{14}$-substituted or unsubstituted alkyl, $R^{14}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl, or $R^{14}$-substituted or unsubstituted heteroaryl.

$R^{14}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl.

$R^{15}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl.

$R^{16}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{14}$-substituted or unsubstituted alkyl, unsubstituted heteroalkyl, unsubstituted cycloalkyl, unsubstituted heterocycloalkyl, unsubstituted aryl, or unsubstituted heteroaryl.

$R^1$ may be unsubstituted cycloalkyl, substituted or unsubstituted heterocycloalkyl, or substituted or unsubstituted aryl. In embodiments, $R^1$ is $R^{10}$-substituted or unsubstituted alkyl, $R^{10}$-substituted or unsubstituted cycloalkyl, or $R^{10}$-substituted or unsubstituted aryl. $R^{10}$ may independently be halogen, $-N_3$, $-CF_3$, $-CCl_3$, $-CBr_3$, $-CI_3$, $-CN$, $-CHO$, $-OR^{10A}$, $-NR^{10B}R^{10C}$, $-COOR^{10A}$, $-C(O)NR^{10B}R^{10C}$, $-NO_2$, $-SR^{10D}$, $-S(O)_{n10}R^{10B}$, $-S(O)_{n10}OR^{10B}$, $-S(O)_{n10}NR^{10B}R^{10C}$, $-NHNR^{10B}R^{10C}$, $-ONR^{10B}R^{10C}$, $-NHC(O)NHNR^{10B}R^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ may be halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ may be halogen, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl.

In embodiments, $R^1$ is $R^{10}$-substituted or unsubstituted alkyl, unsubstituted cycloalkyl, or $R^{10}$-substituted or unsubstituted aryl. $R^{10}$ may be halogen, $CF_3$, or $-OR^{10A}$. $R^{10}$ may be halogen. $R^{10}$ may be $CF_3$. $R^{10}$ may be $-OR^{10A}$. $R^{10A}$ may be hydrogen or unsubstituted $C_1$-$C_5$ alkyl (e.g. methyl or ethyl).

$R^{10A}$, $R^{10B}$, $R^{10C}$, and $R^{10D}$ may independently be hydrogen. $R^{10A}$, $R^{10B}$, $R^{10C}$, and $R^{10D}$ may independently be substituted or unsubstituted alkyl. $R^{10A}$, $R^{10B}$, $R^{10C}$, and $R^{10D}$ may independently be substituted or unsubstituted aryl. The symbol n10 may be 1. The symbol n10 may be 2.

$R^2$ may be substituted or unsubstituted alkyl. $R^2$ may be unsubstituted alkyl. $R^2$ may be $R^{17}$-substituted or unsubstituted alkyl. $R^2$ may be substituted or unsubstituted alkyl. $R^2$ may be substituted or unsubstituted $C_1$-$C_{20}$ alkyl. $R^2$ may be $R^{17}$-substituted or unsubstituted $C_1$-$C_{20}$ alkyl. $R^2$ may be substituted or unsubstituted $C_1$-$C_{10}$ alkyl. $R^2$ may be $R^{17}$-substituted or unsubstituted $C_1$-$C_{10}$ alkyl. $R^2$ may be substituted or unsubstituted $C_1$-$C_5$ alkyl. $R^2$ may be $R^{17}$-substituted or unsubstituted $C_1$-$C_5$ alkyl.

$R^2$ may be substituted or unsubstituted heteroalkyl. $R^2$ may be unsubstituted heteroalkyl. $R^2$ may be substituted or unsubstituted 2 to 20 membered heteroalkyl. $R^2$ may be $R^{17}$-substituted or unsubstituted 2 to 20 membered heteroalkyl. $R^2$ may be substituted or unsubstituted 2 to 10 membered heteroalkyl. $R^2$ may be $R^{17}$-substituted or unsubstituted 2 to 10 membered heteroalkyl. $R^2$ may be substituted or unsubstituted 2 to 6 membered heteroalkyl. $R^2$ may be $R^{17}$-substituted or unsubstituted 2 to 6 membered heteroalkyl.

$R^2$ may be substituted or unsubstituted cycloalkyl. $R^2$ may be unsubstituted cycloalkyl. $R^2$ may be $R^{17}$-substituted or unsubstituted 3 to 20 membered cycloalkyl. $R^2$ may be substituted or unsubstituted 3 to 20 membered cycloalkyl. $R^2$ may be substituted or unsubstituted 3 to 10 membered cycloalkyl. $R^2$ may be $R^{17}$-substituted or unsubstituted 3 to 10 membered cycloalkyl. $R^2$ may be substituted or unsubstituted 3 to 6 membered cycloalkyl. $R^2$ may be $R^{17}$-substituted or unsubstituted 3 to 6 membered cycloalkyl.

$R^2$ may be substituted or unsubstituted heterocycloalkyl. $R^2$ may be unsubstituted heterocycloalkyl. $R^2$ may be substituted or unsubstituted 3 to 20 membered heterocycloalkyl. $R^2$ may be $R^{17}$-substituted or unsubstituted 3 to 20 membered heterocycloalkyl. $R^2$ may be substituted or unsubstituted 3 to 10 membered heterocycloalkyl. $R^2$ may be $R^{17}$-substituted or unsubstituted 3 to 10 membered heterocycloalkyl. $R^2$ may be substituted or unsubstituted 3 to 6 membered heterocycloalkyl. $R^2$ may be $R^{17}$-substituted or unsubstituted 3 to 6 membered heterocycloalkyl.

$R^2$ may be substituted or unsubstituted aryl. $R^2$ may be unsubstituted aryl. $R^2$ may be substituted or unsubstituted 5 to 10 membered aryl. $R^2$ may be $R^{17}$-substituted or unsubstituted 5 to 10 membered aryl. $R^2$ may be substituted or unsubstituted 5 to 8 membered aryl. $R^2$ may be $R^{17}$-substituted or unsubstituted 5 to 8 membered aryl. $R^2$ may be substituted or unsubstituted 6 membered aryl. $R^2$ may be $R^{17}$-substituted or unsubstituted 6 membered aryl.

$R^2$ may be substituted or unsubstituted heteroaryl. $R^2$ may be unsubstituted heteroaryl. $R^2$ may be substituted or unsubstituted 5 to 10 membered heteroaryl. $R^2$ may be $R^{17}$-substituted or unsubstituted 5 to 10 membered heteroaryl. $R^2$ may be substituted or unsubstituted 5 to 8 membered heteroaryl. $R^2$ may be $R^{17}$-substituted or unsubstituted 5 to 8 membered heteroaryl. $R^2$ may be substituted or unsubstituted 5 or 6 membered heteroaryl. $R^2$ may be $R^{17}$-substituted or unsubstituted 5 or 6 membered heteroaryl.

$R^{17}$ is independently halogen, $-N_3$, $-CF_3$, $-CCl_3$, $-CBr_3$, $-CI_3$, $-CN$, $-CHO$, $-OR^{17A}$, $-NR^{17B}R^{17C}$, $-COOR^{17A}$, $-C(O)NR^{17B}R^{17C}$, $-NO_2$, $-SR^{17D}$, $-S(O)_{n17}R^{17B}$, $-S(O)_{n7}OR^{17B}$, $-S(O)_{n17}NR^{17B}R^{17C}$, $-NHNR^{17B}R^{17C}$, $-ONR^{17B}R^{17C}$, $-NHC(O)NHNR^{17B}R^{17C}$, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl. $R^{17}$ may be halogen, $-CF_3$, $-OR^{17A}NR^{17B}R^{17C}$, $-COOR^{17A}$, or $R^{18}$-substituted or unsubstituted alkyl. $R^{17}$ may be $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl.

$R^{17A}$, $R^{17B}$, $R^{17C}$, and $R^{17D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n17 is 1 or 2. $R^{17A}$, $R^{17B}$, $R^{17C}$, and $R^{17D}$ may independently be hydrogen or substituted or unsubstituted alkyl.

$R^{17A}$, $R^{17B}$, $R^{17C}$, and $R^{17D}$ may independently be hydrogen. $R^{17A}$, $R^{17B}$, $R^{17C}$, and $R^{17D}$ may independently be substituted or unsubstituted alkyl. $R^{17A}$, $R^{17B}$, $R^{17C}$, and $R^{17D}$ may independently be substituted or unsubstituted aryl. The symbol n17 may be 1. The symbol n17 may be 2.

$R^{18}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl. $R^{18}$ may be halogen, $-CF_3$, $-OH$, $-COOH$, or unsubstituted alkyl. $R^{18}$ may be $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$ substituted or unsubstituted heteroaryl.

$R^{19}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

$R^{20}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^2$ is $R^{17}$-substituted or unsubstituted alkyl or $R^{17}$-substituted or unsubstituted aryl. $R^{17}$ may be halogen, $-CF_3$, $-OR^{17A}$. $R^{17}$ may be halogen. $R^{17}$ may be $-CF_3$. $R^{17}$ may be $-OR^{17A}$. $R^{17A}$ may be hydrogen or unsubstituted $C_1$-$C_5$ alkyl. In embodiments, X is $-C(O)-$ and $R^2$ is $R^{17}$-substituted or unsubstituted alkyl, or $R^{17}$-substituted or unsubstituted aryl, where $R^{17}$ is $-CF_3$, $OR^{17A}$. $R^{17A}$ may be hydrogen or unsubstituted $C_1$-$C_5$ alkyl. In embodiments, $R^2$ is $R^{17}$-substituted or unsubstituted aryl, where $R^{17}$ is $R^{18}$-substituted or unsubstituted alkyl (e.g. $C_1$-$C_5$ alkyl), $-OR^{17A}$, or $-CF_3$. $R^{17A}$ may be hydrogen or substituted or unsubstituted alkyl (e.g. $C_1$-$C_5$ alkyl). $R^{17}$ may be methyl. $R^{17A}$ may be methyl.

In embodiments, $R^2$ is $R^{17}$-substituted or unsubstituted alkyl or $R^{17}$-substituted or unsubstituted aryl and $R^1$ is $R^{10}$-substituted or unsubstituted alkyl, unsubstituted cycloalkyl, or $R^{10}$-substituted or unsubstituted aryl. $R^{17}$ and $R^{10}$ are as described herein, including embodiments thereof. $L^1$ and $L^2$ may independently be a bond, —C(O)—, substituted or unsubstituted alkylene, substituted or unsubstituted heteroarylene, or substituted or unsubstituted arylene. In embodiments, $L^1$ and $L^2$ are a bond. $L^1$ and $L^2$ are substituted or unsubstituted alkylene. In embodiments, $L^1$ is substituted or unsubstituted alkylene and $L^2$ is a bond.

$R^3$ may be hydrogen, halogen, —$N_3$, —$CF_3$, —$CCl_3$, —$CBr_3$, —$CI_3$, —CN, —CHO, —$OR^{3A}$, —$NR^{3B}R^{3C}$, —$COOR^{3A}$, —C(O)$NR^{3B}R^3$, —$NO_2$, —$SR^{3D}$, —S(O)$_{n3}R^{3B}$, —S(O)$_{n3}OR^{3B}$, —S(O)$_{n3}NR^{3B}R^{3C}$, —NHN$R^{3B}R^{3C}$, —ON$R^{3B}R^{3C}$, —NHC(O)NHN$R^{3B}R^{3C}$. $R^3$ may be hydrogen or halogen. $R^3$ may be hydrogen. $R^3$ may be halogen. $R^3$ may be substituted or unsubstituted alkyl. $R^3$ may be unsubstituted alkyl. $R^3$ may be $R^{21}$-substituted or unsubstituted alkyl. $R^3$ may be substituted or unsubstituted $C_1$-$C_{20}$ alkyl. $R^3$ may be $R^{21}$-substituted or unsubstituted $C_1$-$C_{20}$ alkyl. $R^3$ may be substituted or unsubstituted $C_1$-$C_{10}$ alkyl. $R^3$ may be $R^{21}$-substituted or unsubstituted $C_1$-$C_{10}$ alkyl. $R^3$ may be substituted or unsubstituted $C_1$-$C_5$ alkyl. $R^3$ may be $R^{21}$-substituted or unsubstituted $C_1$-$C_5$ alkyl.

$R^{21}$ is halogen, —$N_3$, —$NO_2$, —$CF_3$, —$CCl_3$, —$CBr_3$, —$CI_3$, —CN, —OH, —$NH_2$, —COOH, —$CONH_2$, —SH, —$SO_3H$, —$SO_4H$, —$SO_2NH_2$, —$NHNH_2$, —$ONH_2$, —$OCH_3$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^{3A}$ may be hydrogen. $R^{3A}$ may be unsubstituted alkyl. $R^{3B}$, $R^{3C}$, and $R^{3D}$ may independently be hydrogen, substituted or unsubstituted alkyl, or substituted or unsubstituted aryl. $R^{3B}$, $R^{3C}$, and $R^{3D}$ may independently be hydrogen or substituted or unsubstituted alkyl. $R^{3B}$, $R^{3C}$, and $R^{3D}$ may independently be hydrogen. $R^{3B}$, $R^{3C}$, and $R^{3D}$ may independently be substituted or unsubstituted alkyl. $R^{3B}$, $R^{3C}$, and $R^{3D}$ may independently be substituted or unsubstituted heteroalkyl. $R^{3B}$, $R^{3C}$, and $R^{3D}$ may independently be substituted or unsubstituted cycloalkyl. $R^{3B}$, $R^{3C}$, and $R^{3D}$ may independently be substituted or unsubstituted heterocycloalkyl $R^{3B}$, $R^{3C}$, and $R^{3D}$ may independently be substituted or unsubstituted aryl. $R^{3B}$, $R^{3C}$, and $R^{3D}$ may independently be substituted or unsubstituted heteroaryl.

$R^5$ may be hydrogen. $R^5$ may be substituted or unsubstituted alkyl. $R^5$ may be unsubstituted alkyl. $R^5$ may be $R^{22}$-substituted or unsubstituted alkyl. $R^5$ may be substituted or unsubstituted $C_1$-$C_{20}$ alkyl. $R^5$ may be $R^{22}$-substituted or unsubstituted $C_1$-$C_{20}$ alkyl. $R^5$ may be substituted or unsubstituted $C_1$-$C_{10}$ alkyl. $R^5$ may be $R^{22}$-substituted or unsubstituted $C_1$-$C_{10}$ alkyl. $R^5$ may be substituted or unsubstituted $C_1$-$C_5$ alkyl. $R^5$ may be $R^{22}$-substituted or unsubstituted $C_1$-$C_5$ alkyl. $R^5$ may be unsubstituted $C_1$-$C_3$ alkyl.

$R^{22}$ is halogen, —$N_3$, —$NO_2$, —$CF_3$, —$CCl_3$, —$CBr_3$, —$CI_3$, —CN, —OH, —$NH_2$, —COOH, —$CONH_2$, —SH, —$SO_3H$, —$SO_4H$, —$SO_2NH_2$, —$NHNH_2$, —$ONH_2$, —$OCH_3$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^6$ may be halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{n6}OR^{6B}$, —$SO_{n6}NR^{6B}R^6$, —$NHNR^{6B}R^{6C}$, —$ONR^{6B}R^{6C}$, —NHC(O)$NHNR^{6B}R^{6C}$. $R^6$ may be halogen. $R^6$ may be substituted or unsubstituted alkyl. $R^6$ may be unsubstituted alkyl. $R^6$ may be $R^{23}$-substituted or unsubstituted alkyl. $R^6$ may be substituted or unsubstituted $C_1$-$C_{20}$ alkyl. $R^6$ may be $R^{23}$-substituted or unsubstituted $C_1$-$C_{20}$ alkyl. $R^6$ may be substituted or unsubstituted $C_1$-$C_{10}$ alkyl. $R^6$ may be $R^{23}$-substituted or unsubstituted $C_1$-$C_{10}$ alkyl. $R^6$ may be substituted or unsubstituted $C_1$-$C_5$ alkyl. $R^6$ may be $R^{23}$-substituted or unsubstituted $C_1$-$C_5$ alkyl. $R^6$ may be methyl, ethyl or propyl. $R^6$ may be methyl. $R^6$ may be ethyl (e.g. unsubstituted ethyl). $R^6$ may be propyl (e.g. unsubstituted propyl).

$R^{6A}$ may be hydrogen. $R^{6A}$ may be unsubstituted alkyl. $R^{6B}$, $R^{6C}$, and $R^{6D}$ may independently be hydrogen, substituted or unsubstituted alkyl, or substituted or unsubstituted aryl. $R^{6B}$, $R^{6C}$, and $R^{6D}$ may independently be hydrogen or substituted or unsubstituted alkyl. $R^{6B}$, $R^{6C}$, and $R^{6D}$ may independently be hydrogen. $R^{6B}$, $R^{6C}$, and $R^{6D}$ may independently be substituted or unsubstituted alkyl. $R^{6B}$, $R^{6C}$, and $R^{6D}$ may independently be substituted or unsubstituted heteroalkyl. $R^{6B}$, $R^{6C}$, and $R^{6D}$ may independently be substituted or unsubstituted cycloalkyl. $R^{6B}$, $R^{6C}$, and $R^{6D}$ may independently be substituted or unsubstituted heterocycloalkyl $R^{6B}$, $R^{6C}$, and $R^{6D}$ may independently be substituted or unsubstituted aryl. $R^{6B}$, $R^{6C}$, and $R^{6D}$ may independently be substituted or unsubstituted heteroaryl.

$R^{23}$ is halogen, —$N_3$, —$NO_2$, —$CF_3$, —$CCl_3$, —$CBr_3$, —$CI_3$, —CN, —OH, —$NH_2$, —COOH, —$CONH_2$, —SH, —$SO_3H$, —$SO_4H$, —$SO_2NH_2$, —$NHNH_2$, —$ONH_2$, —$OCH_3$, —NHC(O)$NHNH_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

$R^{24}$ is halogen, —$N_3$, —$NO_2$, —$CF_3$, —$CCl_3$, —$CBr_3$, —$CI_3$, —CN, —OH, —$NH_2$, —COOH, —$CONH_2$, —SH, —$SO_3H$, —$SO_4H$, —$SO_2NH_2$, —$NHNH_2$, —$ONH_2$, —$OCH_3$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^7$ may independently be hydrogen, halogen, —$N_3$, —$CF_3$, —$CCl_3$, —$CBr_3$, —$CI_3$, —CN, —CHO, —$OR^{7A}$, —$NR^{7B}R^{7C}$, —$COOR^{7A}$, —C(O)$NR^{7B}R^{7C}$, —$NO_2$, —$SR^{7D}$, —S(O)$_{n7}R^{7B}$, —S(O)$_{n7}OR^{7B}$, —S(O)$_{n7}NR^{7B}R^{7C}$, —NHN$R^{7B}R^{7C}$, —ON$R^{7B}R^{7D}$, —NHC(O)NHN$R^{7B}R^{7C}$.

$R^7$ may independently be hydrogen, halogen, —$OR^{7A}$, —$NO_2$, or —CN. $R^1$ may independently be hydrogen. $R^7$ may independently be halogen. $R^7$ may independently be hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ may independently be substituted or unsubstituted alkyl. $R^7$ may independently be $R^{25}$-substituted or unsubstituted alkyl. $R^7$ may independently be unsubstituted alkyl. $R^7$ may independently be substituted or unsubstituted $C_1$-$C_{20}$ alkyl. $R^7$ may independently be $R^{25}$-substituted or unsubstituted $C_1$-$C_{20}$ alkyl. $R^7$ may independently be substituted or unsubstituted $C_1$-$C_{10}$ alkyl. $R^7$ may independently be $R^{25}$-substituted or unsubstituted $C_1$-$C_{10}$ alkyl. $R^7$ may independently be substituted or unsubstituted $C_1$-$C_5$ alkyl. $R^7$ may independently be $R^{25}$-substituted or unsubstituted $C_1$-$C_5$ alkyl.

$R^7$ may independently be substituted or unsubstituted heteroalkyl. $R^7$ may independently be unsubstituted heteroalkyl. $R^7$ may independently be substituted or unsubstituted 2 to 20 membered heteroalkyl. $R^7$ may independently be $R^{25}$-substituted or unsubstituted 2 to 20 membered heteroalkyl. $R^7$ may independently be substituted or unsubstituted 2 to 10 membered heteroalkyl. $R^7$ may independently be $R^{25}$-substituted or unsubstituted 2 to 10 membered heteroalkyl. $R^7$ may independently be substituted or unsubstituted 2 to 6 membered heteroalkyl. $R^7$ may independently be $R^{25}$-substituted or unsubstituted 2 to 6 membered heteroalkyl.

$R^7$ may independently be substituted or unsubstituted cycloalkyl. $R^7$ may independently be unsubstituted cycloalkyl. $R^7$ may independently be $R^{25}$-substituted or unsubstituted 3 to 20 membered cycloalkyl. $R^7$ may independently be substituted or unsubstituted 3 to 20 membered cycloalkyl. $R^7$ may independently be substituted or unsubstituted 3 to 10 membered cycloalkyl. $R^7$ may independently be $R^{25}$-substituted or unsubstituted 3 to 10 membered cycloalkyl. $R^7$ may independently be substituted or unsubstituted 3 to 6 membered cycloalkyl. $R^7$ may independently be $R^{25}$-substituted or unsubstituted 3 to 6 membered cycloalkyl.

$R^7$ may independently be substituted or unsubstituted heterocycloalkyl. $R^7$ may independently be unsubstituted heterocycloalkyl. $R^7$ may independently be substituted or unsubstituted 3 to 20 membered heterocycloalkyl. $R^7$ may independently be $R^{25}$-substituted or unsubstituted 3 to 20 membered heterocycloalkyl. $R^7$ may independently be substituted or unsubstituted 3 to 10 membered heterocycloalkyl. $R^7$ may independently be $R^{25}$-substituted or unsubstituted 3 to 10 membered heterocycloalkyl. $R^7$ may independently be substituted or unsubstituted 3 to 6 membered heterocycloalkyl. $R^7$ may independently be $R^{25}$-substituted or unsubstituted 3 to 6 membered heterocycloalkyl.

$R^7$ may independently be substituted or unsubstituted aryl. $R^7$ may independently be unsubstituted aryl. $R^7$ may independently be substituted or unsubstituted 5 to 10 membered aryl. $R^7$ may independently be $R^{25}$-substituted or unsubstituted 5 to 10 membered aryl. $R^7$ may independently be substituted or unsubstituted 5 to 8 membered aryl. $R^7$ may independently be $R^{25}$-substituted or unsubstituted 5 to 8 membered aryl. $R^7$ may independently be substituted or unsubstituted 6 membered aryl. $R^7$ may independently be $R^{25}$-substituted or unsubstituted 6 membered aryl.

$R^7$ may independently be substituted or unsubstituted heteroaryl. $R^7$ may independently be unsubstituted heteroaryl. $R^7$ may independently be substituted or unsubstituted 5 to 10 membered heteroaryl. $R^7$ may independently be $R^{25}$-substituted or unsubstituted 5 to 10 membered heteroaryl. $R^7$ may independently be substituted or unsubstituted 5 to 8 membered heteroaryl. $R^7$ may independently be $R^{25}$-substituted or unsubstituted 5 to 8 membered heteroaryl. $R^7$ may independently be substituted or unsubstituted 5 or 6 membered heteroaryl. $R^7$ may independently be $R^{25}$-substituted or unsubstituted 5 or 6 membered heteroaryl.

$R^{7A}$ may independently be hydrogen. $R^{7A}$ may independently be unsubstituted alkyl. $R^{7B}$, $R^{7C}$, and $R^{7D}$ may independently be hydrogen, substituted or unsubstituted alkyl, or substituted or unsubstituted aryl. $R^{7B}$, $R^{7C}$, and $R^{7D}$ may independently be hydrogen or substituted or unsubstituted alkyl. $R^{7B}$, $R^{7C}$, and $R^{7D}$ may independently be hydrogen. $R^{7B}$, $R^{7C}$, and $R^{7D}$ may independently be substituted or unsubstituted alkyl. $R^{7B}$, $R^{7C}$, and $R^{7D}$ may independently be substituted or unsubstituted heteroalkyl. $R^{7B}$, $R^{7C}$, and $R^{7D}$ may independently be substituted or unsubstituted cycloalkyl. $R^{7B}$, $R^{7C}$, and $R^{7D}$ may independently be substituted or unsubstituted heterocycloalkyl $R^{7B}$, $R^{7C}$, and $R^{7D}$ may independently be substituted or unsubstituted aryl. $R^{7B}$, $R^{7C}$, and $R^{7D}$ may independently be substituted or unsubstituted heteroaryl.

$R^{25}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

$R^{26}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl.

$R^{27}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl.

$R^{28}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

The symbol z1 may be 1. The symbol z1 may be 2. The symbol z1 may be 3. The symbol z1 may be 4. The symbol z1 may be 5. The symbol z1 may be 6.

$R^8$ may independently be hydrogen, halogen, $-OR^{8A}$, $-NO_2$, or $-CN$. $R^8$ may independently be hydrogen. $R^8$ may independently be halogen. $R^8$ may independently be hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^8$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^8$ may independently be substituted or unsubstituted alkyl. $R^8$ may independently be $R^{29}$-substituted or unsubstituted alkyl. $R^8$ may independently be unsubstituted alkyl. $R^8$ may independently be substituted or unsubstituted $C_1$-$C_{20}$ alkyl. $R^8$ may independently be $R^{29}$-substituted or unsubstituted $C_1$-$C_{20}$ alkyl. $R^8$ may independently be substituted or unsubstituted $C_1$-$C_{10}$ alkyl. $R^8$ may independently be $R^{29}$-substituted or unsubstituted $C_1$-$C_{10}$ alkyl. $R^8$ may independently be substituted or unsubstituted $C_1$-$C_5$ alkyl. $R^8$ may independently be $R^{29}$-substituted or unsubstituted $C_1$-$C_5$ alkyl.

$R^8$ may independently be substituted or unsubstituted heteroalkyl. $R^8$ may independently be unsubstituted heteroalkyl. $R^8$ may independently be substituted or unsubstituted 2 to 20 membered heteroalkyl. $R^8$ may independently be $R^{29}$-substituted or unsubstituted 2 to 20 membered heteroalkyl. $R^8$ may independently be substituted or unsubstituted 2 to 10 membered heteroalkyl. $R^8$ may independently be $R^{29}$-substituted or unsubstituted 2 to 10 membered heteroalkyl. $R^8$ may independently be substituted or unsubstituted 2 to 6 membered heteroalkyl. $R^8$ may independently be $R^{29}$-substituted or unsubstituted 2 to 6 membered heteroalkyl.

$R^8$ may independently be substituted or unsubstituted cycloalkyl. $R^8$ may independently be unsubstituted cycloalkyl. $R^8$ may independently be $R^{29}$-substituted or unsubstituted 3 to 20 membered cycloalkyl. $R^8$ may independently be substituted or unsubstituted 3 to 20 membered cycloalkyl. $R^8$ may independently be substituted or unsubstituted 3 to 10 membered cycloalkyl. $R^8$ may independently be $R^{29}$-substituted or unsubstituted 3 to 10 membered cycloalkyl. $R^8$ may independently be substituted or unsubstituted 3 to 6 membered cycloalkyl. $R^8$ may independently be $R^{29}$-substituted or unsubstituted 3 to 6 membered cycloalkyl.

$R^8$ may independently be substituted or unsubstituted heterocycloalkyl. $R^8$ may independently be unsubstituted heterocycloalkyl. $R^8$ may independently be substituted or unsubstituted 3 to 20 membered heterocycloalkyl. $R^8$ may independently be $R^{29}$-substituted or unsubstituted 3 to 20 membered heterocycloalkyl. $R^8$ may independently be substituted or unsubstituted 3 to 10 membered heterocycloalkyl. $R^8$ may independently be $R^{29}$-substituted or unsubstituted 3 to 10 membered heterocycloalkyl. $R^8$ may independently be substituted or unsubstituted 3 to 6 membered heterocycloalkyl. $R^8$ may independently be $R^{29}$-substituted or unsubstituted 3 to 6 membered heterocycloalkyl.

$R^8$ may independently be substituted or unsubstituted aryl. $R^8$ may independently be unsubstituted aryl. $R^8$ may independently be substituted or unsubstituted 5 to 10 membered aryl. $R^8$ may independently be $R^{29}$-substituted or unsubstituted 5 to 10 membered aryl. $R^8$ may independently be substituted or unsubstituted 5 to 8 membered aryl. $R^8$ may independently be $R^{29}$-substituted or unsubstituted 5 to 8 membered aryl. $R^8$ may independently be substituted or unsubstituted 6 membered aryl. $R^8$ may independently be $R^{29}$-substituted or unsubstituted 6 membered aryl.

$R^8$ may independently be substituted or unsubstituted heteroaryl. $R^8$ may independently be unsubstituted heteroaryl. $R^8$ may independently be substituted or unsubstituted 5 to 10 membered heteroaryl. $R^8$ may independently be $R^{29}$-substituted or unsubstituted 5 to 10 membered heteroaryl. $R^8$ may independently be substituted or unsubstituted 5 to 8 membered heteroaryl. $R^8$ may independently be $R^{29}$-substituted or unsubstituted 5 to 8 membered heteroaryl. $R^8$ may independently be substituted or unsubstituted 5 or 6 membered heteroaryl. $R^8$ may independently be $R^{29}$-substituted or unsubstituted 5 or 6 membered heteroaryl.

$R^{8A}$ may independently be hydrogen. $R^{8A}$ may independently be unsubstituted alkyl. $R^{8B}$, $R^{8C}$, and $R^{8D}$ may independently be hydrogen, substituted or unsubstituted alkyl, or substituted or unsubstituted aryl. $R^{8B}$, $R^{8C}$, and $R^{8D}$ may independently be hydrogen or substituted or unsubstituted alkyl. $R^{8B}$, $R^{8C}$, and $R^{8D}$ may independently be hydrogen. $R^{8B}$, $R^{8C}$, and $R^{8D}$ may independently be substituted or unsubstituted alkyl. $R^{8B}$, $R^{8C}$, and $R^{8D}$ may independently be substituted or unsubstituted heteroalkyl. $R^{8B}$, $R^{8C}$, and $R^{8D}$ may independently be substituted or unsubstituted cycloalkyl. $R^{8B}$, $R^{8C}$, and $R^{8D}$ may independently be substituted or unsubstituted heterocycloalkyl $R^{8B}$, $R^{8C}$, and $R^{8D}$ may independently be substituted or unsubstituted aryl. $R^{8B}$, $R^{8C}$, and $R^{8D}$ may independently be substituted or unsubstituted heteroaryl.

$R^{29}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl.

$R^{30}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

$R^{31}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl.

$R^{32}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

The symbol z2 may be 1. The symbol z2 may be 2. The symbol z2 may be 3. The symbol z2 may be 4. The symbol z2 may be 5. The symbol z2 may be 6. The symbol z2 may be 7. The symbol z2 may be 8.

The symbols n, n3, n6, n7, and n8 may independently be 1. The symbols n, n3, n6, n7, and n8 may independently be 2.

In embodiments, X is $-C(O)-$ and -$L^1$-$R^1$ is unsubstituted phenyl, and -$L^2$-$R^2$ is not methyl, p-substituted or unsubstituted phenyl, or unsubstituted pyridine. In embodiments, X is $-C(O)-$ and -$L^1$-$R^1$ is unsubstituted aryl, and -$L^2$-$R^2$ is not methyl, p-substituted or unsubstituted phenyl, or unsubstituted pyridine. In embodiments, X is $-C(O)-$ and -$L^1$-$R^1$ is unsubstituted aryl, and -$L^2$-$R^2$ is not hydrogen, substituted or unsubstituted alkyl, substituted or unsubstituted aryl, or substituted or unsubstituted heteroaryl. In embodiments, X is $-C(O)-$ and -$L^1$-$R^1$ is substituted or unsubstituted aryl, and -$L^2$-$R^2$ is not hydrogen, substituted or unsubstituted alkyl, substituted or unsubstituted aryl, or substituted or unsubstituted heteroaryl. In embodiments, X is $-C(O)-$ and -$L^1$-$R^1$ is hydrogen or substituted or unsubstituted aryl, and -$L^2$-$R^2$ is not hydrogen, substituted or unsubstituted alkyl, substituted or unsubstituted aryl, or substituted or unsubstituted heteroaryl.

In embodiments, X is $-CH_2-$ and -$L^1$-$R^1$ is unsubstituted phenyl, and -$L^2$-$R^2$ is not methyl, p-substituted or unsubstituted phenyl, or unsubstituted pyridine. In embodiments, X is $-CH_2-$ and -$L^1$-$R^1$ is unsubstituted aryl, and -$L^2$-$R^2$ is not methyl, p-substituted or unsubstituted phenyl, or unsubstituted pyridine. In embodiments, X is $-CH_2-$ and -$L^1$-$R^1$ is unsubstituted aryl, and -$L^2$-$R^2$ is not hydrogen, substituted or unsubstituted alkyl, substituted or unsubstituted aryl, or substituted or unsubstituted heteroaryl. In embodiments, X is —CH$_2$— and -L$^1$-R$^1$ is substituted or unsubstituted aryl, and -L$^2$-R$^2$ is not hydrogen, substituted or unsubstituted alkyl, substituted or unsubstituted aryl, or substituted or unsubstituted heteroaryl. In embodiments, X is —CH$_2$— and -L$^1$-R$^1$ is hydrogen or substituted or unsubstituted aryl, and -L$^2$-R$^2$ is not hydrogen, substituted or unsubstituted alkyl, substituted or unsubstituted aryl, or substituted or unsubstituted heteroaryl.

The compound of formula (I) may have formula:

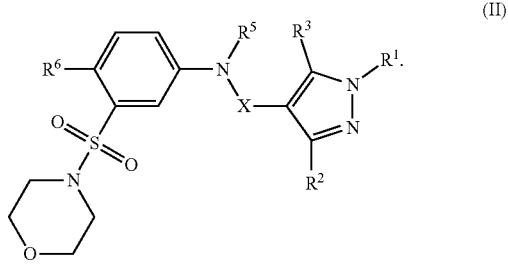

(II)

The compound of formula (I) may have formula:

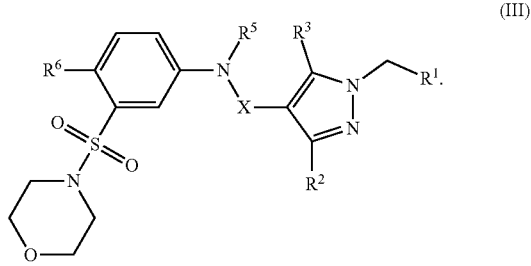

(III)

In embodiments, R$^1$ of the compounds herein (e.g. formulas (I), (II), or (III)) is R$^{10}$-substituted or unsubstituted alkyl, R$^{10}$-substituted or unsubstituted cycloalkyl, or R$^{10}$-substituted or unsubstituted aryl, wherein R$^{10}$ is independently halogen, —N$_3$, —CF$_3$, —CCl$_3$, —CBr$_3$, —CI$_3$, —CN, —CHO, —OR$^{10A}$, —NR$^{10B}$R$^{10C}$, —COOR$^{10A}$, —C(O)NR$^{10B}$R$^{10C}$, —NO$_2$, —SR$^{10D}$, —S(O)$_{n10}$R$^{10B}$, —S(O)$_{n10}$OR$^{10B}$, —S(O)$_{n10}$NR$^{10B}$R$^{10C}$, —NHNR$^{10B}$R$^{10C}$, —ONR$^{10B}$R$^{10C}$, —NHC(O)NHNR$^{10B}$R$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{10A}$, R$^{10B}$, R$^{10C}$, R$^{10D}$ and n10 are as described herein, including embodiments thereof. In embodiments, R$^1$ of the compounds herein (e.g. formulas (I), (II), or (III)) is R$^{10}$-substituted or unsubstituted alkyl, R$^{10}$-substituted or unsubstituted cycloalkyl, R$^{10}$-substituted or unsubstituted aryl, or R$^{10}$-substituted or unsubstituted heteroaryl.

In embodiments, R$^1$ is R$^{10}$-substituted or unsubstituted 5,6-fused ring aryl, 5,6-fused ring heteroaryl, 6,5-fused ring aryl, 6,5-fused ring heteroaryl, 6,6-fused ring aryl, or 6,6-fused ring heteroaryl. In embodiments, R$^1$ is R$^{10}$-substituted or unsubstituted 5,6-fused ring heteroaryl. In embodiments, R$^1$ is R$^{10}$-substituted or unsubstituted 6,6-fused ring aryl.

In embodiments, R$^1$ of the compounds herein (e.g. formulas (I), (II), or (III)) is R$^{10}$-substituted or unsubstituted alkyl, unsubstituted cycloalkyl, or R$^{10}$-substituted or unsubstituted aryl. R$^{10}$ may hydrogen, halogen, —CF$_3$, —OR$^{10A}$. R$^{10A}$ may be hydrogen or unsubstituted C$_1$-C$_5$ alkyl.

In embodiments, R$^2$ of the compounds herein (e.g. formulas (I), (II), or (III)) is R$^{17}$-substituted or unsubstituted alkyl or R$^{17}$-substituted or unsubstituted aryl. R$^{17}$ may be halogen, —CF$_3$, —OR$^{17A}$. R$^{17}$ may be halogen. R$^{17}$ may be —CF$_3$. R$^{17}$ may be —OR$^{17A}$. R$^{17A}$ may be hydrogen or unsubstituted C$_1$-C$_5$ alkyl. In embodiments, X is —C(O)—. R$^2$ may be R$^{17}$-substituted or unsubstituted alkyl, or R$^{17}$-substituted or unsubstituted aryl, where R$^{17}$ is —CF$_3$ or —OR$^{17A}$ R$^{17A}$ may be hydrogen or unsubstituted C$_1$-C$_5$ alkyl. In embodiments, R$^2$ is R$^{17}$-substituted or unsubstituted aryl, where R$^{17}$ is R$^{18}$-substituted or unsubstituted alkyl (e.g. C$_1$-C$_5$ alkyl), —OR$^{17A}$, or —CF$_3$. R$^{17A}$ may be hydrogen or substituted or unsubstituted alkyl (e.g. C$_1$-C$_5$ alkyl). R$^{17}$ may be methyl. R$^{17A}$ may be methyl.

In embodiments, R$^2$ of the compounds herein (e.g. formulas (I), (II), or (III)) is R$^{17}$-substituted or unsubstituted alkyl or R$^{17}$-substituted or unsubstituted aryl and R$^1$ is R$^{10}$-substituted or unsubstituted alkyl, unsubstituted cycloalkyl, or R$^{10}$-substituted or unsubstituted aryl. R$^{17}$ and R$^{10}$ are as described herein, including embodiments thereof. L$^1$ and L$^2$ may independently be a bond, —C(O)—, substituted or unsubstituted alkylene, substituted or unsubstituted heteroarylene, or substituted or unsubstituted arylene. In embodiments, L$^1$ and L$^2$ are a bond. L$^1$ and L$^2$ are substituted or unsubstituted alkylene. In embodiments, L$^1$ is substituted or unsubstituted alkylene and L$^2$ is a bond.

In embodiments, the compound of formula (I), (II), or (III) has formula:

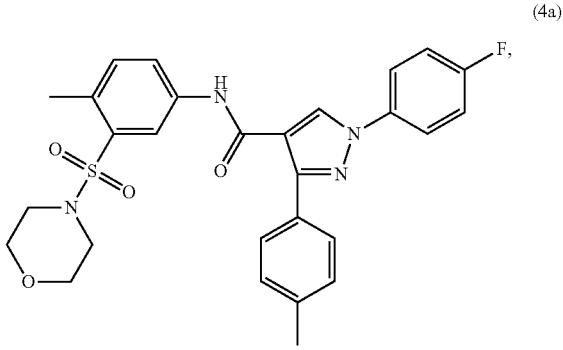

(4a)

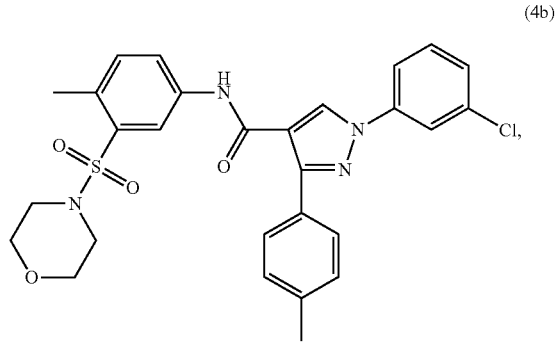

(4b)

-continued
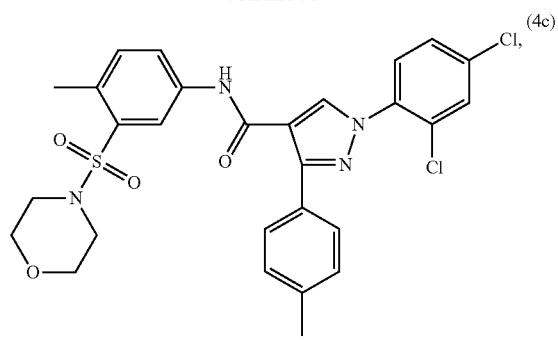
(4c)
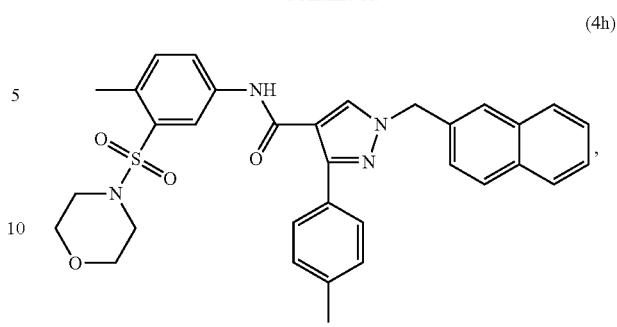
(4h)
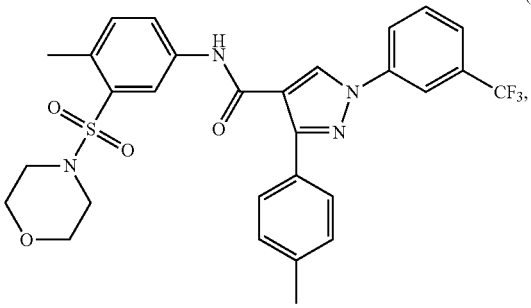
(4d)
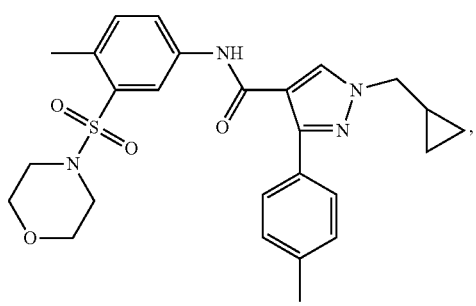
(4i)
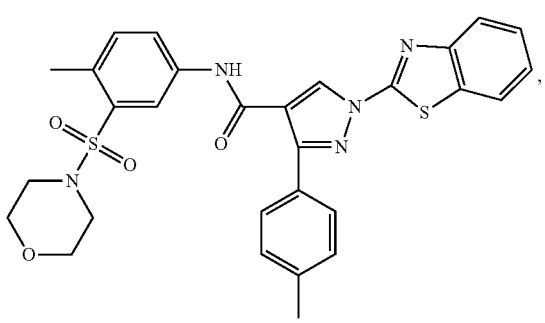
(4e)
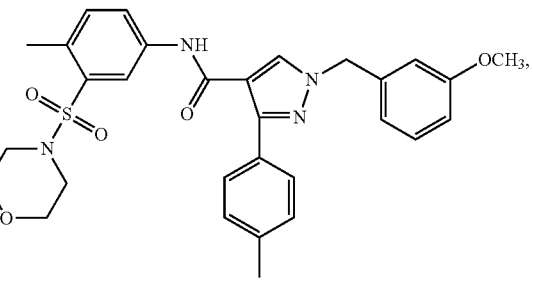
(4j)
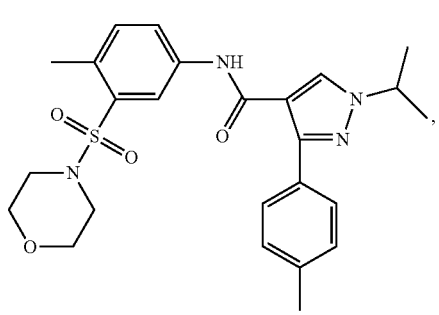
(4f)
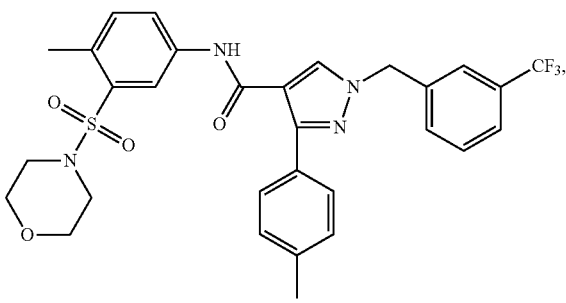
(4k)
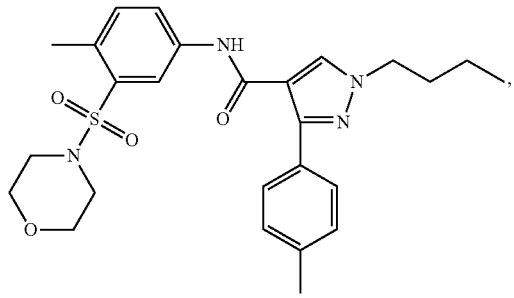
(4g)
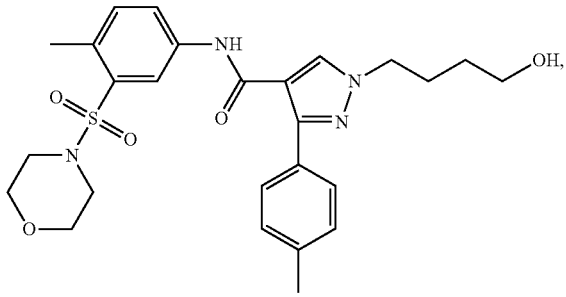
(4l)

(4m)
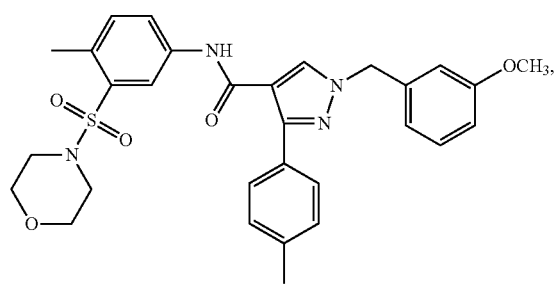
(4n)
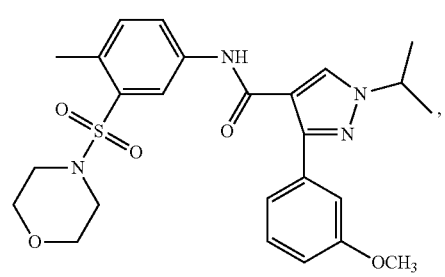
(4o)
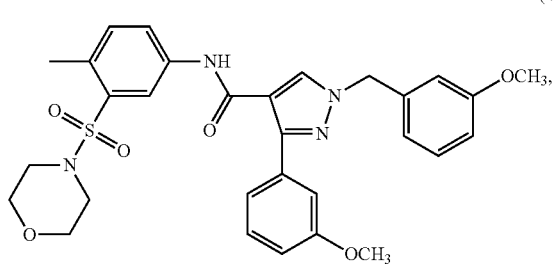
(4p)
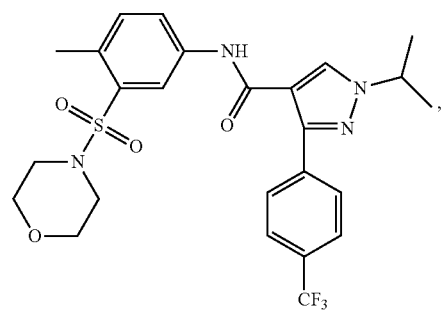
(4q)
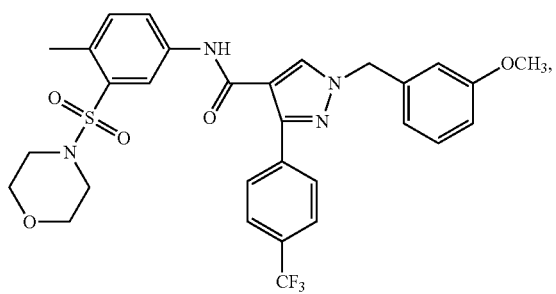
(4r)
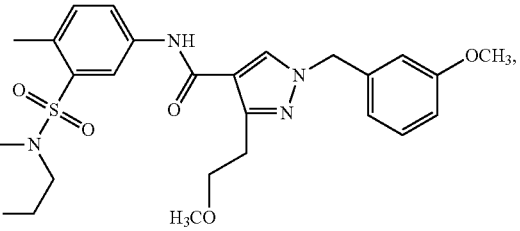
(4s)
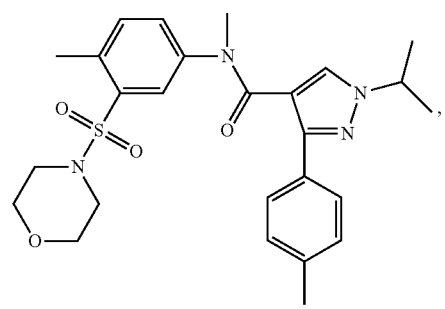
(8-1)
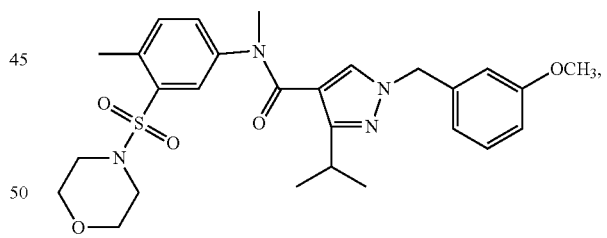
(8-2)
(8-3)
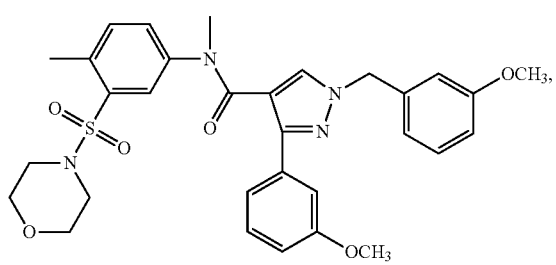

-continued

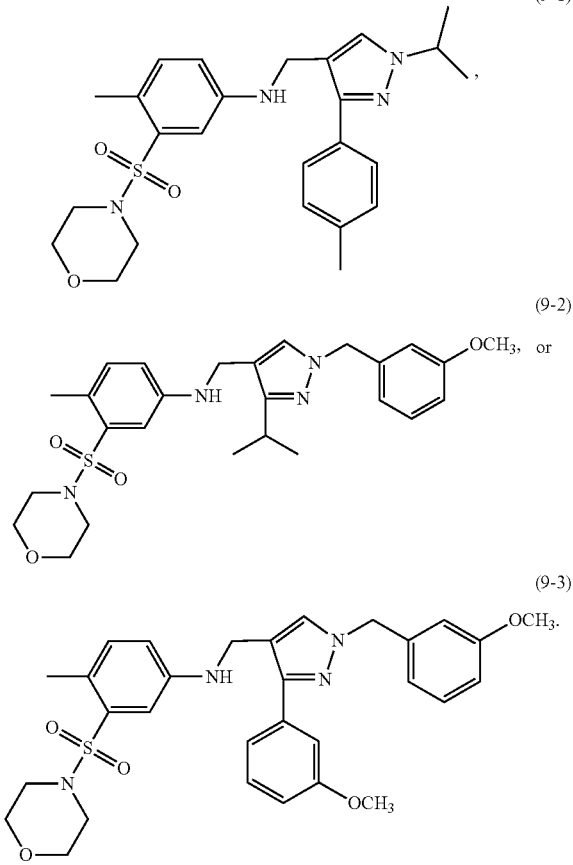

In embodiments, the compound herein (e.g. formula (I), (II), or (III)) has formula 4a, 4b, 4c, 4d, 4e, 4f, 4g, 4h, 4i, 4j, 4k, 4l, 4m, 4n, 4o, 4p, 4q, 4r, 4s, 8-1, 8-2, 8-3, 9-1, 9-2, or 9-3. In embodiments, the compound herein (e.g. formula (I), (II), or (III)) has formula 4a. In embodiments, the compound herein (e.g. formula (I), (II), or (III)) has formula 4b. In embodiments, the compound herein (e.g. formula (I), (II), or (III)) has formula 4c. In embodiments, the compound herein (e.g. formula (I), (II), or (III)) has formula 4d. In embodiments, the compound herein (e.g. formula (I), (II), or (III)) has formula 4e. In embodiments, the compound herein (e.g. formula (I), (II), or (III)) has formula 4f. In embodiments, the compound herein (e.g. formula (I), (II), or (III)) has formula 4g. In embodiments, the compound herein (e.g. formula (I), (II), or (III)) has formula 4h. In embodiments, the compound herein (e.g. formula (I), (II), or (III)) has formula 4i. In embodiments, the compound herein (e.g. formula (I), (II), or (III)) has formula 4j. In embodiments, the compound herein (e.g. formula (I), (II), or (III)) has formula 4k. In embodiments, the compound herein (e.g. formula (I), (II), or (III)) has formula 4l. In embodiments, the compound herein (e.g. formula (I), (II), or (III)) has formula 4m. In embodiments, the compound herein (e.g. formula (I), (II), or (III)) has formula 4n. In embodiments, the compound herein (e.g. formula (I), (II), or (III)) has formula 4o. In embodiments, the compound herein (e.g. formula (I), (II), or (III)) has formula 4p. In embodiments, the compound herein (e.g. formula (I), (II), or (III)) has formula 4q. In embodiments, the compound herein (e.g. formula (I), (II), or (III)) has formula 4r. In embodiments, the compound herein (e.g. formula (I), (II), or (III)) has formula 4s. In embodiments, the compound herein (e.g. formula (I), (II), or (III)) has formula 8-1. In embodiments, the compound herein (e.g. formula (I), (II), or (III)) has formula 8-2. In embodiments, the compound herein (e.g. formula (I), (II), or (III)) has formula 8-3. In embodiments, the compound herein (e.g. formula (I), (II), or (III)) has formula 9-1. In embodiments, the compound herein (e.g. formula (I), (II), or (III)) has formula 9-2. In embodiments, the compound herein (e.g. formula (I), (II), or (III)) has formula 9-3.

In embodiments, the compound herein (e.g. formula (I), (II), or (III)) is not a compound selected from 4a, 4b, 4c, 4d, 4e, 4f, 4g, 4h, 4i, 4j, 4k, 4l, 4m, 4n, 4o, 4p, 4q, 4r, 4s, 8-1, 8-2, 8-3, 9-1, 9-2, 9-3, Z533, Z201, Z380, Z254, Z991, E7, Z993, Z990, Z098, Z992, Z047, Z873, or Z26476908. In embodiments, the compound herein (e.g. formula (I), (II), or (III)) is not 4a. In embodiments, the compound herein (e.g. formula (I), (II), or (III)) is not 4b. In embodiments, the compound herein (e.g. formula (I), (II), or (III)) is not 4c. In embodiments, the compound herein (e.g. formula (I), (II), or (III)) is not 4d. In embodiments, the compound herein (e.g. formula (I), (II), or (III)) is not 4e. In embodiments, the compound herein (e.g. formula (I), (II), or (III)) is not 4f. In embodiments, the compound herein (e.g. formula (I), (II), or (III)) is not 4g. In embodiments, the compound herein (e.g. formula (I), (II), or (III)) is not 4h. In embodiments, the compound herein (e.g. formula (I), (II), or (III)) is not 4i. In embodiments, the compound herein (e.g. formula (I), (II), or (III)) is not 4j. In embodiments, the compound herein (e.g. formula (I), (II), or (III)) is not 4k. In embodiments, the compound herein (e.g. formula (I), (II), or (III)) is not 4l. In embodiments, the compound herein (e.g. formula (I), (II), or (III)) is not 4m. In embodiments, the compound herein (e.g. formula (I), (II), or (III)) is not 4n. In embodiments, the compound herein (e.g. formula (I), (II), or (III)) is not 4o. In embodiments, the compound herein (e.g. formula (I), (II), or (III)) is not 4p. In embodiments, the compound herein (e.g. formula (I), (II), or (III)) is not 4q. In embodiments, the compound herein (e.g. formula (I), (II), or (III)) is not 4r. In embodiments, the compound herein (e.g. formula (I), (II), or (III)) is not 4s. In embodiments, the compound herein (e.g. formula (I), (II), or (III)) is not 8-1. In embodiments, the compound herein (e.g. formula (I), (II), or (III)) is not 8-2. In embodiments, the compound herein (e.g. formula (I), (II), or (III)) is not 8-3. In embodiments, the compound herein (e.g. formula (I), (II), or (III)) is not 9-1. In embodiments, the compound herein (e.g. formula (I), (II), or (III)) is not 9-2. In embodiments, the compound herein (e.g. formula (I), (II), or (III)) is not 9-3. In embodiments, the compound herein (e.g. formula (I), (II), or (III)) is not Z533. In embodiments, the compound herein (e.g. formula (I), (II), or (III)) is not Z201. In embodiments, the compound herein (e.g. formula (I), (II), or (III)) is not Z380. In embodiments, the compound herein (e.g. formula (I), (II), or (III)) is not Z254. In embodiments, the compound herein (e.g. formula (I), (II), or (III)) is not Z991. In embodiments, the compound herein (e.g. formula (I), (II), or (III)) is not Z993. In embodiments, the compound herein (e.g. formula (I), (II), or (III)) is not Z990. In embodiments, the compound herein (e.g. formula (I), (II), or (III)) is not Z098. In embodiments, the compound herein (e.g. formula (I), (II), or (III)) is not Z992. In embodiments, the compound herein (e.g. formula (I), (II), or (III)) is not Z047. In embodiments, the compound herein (e.g. formula (I), (II), or (III)) is not Z873. In embodiments, the compound herein (e.g. formula (I), (II), or (III)) is not Z26476908. In embodiments, the compound herein (e.g. formula (I), (II), or (III)) is not E7. In embodiments, a compound is a compound described herein (e.g., a compound described in another aspect or embodiment herein, for example, in a pharmaceutical composition aspect or embodiment or in a method aspect or embodiment).

In another aspect a pharmaceutical composition is provided. The pharmaceutical composition includes a pharmaceutically acceptable excipient and a compound described herein, including a compound having formula:

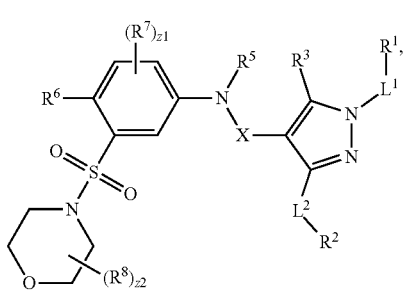

(I)

X is —C($R^{4A}$)($R^{4B}$)—, —C(O)—, —CY(OH)—. Y is hydrogen, halogen, —$N_3$, —$NO_2$, —$CF_3$, —$CCl_3$, —$CBr_3$, —$CI_3$, —CN, —$OR^{9A}$, —$NHR^{9A}$, —$COOR^{9A}$, —$CONHR^{9A}$, —SH, —$SO_3H$, —$SO_4H$, —$SO_2NH_2$, —$NHNH_2$, —$ONH_2$, —$OCH_3$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^1$ is independently a bond, —C(O)—, —C(O)O—, —O—, —S—, —$NR^{9B}$—, —C(O)$NR^{9B}$—, —S(O)$_n$—, —S(O)$NR^{9B}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ is independently a bond, —C(O)—, —C(O)O—, —O—, —S—, —$NR^{9C}$—, —C(O)$NR^{9C}$—, —S(O)$_n$—, —S(O)$NR^{9C}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$, $R^2$, $R^3$, $R^{4A}$, $R^{4B}$, $R^5$, $R^6$, $R^7$, and $R^8$ are independently hydrogen, halogen, —$N_3$, —$CF_3$, —$CCl_3$, —$CBr_3$, —$CI_3$, —CN, —CHO, —$OR^{11A}$, —$NR^{11B}R^{11C}$, —$COOR^{11A}$, —C(O)$NR^{11B}R^{11C}$, —$NO_2$, —$SR^{11D}$, —S(O)$_{n11}R^{11B}$, —S(O)$_{n11}OR^{11B}$, —S(O)$_{n11}NR^{11B}R^{11C}$, —$NHNR^{11B}R^{11C}$, —$ONR^{11B}R^{11C}$, —NHC(O)$NHNR^{11B}R^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{9A}$, $R^{9B}$, and $R^{9C}$ are independently hydrogen, halogen, —$N_3$, —$NO_2$, —$CF_3$, —$CCl_3$, —$CBr_3$, —$CI_3$, —CN, —OH, —$NH_2$, —COOH, —$CONH_2$, —SH, —$SO_3H$, —$SO_4H$, —$SO_2NH_2$, —$NHNH_2$, —$ONH_2$, —$OCH_3$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n and n11 are independently 1 or 2. The symbol z1 is 1, 2, 3, 4, 5, or 6. The symbol z2 is 1, 2, 3, 4, 5, 6, 7, or 8. $R^{11A}$, $R^{11B}$, $R^{11C}$, and $R^{11D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The pharmaceutical compositions contemplated herein include pharmaceutically acceptable salts thereof, as described herein, including embodiments thereof.

$R^1$ is as described herein, including embodiments thereof. $R^1$ of the pharmaceutical compositions herein may be hydrogen, halogen, —$N_3$, —$CF_3$, —$CCl_3$, —$CBr_3$, —$CI_3$, —CN, —CHO, —$OR^{11A}$, —$NR^{11B}R^{11C}$, —$COOR^{11A}$, —C(O)$NR^{11B}R^{11C}$, —$NO_2$, —$SR^{11D}$, —S(O)$_{n11}R^{11B}$, —S(O)$_{n11}OR^{11B}$, —S(O)$_{n11}NR^{11B}R^{11C}$, —$NHNR^{11B}R^{11C}$, —$ONR^{11B}R^{11C}$, —NHC(O)$NHNR^{11B}R^{11C}$. $R^1$ of the pharmaceutical compositions herein may be hydrogen, halogen, —$N_3$, —$CF_3$, —$CCl_3$, —$CBr_3$, —$CI_3$, —CN, —CHO, —$OR^{11A}$, or —$NO_2$. $R^1$ of the pharmaceutical compositions herein may be hydrogen. $R^1$ of the pharmaceutical compositions herein may be halogen. $R^2$ of the pharmaceutical compositions herein may be —$N_3$, —$CF_3$, —$CCl_3$, —$CBr_3$, —$CI_3$, —CN, —CHO, —$OR^{11A}$, or —$NO_2$. In embodiments, $R^1$ is not hydrogen. In embodiments, $R^1$ is not halogen. In embodiments, $R^1$ is not $N_3$, —$CF_3$, —$CCl_3$, —$CBr_3$, —$CI_3$, —CN, —CHO, —$OR^{11A}$, or —$NO_2$.

$R^2$ is as described herein, including embodiments thereof. $R^2$ of the pharmaceutical compositions herein may be hydrogen, halogen, —$N_3$, —$CF_3$, —$CCl_3$, —$CBr_3$, —$CI_3$, —CN, —CHO, —$OR^{11A}$, —$NR^{11B}R^{11C}$, —$COOR^{11A}$, —C(O)$NR^{11B}R^{11C}$, —$NO_2$, —$SR^{11D}$, —S(O)$_{n11}R^{11B}$, —S(O)$_{n11}OR^{11B}$, —S(O)$_{n11}NR^{11B}R^{11C}$, —$NHNR^{11B}R^{11C}$, —$ONR^{11B}R^{11C}$, —NHC(O)$NHNR^{11B}R^{11C}$. $R^2$ of the pharmaceutical compositions herein may be hydrogen, halogen, —$N_3$, —$CF_3$, —$CCl_3$, —$CBr_3$, —$CI_3$, —CN, —CHO, —$OR^{11A}$, or —$NO_2$. $R^2$ of the pharmaceutical compositions herein may be hydrogen. $R^2$ of the pharmaceutical compositions herein may be halogen. $R^2$ of the pharmaceutical compositions herein may be —$N_3$, —$CF_3$, —$CCl_3$, —$CBr_3$, —$CI_3$, —CN, —CHO, —$OR^{11A}$, or —$NO_2$. In embodiments, $R^2$ is not hydrogen. In embodiment $R^2$ is not halogen. In embodiments, $R^2$ is not $N_3$, —$CF_3$, —$CCl_3$, —$CBr_3$, —$CI_{13}$, —CN, —CHO, —$OR^{11A}$, or —$NO_2$.

$R^3$ is as described herein, including embodiments thereof. $R^3$ may be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ may be hydrogen.

$R^3$ may be substituted or unsubstituted alkyl. $R^3$ may be $R^{33}$-substituted or unsubstituted alkyl. $R^3$ may be unsubstituted alkyl. $R^3$ may be substituted or unsubstituted $C_1$-$C_{20}$ alkyl. $R^3$ may be $R^{33}$-substituted or unsubstituted $C_1$-$C_{20}$ alkyl. $R^3$ may be substituted or unsubstituted $C_1$-$C_{10}$ alkyl. $R^3$ may be $R^{33}$-substituted or unsubstituted $C_1$-$C_{10}$ alkyl. $R^3$ may be substituted or unsubstituted $C_1$-$C_5$ alkyl. $R^3$ may be $R^{33}$-substituted or unsubstituted $C_1$-$C_5$ alkyl.

$R^3$ may be substituted or unsubstituted heteroalkyl. $R^3$ may be unsubstituted heteroalkyl. $R^3$ may be substituted or unsubstituted 2 to 20 membered heteroalkyl. $R^3$ may be $R^{33}$-substituted or unsubstituted 2 to 20 membered heteroalkyl. $R^3$ may be substituted or unsubstituted 2 to 10 membered heteroalkyl. $R^3$ may be $R^{33}$-substituted or unsubstituted 2 to 10 membered heteroalkyl. $R^3$ may be substituted or unsubstituted 2 to 6 membered heteroalkyl. $R^3$ may be $R^{33}$-substituted or unsubstituted 2 to 6 membered heteroalkyl.

$R^3$ may be substituted or unsubstituted cycloalkyl. $R^3$ may be unsubstituted cycloalkyl. $R^3$ may be $R^{33}$-substituted or unsubstituted 3 to 20 membered cycloalkyl. $R^3$ may be substituted or unsubstituted 3 to 20 membered cycloalkyl. $R^3$ may be substituted or unsubstituted 3 to 10 membered cycloalkyl. $R^3$ may be $R^{33}$-substituted or unsubstituted 3 to 10 membered cycloalkyl. $R^3$ may be substituted or unsubstituted 3 to 6 membered cycloalkyl. $R^3$ may be $R^{33}$-substituted or unsubstituted 3 to 6 membered cycloalkyl.

$R^3$ may be substituted or unsubstituted heterocycloalkyl. $R^3$ may be unsubstituted heterocycloalkyl. $R^3$ may be substituted or unsubstituted 3 to 20 membered heterocycloalkyl. $R^3$ may be $R^{33}$-substituted or unsubstituted 3 to 20 membered heterocycloalkyl. $R^3$ may be substituted or unsubstituted 3 to 10 membered heterocycloalkyl. $R^3$ may be $R^{33}$-substituted or unsubstituted 3 to 10 membered heterocycloalkyl. $R^3$ may be substituted or unsubstituted 3 to 6 membered heterocycloalkyl. $R^3$ may be $R^{33}$-substituted or unsubstituted 3 to 6 membered heterocycloalkyl.

$R^3$ may be substituted or unsubstituted aryl. $R^3$ may be unsubstituted aryl. $R^3$ may be substituted or unsubstituted 5 to 10 membered aryl. $R^3$ may be $R^{33}$-substituted or unsubstituted 5 to 10 membered aryl. $R^3$ may be substituted or unsubstituted 5 to 3 membered aryl. $R^3$ may be $R^{33}$-substituted or unsubstituted 5 to 3 membered aryl. $R^3$ may be substituted or unsubstituted 6 membered aryl. $R^3$ may be $R^{33}$-substituted or unsubstituted 6 membered aryl.

$R^3$ may be substituted or unsubstituted heteroaryl. $R^3$ may be unsubstituted heteroaryl. $R^3$ may be substituted or unsubstituted 5 to 10 membered heteroaryl. $R^3$ may be $R^{33}$-substituted or unsubstituted 5 to 10 membered heteroaryl. $R^3$ may be substituted or unsubstituted 5 to 3 membered heteroaryl. $R^3$ may be $R^{33}$-substituted or unsubstituted 5 to 3 membered heteroaryl. $R^3$ may be substituted or unsubstituted 5 or 6 membered heteroaryl. $R^3$ may be $R^{33}$-substituted or unsubstituted 5 or 6 membered heteroaryl.

$R^{33}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

$R^{34}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl.

$R^{35}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^{4A}$ and $R^{4B}$ may independently be hydrogen, halogen, $-N_3$, $-CF_3$, $-CCl_3$, $-CBr_3$, $-CI_3$, $-CN$, $-CHO$, $-OR^{11A}$, $-NR^{11B}R^{11C}$, $-COOR^{11A}$, $-C(O)NR^{11B}R^{11C}$, $-NO_2$, $-SR^{11D}$, $-S(O)_{n111}R^{11B}$, $-S(O)_{n10}R^{11B}$, $-S(O)_{n11}NR^{11B}R^{11C}$, $-NHNR^{11B}R^{11C}$, $-ONR^{11B}R^{11C}$, $-NHC(O)NHNR^{11B}R^{11C}$. $R^{4A}$ and $R^{4B}$ may independently be hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{4A}$ is not hydrogen.

$R^{4A}$ and $R^{4B}$ may independently be substituted or unsubstituted alkyl. $R^{4A}$ and $R^{4B}$ may independently be $R^{36}$-substituted or unsubstituted alkyl. $R^{4A}$ and $R^{4B}$ may independently be unsubstituted alkyl. $R^{4A}$ and $R^{4B}$ may independently be substituted or unsubstituted $C_1$-$C_{20}$ alkyl. $R^{4A}$ and $R^{4B}$ may independently be $R^{36}$-substituted or unsubstituted $C_1$-$C_{20}$ alkyl. $R^3$ may independently be substituted or unsubstituted $C_1$-$C_{10}$ alkyl. $R^{4A}$ and $R^{4B}$ may independently be $R^{36}$-substituted or unsubstituted $C_1$-$C_{10}$ alkyl. $R^{4A}$ and $R^{4B}$ may independently be substituted or unsubstituted $C_1$-$C_5$ alkyl. $R^{4A}$ and $R^{4B}$ may independently be $R^{36}$-substituted or unsubstituted $C_1$-$C_5$ alkyl.

$R^{4A}$ and $R^{4B}$ may independently be substituted or unsubstituted heteroalkyl. $R^3$ may independently be unsubstituted heteroalkyl. $R^{4A}$ and $R^{4B}$ may independently be substituted or unsubstituted 2 to 20 membered heteroalkyl. $R^{4A}$ and $R^{4B}$ may independently be $R^{36}$-substituted or unsubstituted 2 to 20 membered heteroalkyl. $R^{4A}$ and $R^{4B}$ may independently be substituted or unsubstituted 2 to 10 membered heteroalkyl. $R^{4A}$ and $R^{4B}$ may independently be $R^{36}$-substituted or unsubstituted 2 to 10 membered heteroalkyl. $R^{4A}$ and $R^{4B}$ may independently be substituted or unsubstituted 2 to 6 membered heteroalkyl. $R^{4A}$ and $R^{4B}$ may independently be $R^{36}$-substituted or unsubstituted 2 to 6 membered heteroalkyl.

$R^{4A}$ and $R^{4B}$ may independently be substituted or unsubstituted cycloalkyl. $R^{4A}$ and $R^{4B}$ may independently be unsubstituted cycloalkyl. $R^{4A}$ and $R^{4B}$ may independently be $R^{36}$-substituted or unsubstituted 3 to 20 membered cycloalkyl. $R^{4A}$ and $R^{4B}$ may independently be substituted or unsubstituted 3 to 20 membered cycloalkyl. $R^{4A}$ and $R^{4B}$ may independently be substituted or unsubstituted 3 to 10 membered cycloalkyl. $R^{4A}$ and $R^{4B}$ may independently be $R^{36}$-substituted or unsubstituted 3 to 10 membered cycloalkyl. $R^{4A}$ and $R^{4B}$ may independently be substituted or unsubstituted 3 to 6 membered cycloalkyl. $R^{4A}$ and $R^{4B}$ may independently be $R^{36}$-substituted or unsubstituted 3 to 6 membered cycloalkyl.

$R^{4A}$ and $R^{4B}$ may independently be substituted or unsubstituted heterocycloalkyl. $R^{4A}$ and $R^{4B}$ may independently be unsubstituted heterocycloalkyl. $R^{4A}$ and $R^{4B}$ may independently be substituted or unsubstituted 3 to 20 membered heterocycloalkyl. $R^{4A}$ and $R^{4B}$ may independently be $R^{36}$-substituted or unsubstituted 3 to 20 membered heterocycloalkyl. $R^{4A}$ and $R^{4B}$ may independently be substituted or unsubstituted 3 to 10 membered heterocycloalkyl. $R^{4A}$ and $R^{4B}$ may independently be $R^{36}$-substituted or unsubstituted 3 to 10 membered heterocycloalkyl. $R^{4A}$ and $R^{4B}$ may independently be substituted or unsubstituted 3 to 6 membered heterocycloalkyl. $R^{4A}$ and $R^{4B}$ may independently be $R^{36}$-substituted or unsubstituted 3 to 6 membered heterocycloalkyl.

$R^{4A}$ and $R^{4B}$ may independently be substituted or unsubstituted aryl. $R^{4A}$ and $R^{4B}$ may independently be unsubstituted aryl. $R^{4A}$ and $R^{4B}$ may independently be substituted or unsubstituted 5 to 10 membered aryl. $R^{4A}$ and $R^{4B}$ may independently be $R^{36}$-substituted or unsubstituted 5 to 10 membered aryl. $R^{4A}$ and $R^{4B}$ may independently be substituted or unsubstituted 5 to 3 membered aryl. $R^{4A}$ and $R^{4B}$ may independently be $R^{36}$-substituted or unsubstituted 5 to 3 membered aryl. $R^{4A}$ and $R^{4B}$ may independently be substituted or unsubstituted 6 membered aryl. $R^{4A}$ and $R^{4B}$ may independently be $R^{36}$-substituted or unsubstituted 6 membered aryl.

$R^{4A}$ and $R^{4B}$ may independently be substituted or unsubstituted heteroaryl. $R^{4A}$ and $R^{4B}$ may independently be unsubstituted heteroaryl. $R^{4A}$ and $R^{4B}$ may independently be substituted or unsubstituted 5 to 10 membered heteroaryl. $R^{4A}$ and $R^{4B}$ may independently be $R^{36}$-substituted or unsubstituted 5 to 10 membered heteroaryl. $R^{4A}$ and $R^{4B}$ may independently be substituted or unsubstituted 5 to 3 membered heteroaryl. $R^{4A}$ and $R^{4B}$ may independently be $R^{36}$-substituted or unsubstituted 5 to 3 membered heteroaryl. $R^{4A}$ and $R^{4B}$ may independently be substituted or unsubstituted 5 or 6 membered heteroaryl. $R^{4A}$ and $R^{4B}$ may independently be $R^{36}$-substituted or unsubstituted 5 or 6 membered heteroaryl.

$R^{36}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

$R^{37}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl.

$R^{38}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^5$ is as described herein, including embodiments thereof. $R^5$ may be hydrogen, halogen, $-N_3$, $-CF_3$, $-CCl_3$, $-CBr_3$, $-CI_3$, $-CN$, $-CHO$, $-OR^{11A}$, $-NR^{11B}R^{11C}$, $-COOR^{11A}$, $-C(O)NR^{11B}R^{11C}$, $-NO_2$, $-SR^{11D}$, $-S(O)_{n11}R^{11B}$, $-S(O)_{n11}OR^{11B}$, $-S(O)_{n11}NR^{11B}R^{11C}$, $-NHNR^{11B}R^{11C}$, $-ONR^{11B}R^{11C}$, $-NHC(O)NHNR^{11B}R^{11C}$. $R^5$ may be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ may be hydrogen. $R^5$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ may be substituted or unsubstituted alkyl. $R^5$ may be $R^{39}$-substituted or unsubstituted alkyl. $R^5$ may be unsubstituted alkyl. $R^5$ may be substituted or unsubstituted $C_1$-$C_{20}$ alkyl. $R^5$ may be $R^{39}$-substituted or unsubstituted $C_1$-$C_{20}$ alkyl. $R^5$ may be substituted or unsubstituted $C_1$-$C_{10}$ alkyl. $R^5$ may be $R^{39}$-substituted or unsubstituted $C_1$-$C_{10}$ alkyl. $R^5$ may be substituted or unsubstituted $C_1$-$C_5$ alkyl. $R^5$ may be $R^{39}$-substituted or unsubstituted $C_1$-$C_5$ alkyl.

$R^5$ may be substituted or unsubstituted heteroalkyl. $R^5$ may be unsubstituted heteroalkyl. $R^5$ may be substituted or unsubstituted 2 to 20 membered heteroalkyl. $R^5$ may be $R^{39}$-substituted or unsubstituted 2 to 20 membered heteroalkyl. $R^5$ may be substituted or unsubstituted 2 to 10 membered heteroalkyl. $R^5$ may be $R^{39}$-substituted or unsubstituted 2 to 10 membered heteroalkyl. $R^5$ may be substituted or unsubstituted 2 to 6 membered heteroalkyl. $R^5$ may be $R^{39}$-substituted or unsubstituted 2 to 6 membered heteroalkyl.

$R^5$ may be substituted or unsubstituted cycloalkyl. $R^5$ may be unsubstituted cycloalkyl. $R^5$ may be $R^{39}$-substituted or unsubstituted 3 to 20 membered cycloalkyl. $R^5$ may be substituted or unsubstituted 3 to 20 membered cycloalkyl. $R^5$ may be substituted or unsubstituted 3 to 10 membered cycloalkyl. $R^5$ may be $R^{39}$-substituted or unsubstituted 3 to 10 membered cycloalkyl. $R^5$ may be substituted or unsubstituted 3 to 6 membered cycloalkyl. $R^5$ may be $R^{39}$-substituted or unsubstituted 3 to 6 membered cycloalkyl.

$R^5$ may be substituted or unsubstituted heterocycloalkyl. $R^5$ may be unsubstituted heterocycloalkyl. $R^5$ may be substituted or unsubstituted 3 to 20 membered heterocycloalkyl. $R^5$ may be $R^{39}$-substituted or unsubstituted 3 to 20 membered heterocycloalkyl. $R^5$ may be substituted or unsubstituted 3 to 10 membered heterocycloalkyl. $R^5$ may be $R^{39}$-substituted or unsubstituted 3 to 10 membered heterocycloalkyl. $R^5$ may be substituted or unsubstituted 3 to 6 membered heterocycloalkyl. $R^5$ may be $R^{39}$-substituted or unsubstituted 3 to 6 membered heterocycloalkyl.

$R^5$ may be substituted or unsubstituted aryl. $R^5$ may be unsubstituted aryl. $R^5$ may be substituted or unsubstituted 5 to 10 membered aryl. $R^5$ may be $R^{39}$-substituted or unsubstituted 5 to 10 membered aryl. $R^5$ may be substituted or unsubstituted 5 to 5 membered aryl. $R^5$ may be $R^{39}$-substituted or unsubstituted 5 to 3 membered aryl. $R^5$ may be substituted or unsubstituted 6 membered aryl. $R^5$ may be $R^{39}$-substituted or unsubstituted 6 membered aryl.

$R^5$ may be substituted or unsubstituted heteroaryl. $R^5$ may be unsubstituted heteroaryl. $R^5$ may be substituted or unsubstituted 5 to 10 membered heteroaryl. $R^5$ may be $R^{39}$-substituted or unsubstituted 5 to 10 membered heteroaryl. $R^5$ may be substituted or unsubstituted 5 to 3 membered heteroaryl. $R^5$ may be $R^{39}$-substituted or unsubstituted 5 to 3 membered heteroaryl. $R^5$ may be substituted or unsubstituted 5 or 6 membered heteroaryl. $R^5$ may be $R^{39}$-substituted or unsubstituted 5 or 6 membered heteroaryl.

$R^{39}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

$R^{40}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^{41}$ is halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^6$ is as described herein, including embodiments thereof. $R^6$ may be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ may be substituted or unsubstituted cycloalkyl, substituted or unsubstituted heterocycloalkyl, substituted or unsubstituted aryl, or substituted or unsubstituted heteroaryl.

$R^6$ may be substituted or unsubstituted cycloalkyl. $R^6$ may be unsubstituted cycloalkyl. $R^6$ may be $R^{23}$-substituted or unsubstituted 3 to 20 membered cycloalkyl. $R^6$ may be substituted or unsubstituted 3 to 20 membered cycloalkyl. $R^6$ may be substituted or unsubstituted 3 to 10 membered cycloalkyl. $R^6$ may be $R^{23}$-substituted or unsubstituted 3 to 10 membered cycloalkyl. $R^6$ may be substituted or unsubstituted 3 to 6 membered cycloalkyl. $R^6$ may be $R^{23}$-substituted or unsubstituted 3 to 6 membered cycloalkyl.

$R^6$ may be substituted or unsubstituted heterocycloalkyl. $R^6$ may be unsubstituted heterocycloalkyl. $R^6$ may be substituted or unsubstituted 3 to 20 membered heterocycloalkyl. $R^6$ may be $R^{23}$-substituted or unsubstituted 3 to 20 membered heterocycloalkyl. $R^6$ may be substituted or unsubstituted 3 to 10 membered heterocycloalkyl. $R^6$ may be $R^{23}$-substituted or unsubstituted 3 to 10 membered heterocycloalkyl. $R^6$ may be substituted or unsubstituted 3 to 6 membered heterocycloalkyl. $R^6$ may be $R^{23}$-substituted or unsubstituted 3 to 6 membered heterocycloalkyl.

$R^6$ may be substituted or unsubstituted aryl. $R^6$ may be unsubstituted aryl. $R^6$ may be substituted or unsubstituted 5 to 10 membered aryl. $R^6$ may be $R^{23}$-substituted or unsubstituted 5 to 10 membered aryl. $R^6$ may be substituted or unsubstituted 5 to 5 membered aryl. $R^6$ may be $R^{23}$-substituted or unsubstituted 5 to 3 membered aryl. $R^6$ may be substituted or unsubstituted 6 membered aryl. $R^6$ may be $R^{23}$-substituted or unsubstituted 6 membered aryl.

$R^6$ may be substituted or unsubstituted heteroaryl. $R^6$ may be unsubstituted heteroaryl. $R^6$ may be substituted or unsubstituted 5 to 10 membered heteroaryl. $R^6$ may be $R^{23}$-substituted or unsubstituted 5 to 10 membered heteroaryl. $R^6$ may be substituted or unsubstituted 5 to 3 membered heteroaryl. $R^6$ may be $R^{23}$-substituted or unsubstituted 5 to 3 membered heteroaryl. $R^6$ may be substituted or unsubstituted 5 or 6 membered heteroaryl. $R^6$ may be $R^{23}$-substituted or unsubstituted 5 or 6 membered heteroaryl.

$R^{23}$ is as described herein, including embodiments thereof.

$R^7$, $R^8$, $R^{9A}$, $R^{9B}$, and $R^{9C}$, are as described herein, including embodiments thereof.

The symbol n11 may be 1. The symbol n11 may be 2. The symbol z1 and z2 are as described herein, including embodiments thereof. $R^{11A}$, $R^{11B}$, $R^{11}$, and $R^{11D}$ may independently hydrogen, substituted or unsubstituted alkyl, or unsubstituted aryl. In embodiments, the pharmaceutical composition includes a compound of formula (I), (II), or (III), including embodiments thereof and optionally a pharmaceutically acceptable excipient as described herein. In embodiments, pharmaceutical composition includes a compound as described herein (e.g., a compound described in another aspect or embodiment herein, for example, in a compound aspect or embodiment or in a method aspect or embodiment), including embodiments thereof (e.g. formula (I), (II), or (III) or formula 4a, 4b, 4c, 4d, 4e, 4f, 4g, 4h, 4i, 4j, 4k, 4l, 4m, 4n, 4o, 4p, 4q, 4r, 4s, 8-1, 8-2, 8-3, 9-1, 9-2, 9-3, Z533, Z201, Z380, Z254, Z991, E7, Z993, Z990, Z098, Z992, Z047, Z873, or Z26476908). The pharmaceutical composition may optionally include a pharmaceutically acceptable excipient as described herein.

In another aspect is a method of treating metabolic disease in a subject in need thereof. The method includes administering to the subject in need thereof, a compound described herein, including for example a compound of formula:

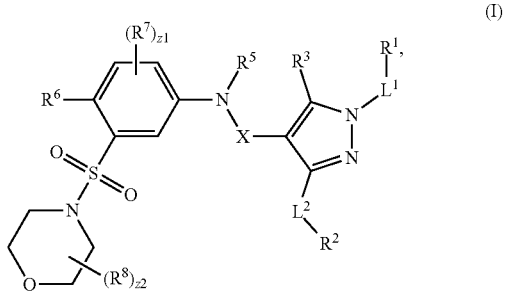

including pharmaceutically acceptable salts and pharmaceutically acceptable compositions (as described herein, including all its embodiments) thereof.

X, Y, $L^1$, $L^2$, z1, z2, n, n3, n6, n7, n8, n10, n11, $R^1$, $R^2$, $R^3$, $R^{4A}$, $R^{4B}$, $R^5$, $R^6$, R, $R^8$, $R^{9A}$, $R^{9B}$, $R^{9C}$, $R^{10}$, $R^{10A}$, $R^{10B}$, $R^{10C}$, $R^{10D}$, $R^{11}$, $R^{11A}$, $R^{11B}$, $R^{11C}$, and $R^{11D}$, are as described herein, including embodiments thereof. In embodiments, the method includes administering a pharmaceutically composition as described herein, including embodiments thereof. In embodiments, a compound used in the method is a compound described herein (e.g., a compound described in another aspect or embodiment herein, for example, in a compound aspect or embodiment or a pharmaceutical composition aspect or embodiment or in another method aspect or embodiment).

In embodiments, $R^1$ and $R^2$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, X is —$CH_2$— or —C(O)—, and $R^5$ is hydrogen or substituted or unsubstituted alkyl. In a further embodiment, $R^6$ is substituted or unsubstituted $C_1$-$C_5$ alkyl as described herein, including embodiments thereof.

The compound of the method of treating may have formula (II) as described herein, including embodiments thereof. X, $R^1$, $R^2$, $R^3$, $R^5$, $R^6$ are as described herein, including embodiments thereof.

In embodiments, $R^1$ is $R^{10}$-substituted or unsubstituted alkyl, $R^{10}$-substituted or unsubstituted cycloalkyl, or $R^{10}$-substituted or unsubstituted aryl, wherein $R^{10}$ is independently halogen, —$N_3$, —$CF_3$, —$CCl_3$, —$CBr_3$, —$CI_3$, —CN, —CHO, —$OR^{10A}$, —$NR^{11B}R^{10C}$, —$COOR^{10A}$, —C(O)$NR^{10B}R^{10C}$, —$NO_2$, —$SR^{10D}$, —S(O)$_{n10}R^{10B}$, —S(O)$_{n10}OR^{10B}$, —S(O)$_{n10}NR^{10B}R^{10C}$, —$NHNR^{10B}R^{10C}$, —$ONR^{10B}R^{10C}$, —NHC(O)$NHNR^{10B}R^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10A}$, $R^{10B}$, $R^{10C}$, $R^{10D}$ and n10 are as described herein, including embodiments thereof.

In embodiments, $R^1$ is $R^{10}$-substituted or unsubstituted alkyl, unsubstituted cycloalkyl, or $R^{10}$-substituted or unsubstituted aryl. $R^{10}$ may hydrogen, halogen, $CF_3$, $OR^{10}$A. $R^{10A}$ may be hydrogen or unsubstituted $C_1$-$C_5$ alkyl.

In embodiments, $R^2$ is $R^{17}$-substituted or unsubstituted alkyl or $R^{17}$-substituted or unsubstituted aryl. $R^{17}$ may be halogen, —$CF_3$, —$OR^{17A}$. $R^{17}$ may be halogen. $R^{17}$ may be —$CF_3$. $R^{17}$ may be —$OR^{17A}$. $R^{17A}$ may be hydrogen or unsubstituted $C_1$-$C_5$ alkyl. In embodiments, X is —C(O)—. $R^2$ may be $R^{17}$-substituted or unsubstituted alkyl, or $R^{17}$-substituted or unsubstituted aryl, where $R^{17}$ is —$CF_3$, OR$^{17A}$. R$^{17A}$ may be hydrogen or unsubstituted C$_1$-C$_5$ alkyl. In embodiments, R$^2$ is R$^{17}$-substituted or unsubstituted aryl, where R$^{17}$ is R$^{18}$-substituted or unsubstituted alkyl (e.g. C$_1$-C$_5$ alkyl), —OR$^{17A}$, or —CF$_3$. R$^{17A}$ may be hydrogen or substituted or unsubstituted alkyl (e.g. C$_1$-C$_5$ alkyl). R$^{17}$ may be methyl. R$^{17A}$ may be methyl.

In embodiments, R$^2$ is R$^{17}$-substituted or unsubstituted alkyl or R$^{17}$-substituted or unsubstituted aryl and R$^1$ is R$^{10}$-substituted or unsubstituted alkyl, unsubstituted cycloalkyl, or R$^{10}$-substituted or unsubstituted aryl. R$^{17}$ and R$^{10}$ are as described herein, including embodiments thereof. L$^1$ and L$^2$ may independently be a bond, —C(O)—, substituted or unsubstituted alkylene, substituted or unsubstituted heteroarylene, or substituted or unsubstituted arylene. In embodiments, L$^1$ and L$^2$ are a bond. L$^1$ and L$^2$ are substituted or unsubstituted alkylene. In embodiments, L$^1$ is substituted or unsubstituted alkylene and L$^2$ is a bond.

In embodiments, the compound of the method has formula:

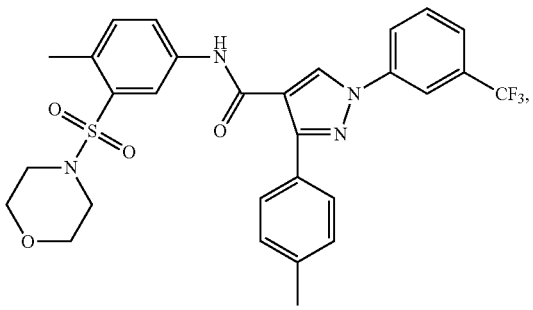

(4a)

(4b)

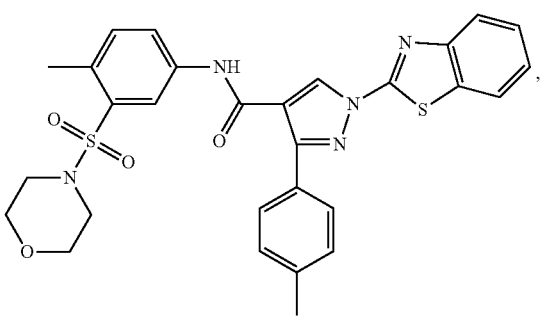

(4c)

-continued (4d)

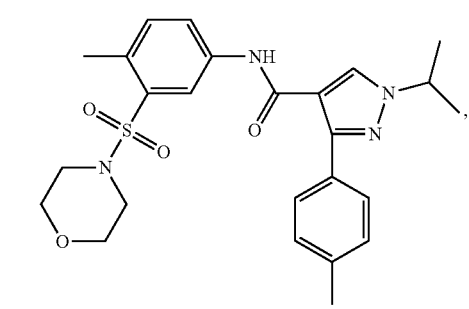

(4e)

(4f)

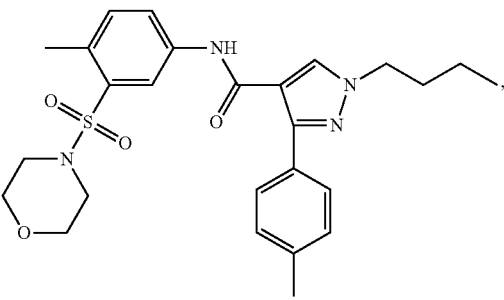

(4g)

(4h)

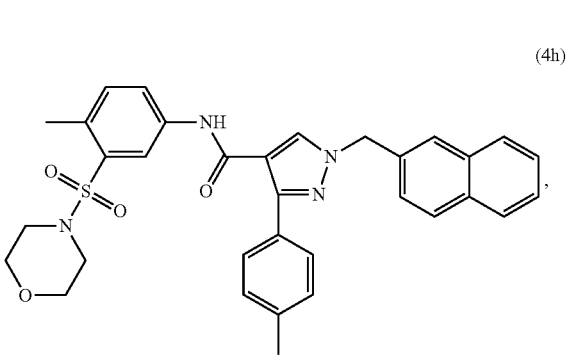

(4i)
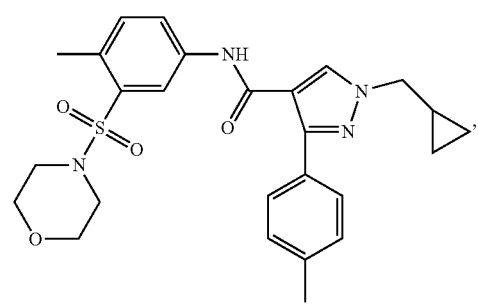
(4j)
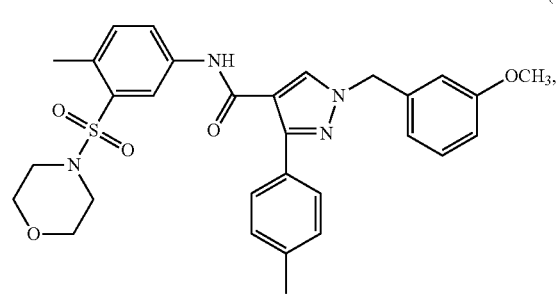
(4k)
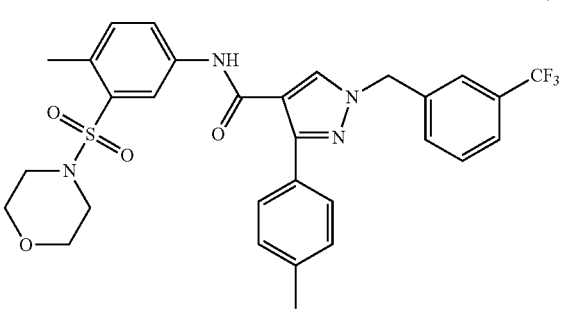
(4l)
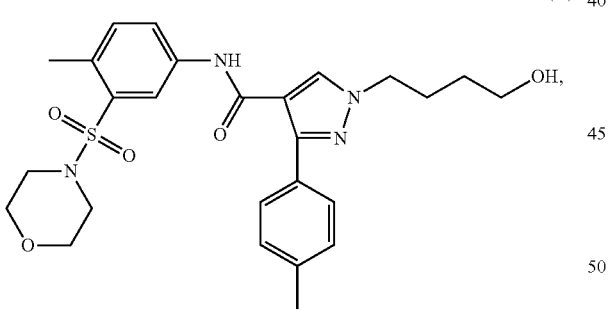
(4m)
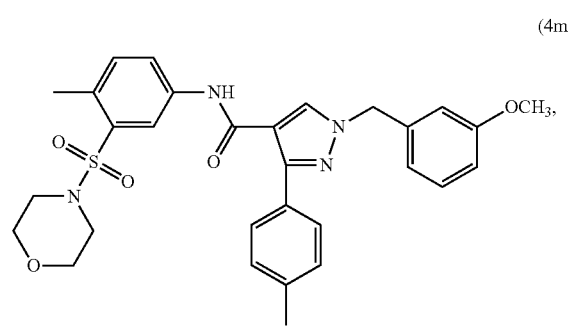
(4n)
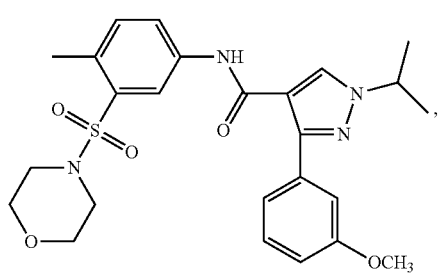
(4o)
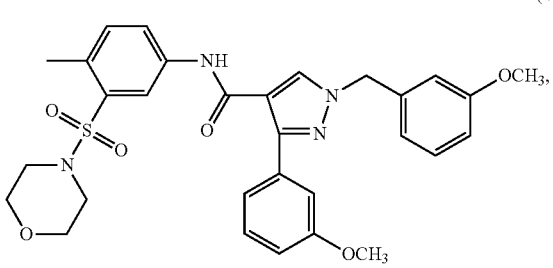
(4p)
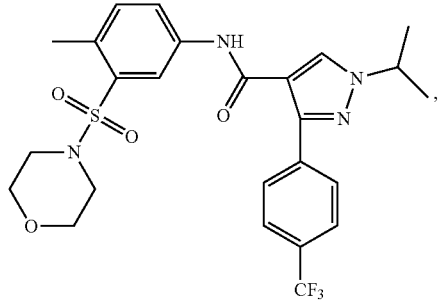
(4q)
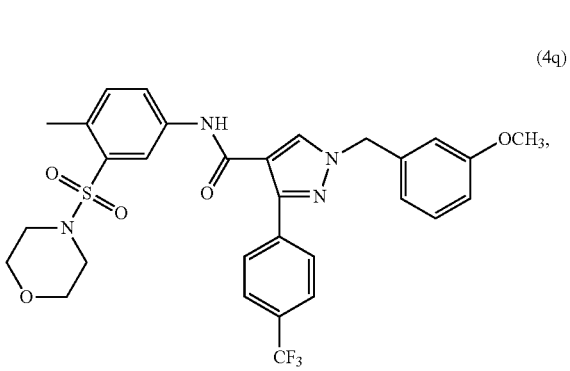
(4r)
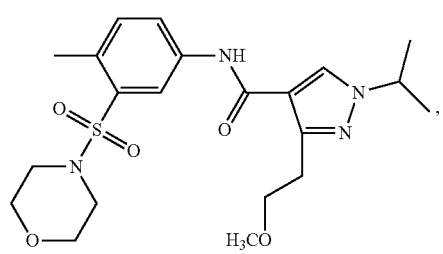

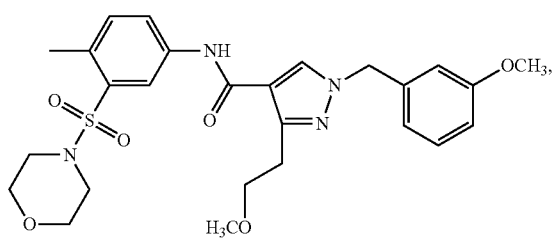
(4s)
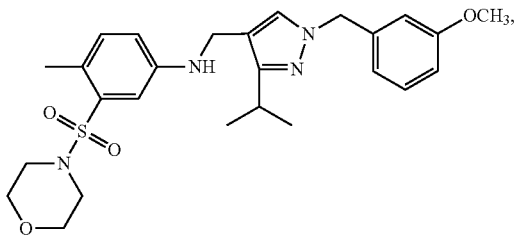
(9-2)
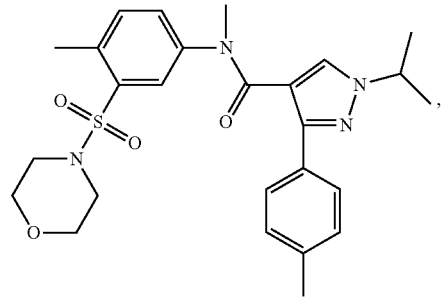
(8-1)
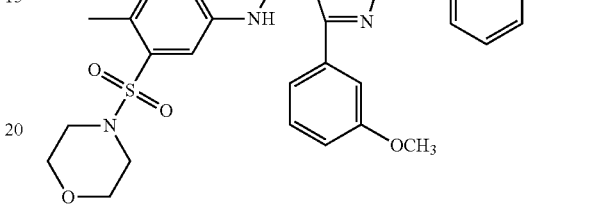
(9-3)
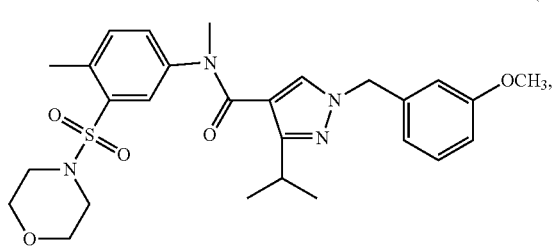
(8-2)
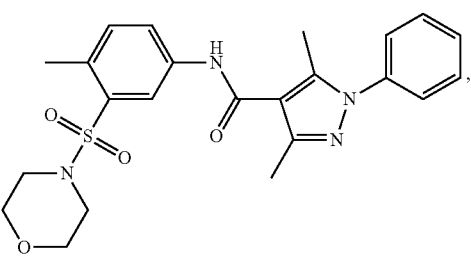
(Z533)
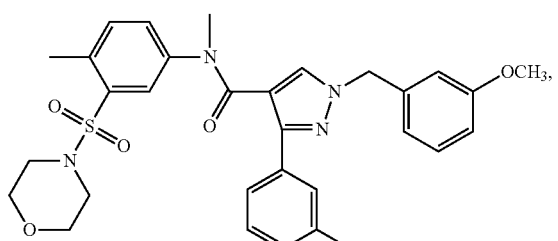
(8-3)
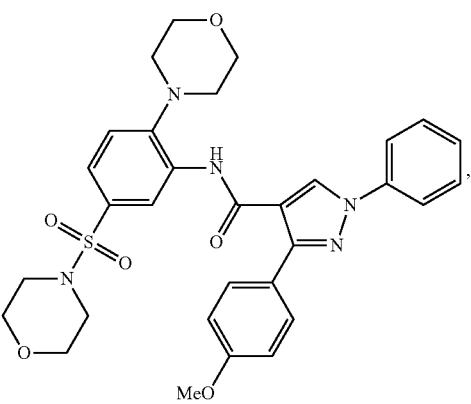
(Z201)
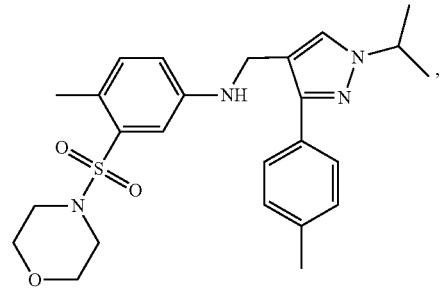
(9-1)
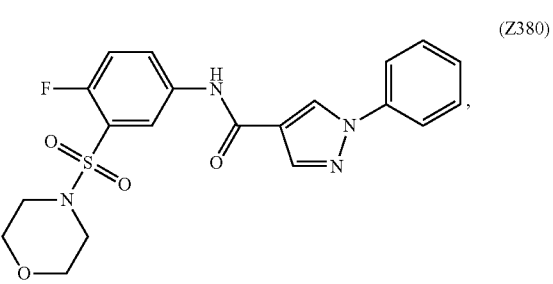
(Z380)

-continued

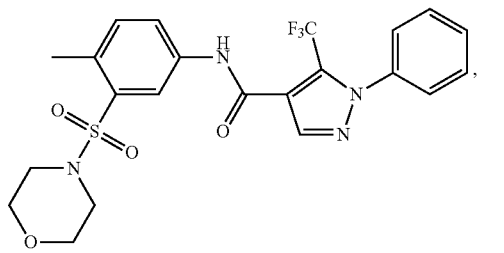
(Z254)

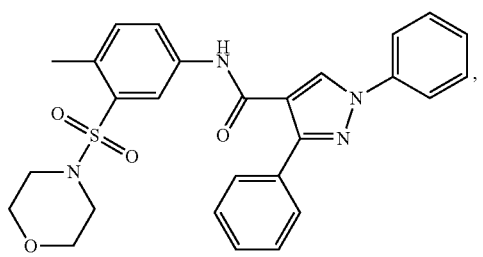
(Z991)

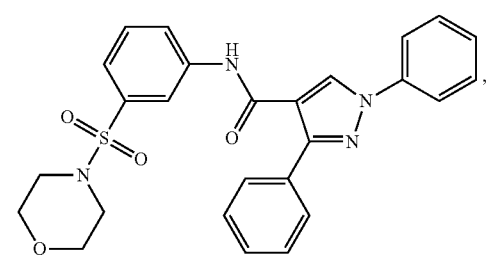
(E7)

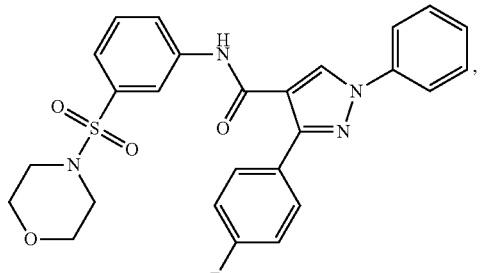
(Z993)

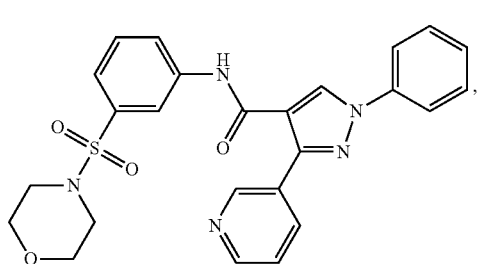
(Z990)

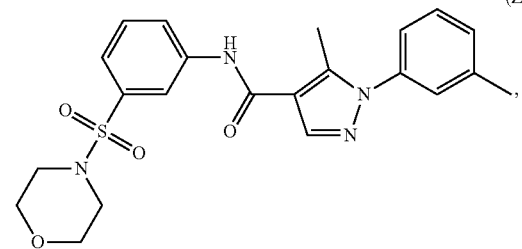
(Z098)

-continued

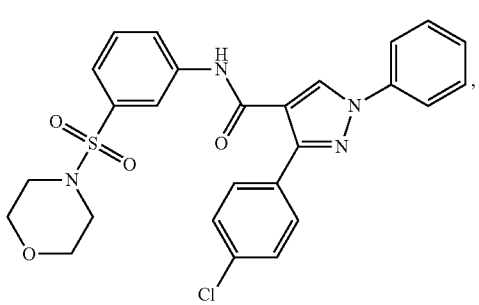
(Z992)

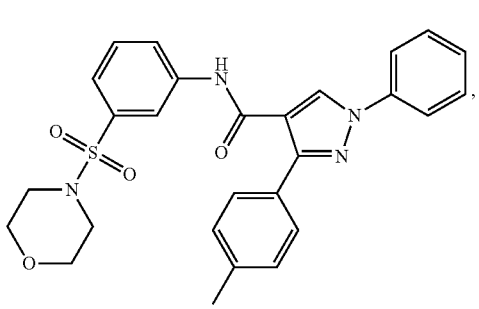
(Z047)

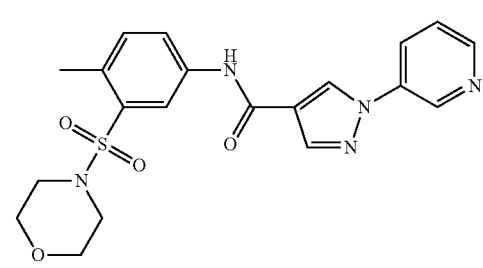
(Z873) or

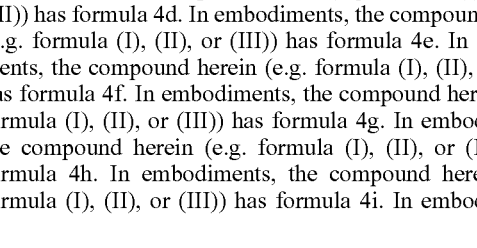
(Z26476908)

In embodiments, the compound herein (e.g. formula (I), (II), or (III)) has formula 4a, 4b, 4c, 4d, 4e, 4f, 4g, 4h, 4i, 4j, 4k, 4l, 4m, 4n, 4o, 4p, 4q, 4r, 4s, 8-1, 8-2, 8-3, 9-1, 9-2, 9-3, Z533, Z201, Z380, Z254, Z991, E7, Z993, Z990, Z098, Z992, Z047, Z873, or Z26476908. In embodiments, the compound herein (e.g. formula (I), (II), or (III)) has formula 4a. In embodiments, the compound herein (e.g. formula (I), (II), or (III)) has formula 4b. In embodiments, the compound herein (e.g. formula (I), (II), or (III)) has formula 4c. In embodiments, the compound herein (e.g. formula (I), (II), or (III)) has formula 4d. In embodiments, the compound herein (e.g. formula (I), (II), or (III)) has formula 4e. In embodiments, the compound herein (e.g. formula (I), (II), or (III)) has formula 4f. In embodiments, the compound herein (e.g. formula (I), (II), or (III)) has formula 4g. In embodiments, the compound herein (e.g. formula (I), (II), or (III)) has formula 4h. In embodiments, the compound herein (e.g. formula (I), (II), or (III)) has formula 4i. In embodiments, the compound herein (e.g. formula (I), (II), or (III)) has formula 4j. In embodiments, the compound herein (e.g. formula (I), (II), or (III)) has formula 4k. In embodiments, the compound herein (e.g. formula (I), (II), or (III)) has formula 4l. In embodiments, the compound herein (e.g. formula (I), (II), or (III)) has formula 4m. In embodiments, the compound herein (e.g. formula (I), (II), or (III)) has formula 4n. In embodiments, the compound herein (e.g. formula (I), (II), or (III)) has formula 4o. In embodiments, the compound herein (e.g. formula (I), (II), or (III)) has formula 4p. In embodiments, the compound herein (e.g. formula (I), (II), or (III)) has formula 4q. In embodiments, the compound herein (e.g. formula (I), (II), or (III)) has formula 4r. In embodiments, the compound herein (e.g. formula (I), (II), or (III)) has formula 4s. In embodiments, the compound herein (e.g. formula (I), (II), or (III)) has formula 8-1. In embodiments, the compound herein (e.g. formula (I), (II), or (III)) has formula 8-2. In embodiments, the compound herein (e.g. formula (I), (II), or (III)) has formula 8-3. In embodiments, the compound herein (e.g. formula (I), (II), or (III)) has formula 9-1. In embodiments, the compound herein (e.g. formula (I), (II), or (III)) has formula 9-2. In embodiments, the compound herein (e.g. formula (I), (II), or (III)) has formula 9-3. In embodiments, the compound herein (e.g. formula (I), (II), or (III)) has formula Z533. In embodiments, the compound herein (e.g. formula (I), (II), or (III)) has formula Z201. In embodiments, the compound herein (e.g. formula (I), (II), or (III)) has formula Z380. In embodiments, the compound herein (e.g. formula (I), (II), or (III)) has formula Z254. In embodiments, the compound herein (e.g. formula (I), (II), or (III)) has formula Z991. In embodiments, the compound herein (e.g. formula (I), (II), or (III)) has formula E7. In embodiments, the compound herein (e.g. formula (I), (II), or (III)) has formula Z993. In embodiments, the compound herein (e.g. formula (I), (II), or (III)) has formula Z990. In embodiments, the compound herein (e.g. formula (I), (II), or (III)) has formula Z098. In embodiments, the compound herein (e.g. formula (I), (II), or (III)) has formula Z992. In embodiments, the compound herein (e.g. formula (I), (II), or (III)) has formula Z047. In embodiments, the compound herein (e.g. formula (I), (II), or (III)) has formula Z873. In embodiments, the compound herein (e.g. formula (I), (II), or (III)) has formula Z26476908.

The metabolic disease may be dyslipidemia, insulin-resistance, increased blood pressure, visceral obesity, cholestasis, or hypercoagubility. The metabolic disease may be dyslipidemia. The metabolic disease may be insulin-resistance. The metabolic disease may be increased blood pressure. The metabolic disease may be visceral obesity. The metabolic disease may be cholestasis. The metabolic disease may be hypercoagubility. In embodiments, the metabolic diseases includes at least one of dyslipidemia, insulin-resistance, increased blood pressure, visceral obesity, cholestasis, or hypercoagubility. In embodiments, the metabolic disease includes at least cholestasis or at least dyslipidemia. In embodiments the dyslipidemia is hypertriglyceridemia.

In another aspect is provided a method of antagonizing an FXR protein. The method includes contacting an FXR protein with a compound disclosed herein (e.g. formula (I), (II), or (III)), thereby antagonizing the FXR protein.

In embodiments, X, Y, $L^1$, $L^2$, z1, z2, n, n3, n6, n7, n8, n10, n11, $R^1$, $R^2$, $R^3$, $R^{4A}$, $R^{4B}$, $R^5$, $R^6$, $R^7$, $R^8$, $R^{9A}$, $R^{9B}$, $R^{9C}$, $R^{10}$, $R^{10A}$, $R^{10B}$, $R^{10C}$, ROD, $R^{11}$, $R^{11A}$, $R^{11B}$, $R^{11C}$, and $R^{11D}$, are as described herein, including embodiments thereof. In embodiments, the method includes administering a pharmaceutically composition as described herein, including embodiments thereof. In embodiments, a compound disclosed herein is a compound described herein (e.g., a compound described in another aspect or embodiment herein, for example, in a compound aspect or embodiment or a pharmaceutical composition aspect or embodiment or in another method aspect or embodiment).

ADDITIONAL EMBODIMENTS

1. A compound having the formula:

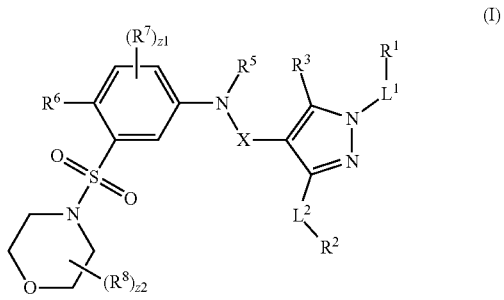

(I) wherein, X is —$CH_2$— or —C(O)— or —CY(OH)—; Y is hydrogen, halogen, —$N_3$, —$NO_2$, —$CF_3$, —$CCl_3$, —$CBr_3$, —$CI_3$, —CN, —$OR^{9A}$, —$NHR^{9A}$, —$COOR^{9A}$, —$CONHR^{9A}$, —SH, —$SO_3H$, —$SO_4H$, —$SO_2NH_2$, —$NHNH_2$, —$ONH_2$, —$OCH_3$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^1$ is independently a bond, —C(O)—, —C(O)—O, —O—, —S—, —$NR^{9B}$—, —$C(O)NR^{9B}$—, —$S(O)_n$—, —$S(O)NR^{9B}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^2$ is independently a bond, —C(O)—, —C(O)—O, —O—, —S—, —$NR^{9C}$—, —$C(O)NR^{9C}$—, —$S(O)_n$—, —$S(O)NR^{9C}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ and $R^2$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$, —$COOR^{3A}$, —$C(O)NR^{3B}R^{3C}$, —$NO_2$, —$SR^{3D}$, —$S(O)_{n3}R^{3B}$, —$S(O)_{n3}OR^{3B}$, —$S(O)_{n3}NR^{3B}R^{3C}$, —$NHNR^{3B}R^{3C}$, —$ONR^{3B}R^{3C}$, —$NHC(O)NHNR^{3B}R^{3C}$, or substituted or unsubstituted alkyl, $R^5$ is hydrogen or substituted or unsubstituted alkyl; $R^6$ is halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{n60}R^{6B}$, —$SO_{n6}NR^{6B}R^{6C}$, —$NHNR^{6B}R^{6C}$, —$ONR^{6B}R^{6C}$, —$NHC(O)NHNR^{6B}R^{6C}$, substituted or unsubstituted alkyl, or substituted or unsubstituted heteroalkyl; $R^7$ is independently hydrogen, halogen, —$N_3$, —$CF_3$, —$CCl_3$, —$CBr_3$, —$CI_3$, —CN, —CHO, —$OR^{7A}$, —$NR^{7B}R^{7C}$, —$COOR^{7A}$, —$C(O)NR^{7B}R^{7C}$, —NO₂, —SR^{7D}, —S(O)_{n7}R^{7B}, —S(O)_{n7}OR^{7B}, —S(O)_{n7}NR^{7B}R^{7C}, —NHNR^{7B}R^{7C}, —ONR^{7B}R^{7D}, —NHC(O)NHNR^{7B}R^{7C}, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R⁸ is independently hydrogen, halogen, —N₃, —CF₃, —CCl₃, —CBr₃, —CI₃, —CN, —CHO, —OR^{8A}, —NR^{8B}R^{8C}, —COOR^{8A}, —C(O)NR^{8B}R^{8C}, —NO₂, —SR^{8D}, —S(O)_{n8}R^{8B}, —S(O)_{n8}OR^{8B}, —S(O)_{n8}NR^{8B}R^{8C}, —NHNR^{8B}R^{8C}, —ONR^{8B}R^{8C}, —NHC(O)NHNR^{8B}R^{8C}, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R^{9A}, R^{9B}, R^{9C} are independently hydrogen, halogen, —N₃, —NO₂, —CF₃, —CCl₃, —CBr₃, —CI₃, —CN, —OH, —NH₂, —COOH, —CONH₂, —SH, —SO₃H, —SO₄H, —SO₂NH₂, —NHNH₂, —ONH₂, —OCH₃, —NHC(O)NHNH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R^{3A}, R^{6A}, R^{7A}, and R^{8A} are independently hydrogen or unsubstituted alkyl; R^{3B}, R^{6B}, R^{7B}, R^{8B}, R^{3C}, R^{6C}, R^{7C}, R^{8C}, R^{3D}, R^{6D}, R^{7D}, and R^{8D} are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z1 is 1, 2, 3, 4, 5 or 6; z2 is 1, 2, 3, 4, 5, 6, 7 or 8; n, n3, n6, n7, and n8 are independently 1 or 2; and wherein if X is —C(O)— and -L¹-R¹ is unsubstituted phenyl, then -L²-R² is not methyl, p-substituted or unsubstituted phenyl, or unsubstituted pyridine.

2. The compound of embodiment, wherein R⁶ is substituted or unsubstituted C₁-C₅ alkyl.

3. The compound of embodiment 1 or 2, wherein X is —C(O)—.

4. The compound of any one of embodiments 1 to 3, wherein L¹ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

5. The compound of any one of embodiments 1 to 4, wherein L¹ is substituted or unsubstituted C₁-C₅ alkylene.

6. The compound of any one of embodiments 1 to 5, wherein L² is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

7. The compound of any one of embodiments 1 to 6, wherein L² is a bond or substituted or unsubstituted alkylene.

8. The compound of any one of embodiments 1 to 7, wherein R¹ is unsubstituted cycloalkyl, substituted or unsubstituted heterocycloalkyl, or substituted or unsubstituted aryl.

9. The compound of embodiment 1, having formula:

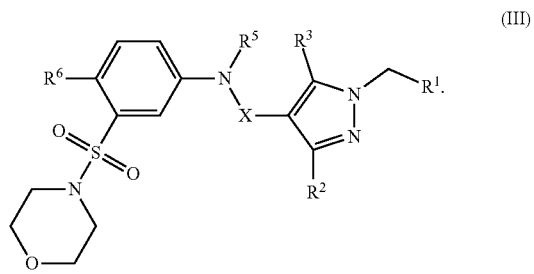

(III)

10. The compound of embodiment 9, wherein R¹ is R¹⁰-substituted or unsubstituted alkyl, R¹⁰-substituted or unsubstituted cycloalkyl, or R¹⁰-substituted or unsubstituted aryl, wherein R¹⁰ is independently hydrogen, halogen, —N₃, —CF₃, —CCl₃, —CBr₃, —CI₃, —CN, —CHO, —OR^{10A}, —NR^{10B}R^{10C}, —COOR^{10A}, —C(O)NR^{10B}R^{10C}, —NO₂, —SR^{10D}, —S(O)_{n10}R^{10B}, —S(O)_{n10}OR^{10B}, —S(O)_{n10}NR^{10B}R^{10C}, —NHNR^{10B}R^{10C}, —ONR^{10B}R^{10C}, —NHC(O)NHNR^{10B}R^{10C}, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R^{10A}, R^{10B}, R^{10C}, and R^{10D} are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n10 is 1 or 2.

11. The compound of embodiment 9 or 10, wherein R¹ is R¹⁰-substituted or unsubstituted alkyl, unsubstituted cycloalkyl, or R¹⁰-substituted or unsubstituted aryl; R¹⁰ is hydrogen, halogen, CF₃, OR¹⁰A; and R^{10A} is hydrogen or unsubstituted C₁-C₅ alkyl.

12. The compound of embodiment 1 having formula:

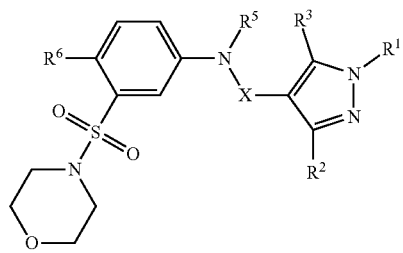

(II).

13. The compound of embodiment 12, wherein R¹ is substituted or unsubstituted alkyl, substituted or unsubstituted aryl or substituted or unsubstituted heteroaryl.

14. The compound of embodiment 12 or 13, wherein R¹ is R¹⁰-substituted or unsubstituted alkyl, R¹⁰-substituted or unsubstituted aryl, or R¹⁰-substituted or unsubstituted heteroaryl, wherein R¹⁰ is independently halogen, —N₃, —CF₃, —CCl₃, —CBr₃, —CI₃, —CN, —CHO, —OR^{10A}, substituted or unsubstituted alkyl, substituted or unsubstituted heteroalkyl, substituted or unsubstituted aryl, or substituted or unsubstituted heteroaryl; and R^{10A} is independently hydrogen or substituted or unsubstituted alkyl.

15. The compound of any one of embodiments 12 to 14, wherein R¹ is R¹⁰-substituted or unsubstituted alkyl, R¹⁰-substituted or unsubstituted aryl, or R¹⁰-substituted or unsubstituted heteroaryl; R¹⁰ is halogen, —CF₃, OR^{10A}, substituted or unsubstituted $C_1$-$C_5$ alkyl, or substituted or unsubstituted aryl; and $R^{10A}$ is hydrogen or methyl.

16. The compound of any one of embodiments 1 to 15, wherein $R^2$ is hydrogen, substituted or unsubstituted alkyl, substituted or unsubstituted aryl, or substituted or unsubstituted heteroaryl.

17. The compound of any one of embodiments 1 to 16, wherein $R^2$ is hydrogen, $R^{17}$-substituted or unsubstituted alkyl or $R^{17}$-substituted or unsubstituted aryl, wherein $R^{17}$ is independently halogen, —$N_3$, —$CF_3$, —$CCl_3$, —$CBr_3$, —$CI_3$, —CN, —CHO, —$OR^{17A}$, —$NR^{17B}R^{17C}$, —$COOR^{17A}$, —$C(O)NR^{17B}R^{17C}$, —$NO_2$, —$SR^{17D}$, —$S(O)_{n17}R^{7B}$, —$S(O)_{n17}OR^{17B}$, —$S(O)_{n17}NR^{17B}R^{17C}$, —$NHNR^{17B}R^{7C}$, —$ONR^{17B}R^{17C}$, —NHC(O)NHNR$^{17B}R^{17C}$, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl; $R^{17A}$, $R^{17B}$, $R^{17C}$, and $R^{17D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n17 is 1 or 2.

18. The compound of any one of embodiments 1 to 17, wherein $R^2$ is hydrogen, $R^{17}$-substituted or unsubstituted alkyl, $R^{17}$-substituted or unsubstituted aryl, or $R^{17}$-substituted or unsubstituted heteroaryl; $R^{17}$ is substituted or unsubstituted alkyl, halogen, —$CF_3$, —$OR^{17A}$; and $R^{17A}$ is hydrogen or unsubstituted $C_1$-$C_5$ alkyl.

19. The compound of any one of embodiments 1 to 18, wherein $R^3$ is hydrogen, halogen, —$N_3$, —$CF_3$, —$CCl_3$, —$CBr_3$, —$CI_3$, —CN, —CHO, —$OR^{3A}$, or substituted or unsubstituted alkyl, wherein $R^{3A}$ is hydrogen or unsubstituted $C_1$-$C_5$ alkyl.

20. The compound of any one of embodiments 1 to 19, wherein $R^3$ is hydrogen, halogen, —$CF_3$, —OH, or substituted or unsubstituted alkyl.

21. The compound of any one of embodiments 1 to 20, wherein $R^5$ is hydrogen or methyl.

22. The compound of any one of embodiments 1 to 21, wherein $R^7$ and $R^8$ are independently hydrogen, halogen, —$N_3$, —$CF_3$, —$CCl_3$, —$CBr_3$, —$CI_3$, —CN, —CHO, —OH, —$OCH_3$, or substituted or unsubstituted alkyl.

23. The compound of any one of embodiments 1 to 22, having the formula:

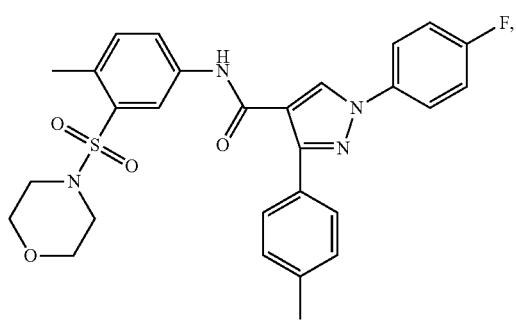

-continued

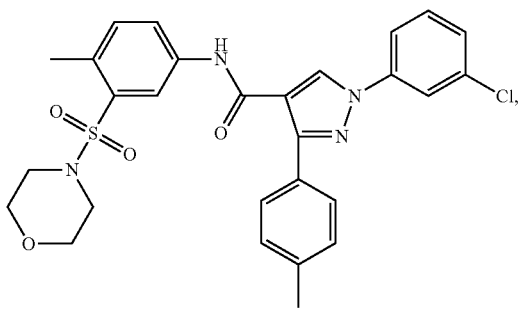

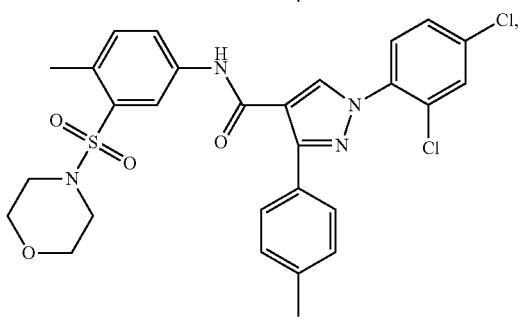

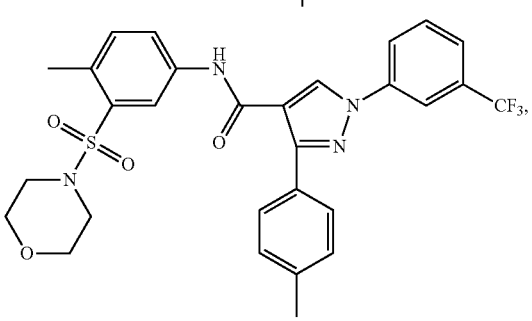

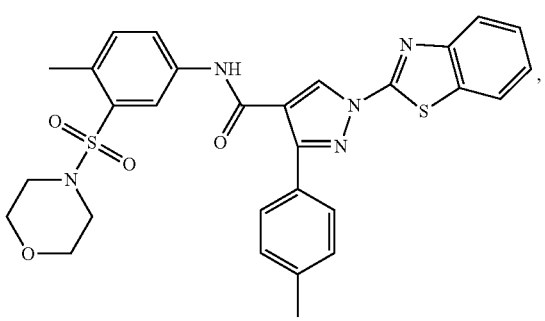

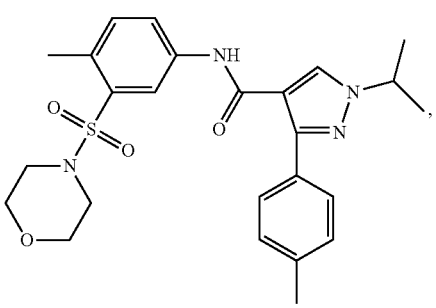

63
-continued
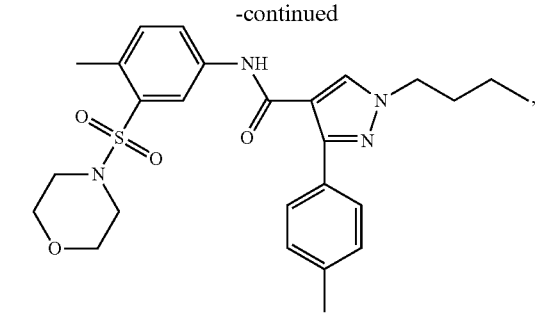
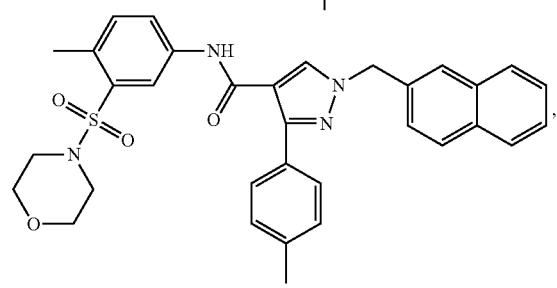
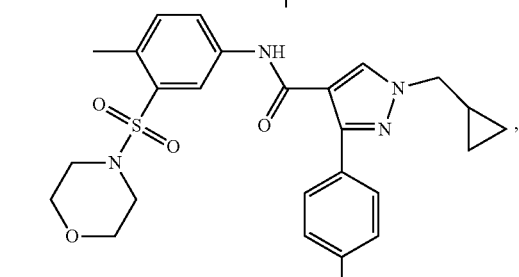
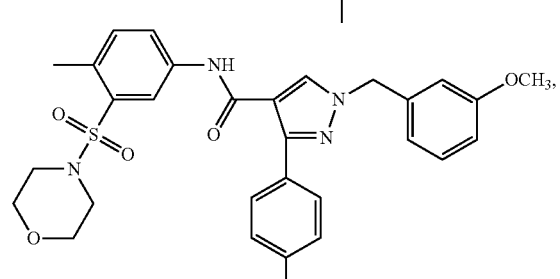
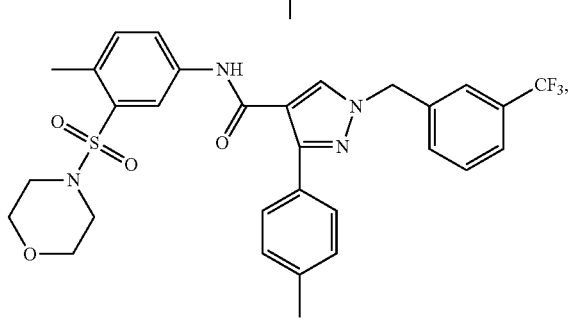
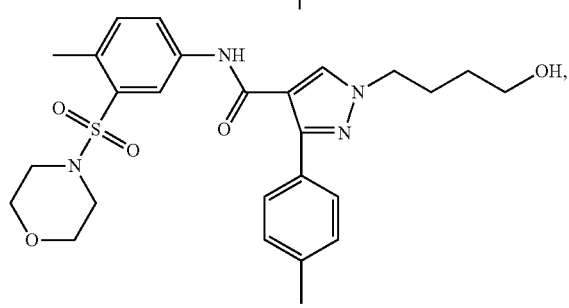
64
-continued
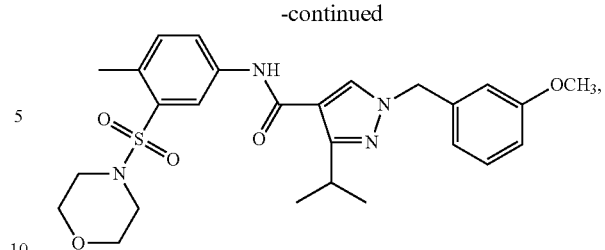
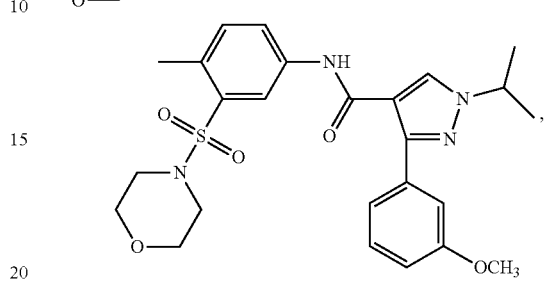
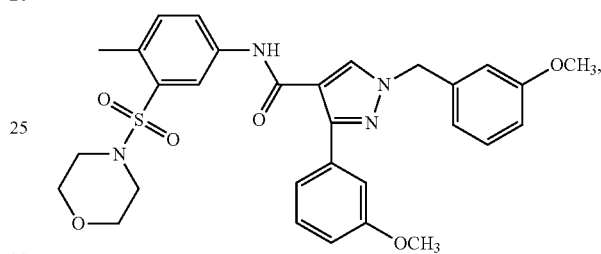
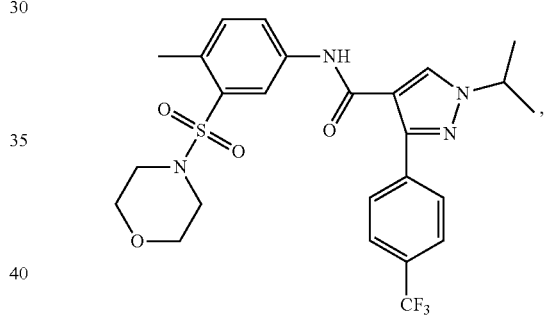
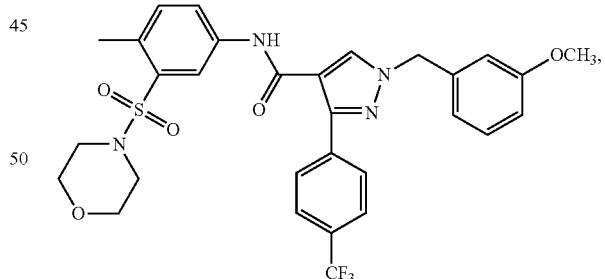
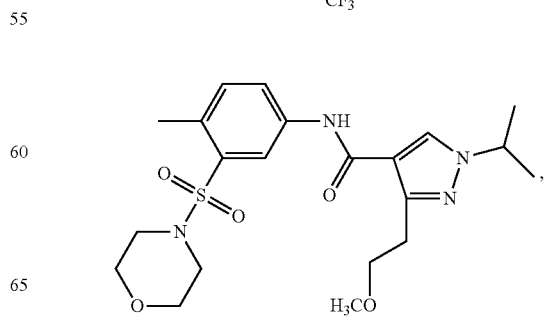

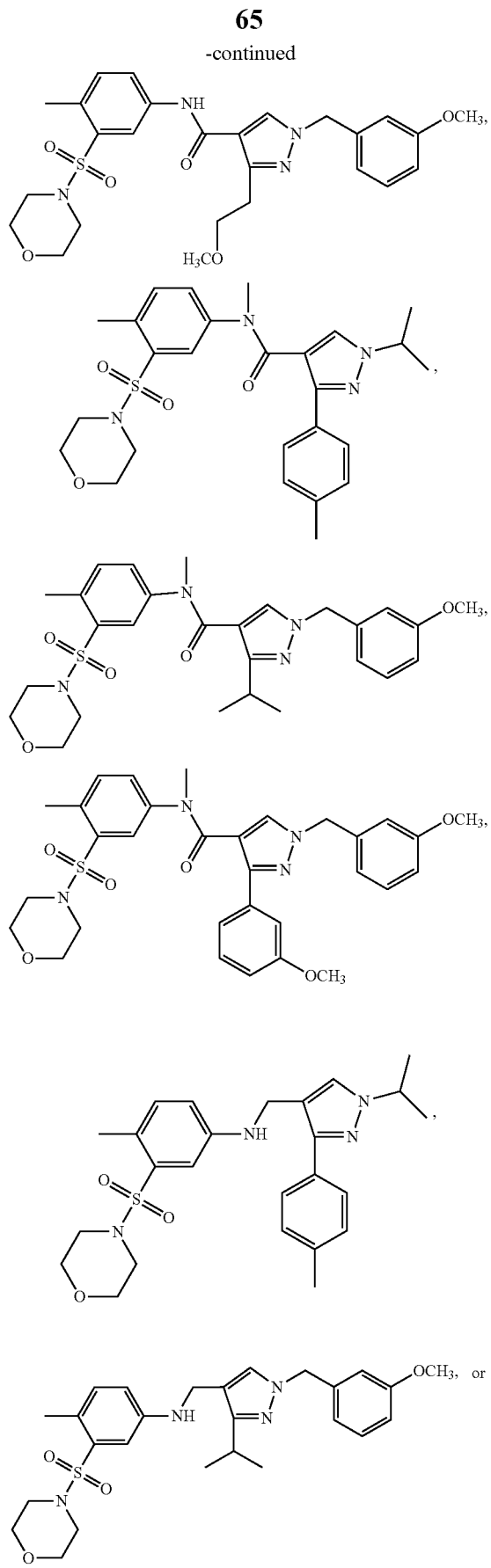

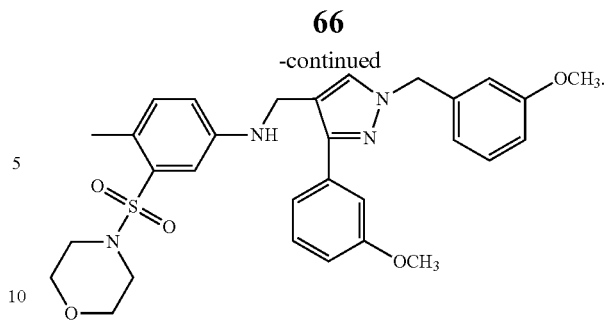

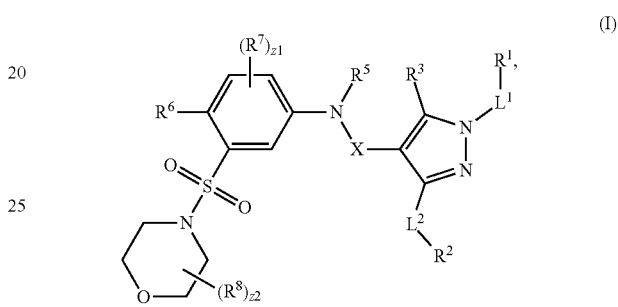

24. A pharmaceutical composition comprising a pharmaceutically acceptable excipient and a compound having formula:

(I)

wherein, X is —C(R$^{4A}$)(R$^{4B}$)—, —C(O)— or —CY(OH)—; Y is hydrogen, halogen, —N$_3$, —NO$_2$, —CF$_3$, —CCl$_3$, —CBr$_3$, —CI$_3$, —CN, —OR$^{9A}$, —NHR$^{9A}$, —COOR$^{9A}$, —CONHR$^{9A}$, —SH, —SO$_3$H, —SO$_4$H, —SO$_2$NH$_2$, —NHNH$_2$, —ONH$_2$, —OCH$_3$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; L$^1$ is independently a bond, —C(O)—, —C(O)O—, —O—, —S—, —NR$^{9B}$—, —C(O)NR$^{9B}$—, —S(O)$_n$—, —S(O)NR$^{9B}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; L$^2$ is independently a bond, —C(O)—, —C(O)O—, —O—, —S—, —NR$^{9C}$—, —C(O)NR$^{9C}$—, —S(O)$_n$—, —S(O)NR$^{9C}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; R$^1$, R$^2$, R$^3$, R$^{4A}$, R$^{4B}$, R$^5$, R$^6$, R$^7$, and R$^8$ are independently hydrogen, halogen, —N$_3$, —CF$_3$, —CCl$_3$, —CBr$_3$, —CI$_3$, —CN, —CHO, —OR$^{11A}$, —NR$^{11B}$R$^{11C}$, —COOR$^{11A}$, —C(O)NR$^{11B}$R$^{11C}$, —NO$_2$, —SR$^{11D}$, —S(O)$_{n11}$R$^{11B}$, —S(O)$_{n11}$OR$^{11B}$, —S(O)$_{n11}$NR$^{11B}$R$^{11C}$, —NHNR$^{11B}$R$^{11C}$, —ONR$^{11B}$R$^{11C}$, —NHC(O)NHNR$^{11B}$R$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{9A}$, R$^{9B}$, R$^{9C}$ are independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n11 is 1 or 2; z1 is 1, 2, 3, 4, 5, or 6; z2 is 1, 2, 3, 4, 5, 6, 7, or 8; and $R^{11A}$, $R^{11B}$, $R^{11C}$ and $R^{11D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

25. A method of antagonizing Farnesoid X Receptor (FXR) protein, said method comprising contacting a FXR protein with a compound of any one of embodiments 1 to 23 the pharmaceutical composition of claim 24.

26. A method of treating metabolic disease, said method comprising administering to a subject in need thereof a compound having the formula:

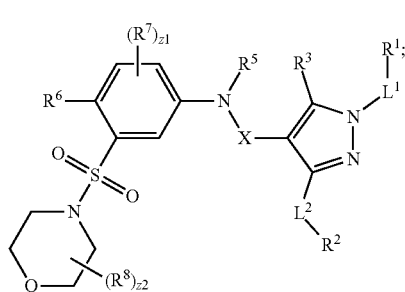

(I)

wherein, X is $-C(R^{4A})(R^{4B})-$, $-C(O)-$ or $-CY(OH)-$; Y is hydrogen, halogen, $-N_3$, $-NO_2$, $-CF_3$, $-CCl_3$, $-CBr_3$, $-CI_3$, $-CN$, $-OR^{9A}$, $-NHR^{9A}$, $-COOR^{9A}$, $-CONHR^{9A}$, $-SH$, $-SO_3H$, $-SO_4H$, $-SO_2NH_2$, $-NHNH_2$, $-ONH_2$, $-OCH_3$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^1$ is independently a bond, $-C(O)-$, $-C(O)O-$, $-O-$, $-S-$, $-NR^{9B}-$, $-C(O)NR^{9B}-$, $-S(O)_n-$, $-S(O)NR^{9B}-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^2$ is independently a bond, $-C(O)-$, $-C(O)O-$, $-O-$, $-S-$, $-NR^{9C}-$, $-C(O)NR^{9C}-$, $-S(O)_n-$, $-S(O)NR^{9C}-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$, $R^2$, $R^3$, $R^{4A}$, $R^{4B}$, $R^5$, $R^6$, $R^7$, and $R^8$ are independently hydrogen, halogen, $-N_3$, $-CF_3$, $-CCl_3$, $-CBr_3$, $-CI_3$, $-CN$, $-CHO$, $-OR^{11A}$, $-NR^{11B}R^{11C}$, $-COOR^{11A}$, $-C(O)NR^{11B}R^{11C}$, $-NO_2$, $-SR^{11D}$, $-S(O)_{n11}R^{11B}$, $-S(O)_{n11}R^{11B}$, $-S(O)_{n111}NR^{11B}R^{11C}$, $-NHNR^{11B}R^{11C}$, $-ONR^{11B}R^{11C}$, $-NHC(O)NHNR^{11B}R^{11C}$, substituted or unsubstituted alkyl, substituted or unsubstituted heteroalkyl, substituted or unsubstituted cycloalkyl, substituted or unsubstituted aryl, or substituted or unsubstituted heteroaryl; $R^{9A}$, $R^{9B}$, $R^{9C}$ are independently hydrogen, halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n11 is 1 or 2; z1 is 1, 2, 3, 4, 5, or 6; z2 is 1, 2, 3, 4, 5, 6, 7, or 8; and $R^{11A}$, $R^{11B}$, $R^{1C}$, and $R^{11D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, thereby treating said metabolic disease.

27. The method of embodiment 26, wherein X is $-C(O)-$.

28. The method of embodiment 26 or 27, wherein $L^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

29. The method of any one of embodiments 26 to 28, wherein $L^1$ is substituted or unsubstituted $C_1$-$C_5$ alkylene.

30. The method of any one of embodiments 26 to 29, wherein $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene 31. The method of any one of embodiments 26 to 30, wherein $L^2$ is a bond or substituted or unsubstituted alkylene.

32. The method of any one of embodiments 26 to 31, wherein $R^1$ and $R^2$ are independently substituted or unsubstituted alkyl, substituted or unsubstituted cycloalkyl, substituted or unsubstituted heterocycloalkyl, substituted or unsubstituted aryl, or substituted or unsubstituted heteroaryl.

33. The method of embodiment 26, having formula:

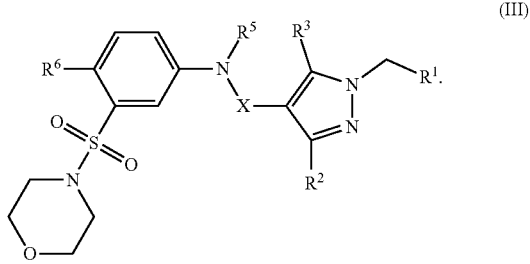

(III)

34. The method of embodiment 33, wherein $R^1$ is $R^{10}$-substituted or unsubstituted alkyl, $R^{10}$-substituted or unsubstituted cycloalkyl, or $R^{10}$-substituted or unsubstituted aryl, wherein $R^{10}$ is independently hydrogen, halogen, $-N_3$, $-CF_3$, $-CCl_3$, $-CBr_3$, $-CI_3$, $-CN$, $-CHO$, $-OR^{10A}$, $-NR^{10B}R^{10C}$, $-COOR^{10A}$, $-C(O)NR^{10B}R^{10C}$, $-NO_2$, $-SR^{10D}$, $-S(O)_{n10}R^{10B}$, $-S(O)_{n10}OR^{10B}$, $S(O)_{n10}NR^{11B}R^{10C}$, $-NHNR^{10B}R^{10C}$, $-ONR^{10B}R^{10C}$, $-NHC(O)NHNR^{10B}R^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10A}$, $R^{10B}$, $R^{10C}$, and $R^{10D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n10 is 1 or 2.

35. The method of embodiment 33 or 34, wherein $R^1$ is $R^{10}$-substituted or unsubstituted alkyl, unsubstituted cycloalkyl, or $R^1$-substituted or unsubstituted aryl; $R^{10}$ is hydrogen, halogen, $CF_3$, $OR^{10A}$; and $R^{10A}$ is hydrogen or unsubstituted $C_1$-$C_5$ alkyl.

36. The method of embodiment 26 having formula:

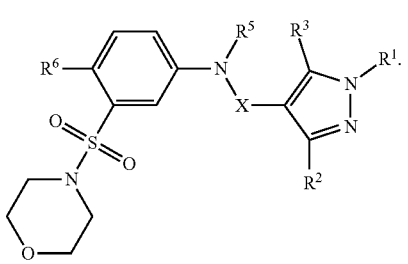

(II)

37. The method of embodiment 36, wherein $R^1$ is substituted or unsubstituted alkyl, substituted or unsubstituted aryl or substituted or unsubstituted heteroaryl.

38. The method of embodiment 36 or 37, wherein $R^1$ is $R^{10}$-substituted or unsubstituted alkyl, $R^{10}$-substituted or unsubstituted aryl, or $R^{10}$-substituted or unsubstituted heteroaryl, wherein $R^{10}$ is independently halogen, $—N_3$, $—CF_3$, $—CCl_3$, $—CBr_3$, $—CI_3$, $—CN$, $—CHO$, $—OR^{10A}$, substituted or unsubstituted alkyl, substituted or unsubstituted heteroalkyl, substituted or unsubstituted aryl, or substituted or unsubstituted heteroaryl; and $R^{10A}$ is independently hydrogen or substituted or unsubstituted alkyl.

39. The method of any one of embodiments 36 to 38, wherein $R^1$ is $R^1$-substituted or unsubstituted alkyl, $R^1$-substituted or unsubstituted aryl, or $R^{10}$-substituted or unsubstituted heteroaryl; $R^{10}$ is halogen, $—CF_3$, $OR^{10A}$, substituted or unsubstituted $C_1$-$C_5$ alkyl, or substituted or unsubstituted aryl; and $R^{10A}$ is hydrogen or methyl.

40. The method of any one of embodiments 26 to 39, wherein $R^2$ is hydrogen, substituted or unsubstituted alkyl, substituted or unsubstituted aryl, or substituted or unsubstituted heteroaryl.

41. The method of any one of embodiments 26 to 40, wherein $R^2$ is hydrogen, $R^{17}$-substituted or unsubstituted alkyl or $R^{17}$-substituted or unsubstituted aryl, wherein $R^{17}$ is independently halogen, $—N_3$, $—CF_3$, $—CCl_3$, $—CBr_3$, $—CI_3$, $—CN$, $—CHO$, $—OR^{17A}$, $—NR^{17B}R^{17C}$, $—COOR^{17A}$, $—C(O)NR^{17B}R^{17C}$, $—NO_2$, $—SR^{17D}$, $—S(O)_{n17}R^{17B}$, $—S(O)_{n17}OR^{17B}$, $—S(O)_{n17}NR^{17B}R^{17C}$, $—NHNR^{17B}R^{7C}$, $—ONR^{17B}R^{7C}$, $—NHC(O)NHNR^{17B}R^{7C}$, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^8$-substituted or unsubstituted heteroaryl; $R^{17A}$, $R^{17B}$, $R^{17C}$, and $R^{17D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n17 is 1 or 2.

42. The method of any one of embodiments 26 to 41, wherein $R^2$ is hydrogen, $R^{17}$-substituted or unsubstituted alkyl, $R^{17}$-substituted or unsubstituted aryl, or $R^{17}$-substituted or unsubstituted heteroaryl; $R^{17}$ is substituted or unsubstituted alkyl, halogen, $—CF_3$, $—OR^{17A}$; and $R^{17A}$ is hydrogen or unsubstituted $C_1$-$C_5$ alkyl.

43. The method of any one of embodiments 26 to 42, wherein $R^3$ is hydrogen, halogen, $—N_3$, $—CF_3$, $—CCl_3$, $—CBr_3$, $—CI_3$, $—CN$, $—CHO$, $—OR^{3A}$, or substituted or unsubstituted alkyl, wherein $R^{3A}$ is hydrogen or unsubstituted $C_1$-$C_5$ alkyl.

44. The method of any one of embodiments 26 to 43, wherein $R^3$ is hydrogen, halogen, $—CF_3$, $—OH$, or substituted or unsubstituted alkyl.

45. The method of any one of embodiments 26 to 44, wherein $R^5$ is hydrogen or methyl.

46. The method of any one of embodiments 26 to 45, wherein $R^7$ and $R^8$ are independently hydrogen, halogen, $—N_3$, $—CF_3$, $—CCl_3$, $—CBr_3$, $—CI_3$, $—CN$, $—CHO$, $—OH$, $—OCH_3$, substituted or unsubstituted alkyl, or substituted or unsubstituted heterocycloalkyl.

47. The method of embodiment 26 to 46, wherein the compound has the formula:

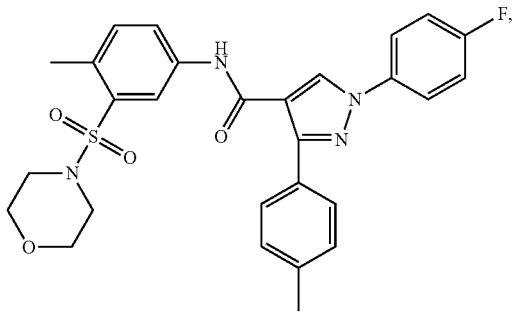

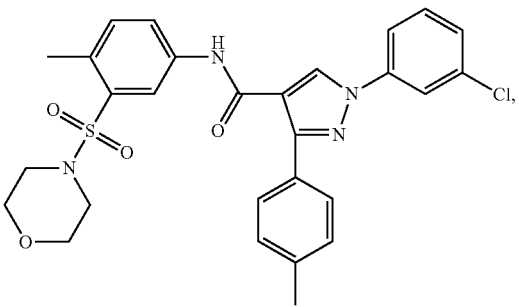

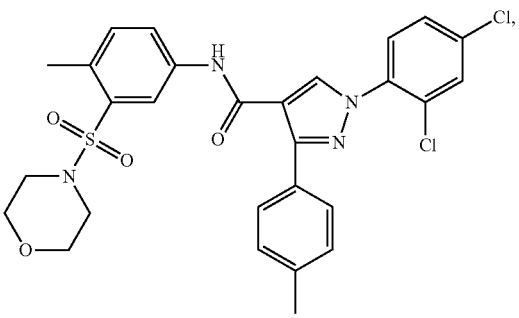

71
-continued
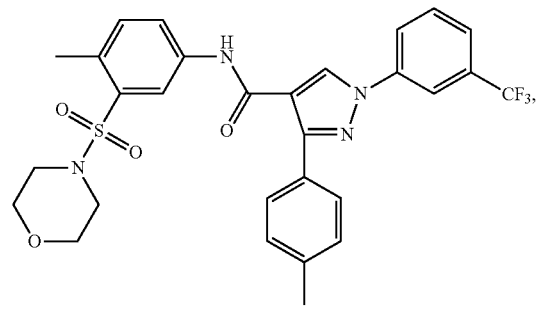
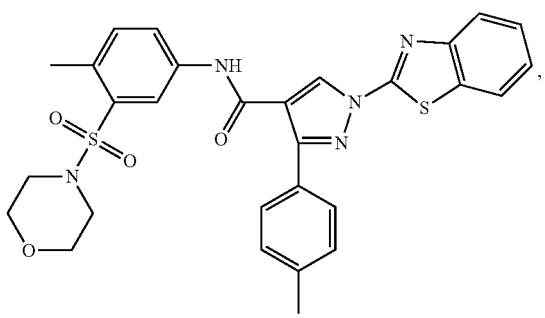
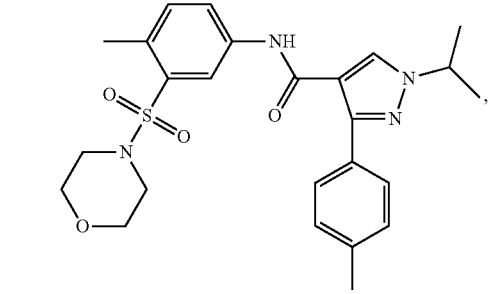
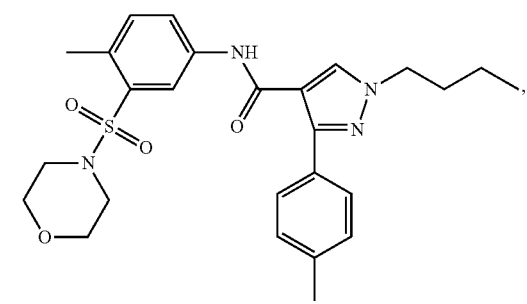
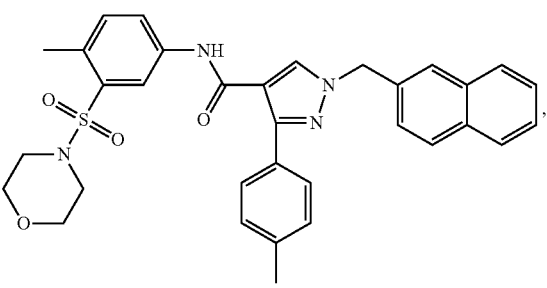
72
-continued
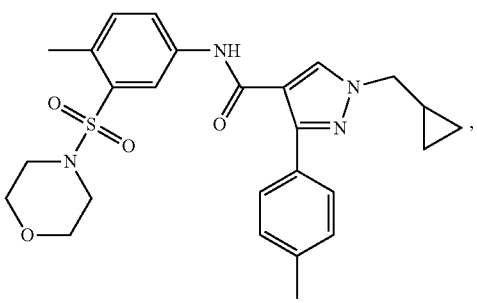
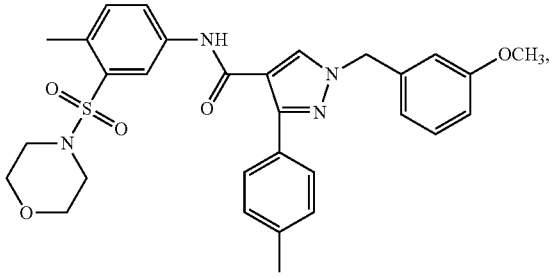
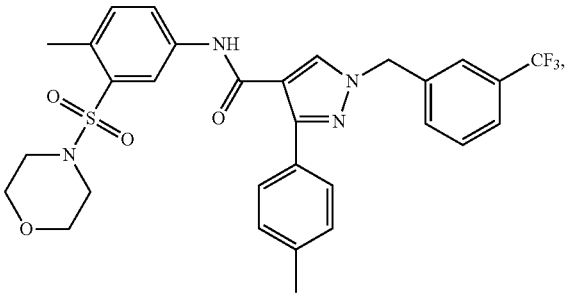
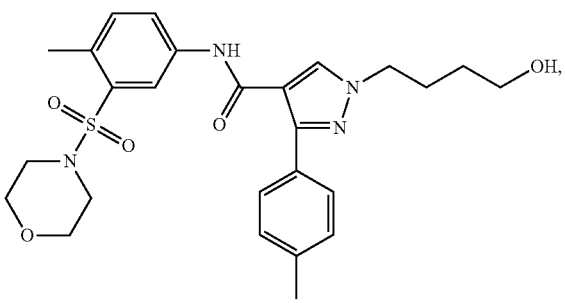
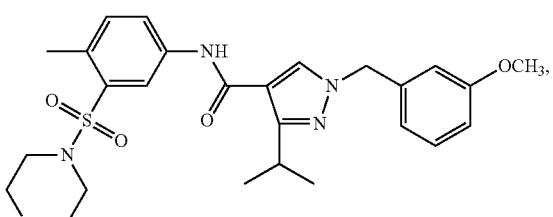
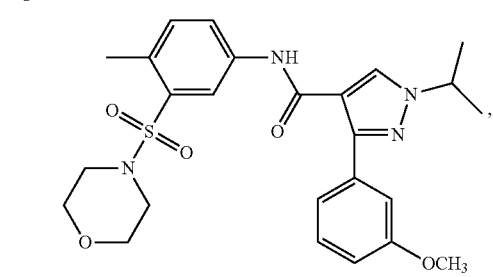

73
-continued
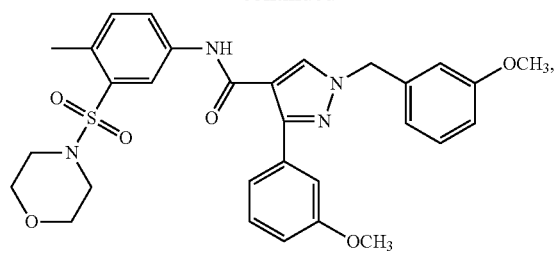
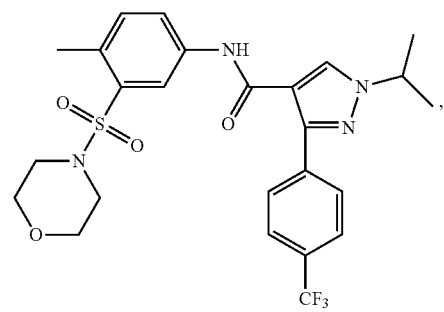
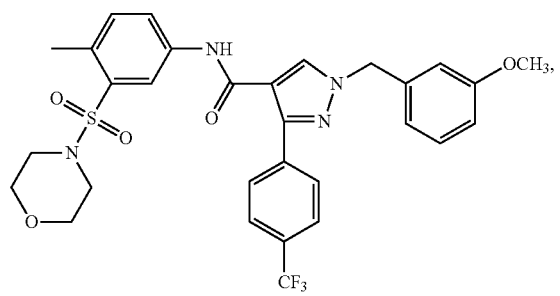
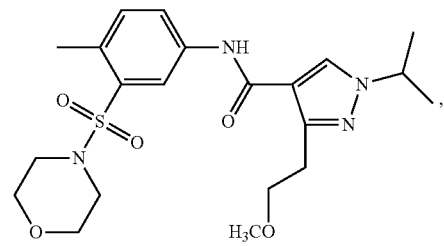
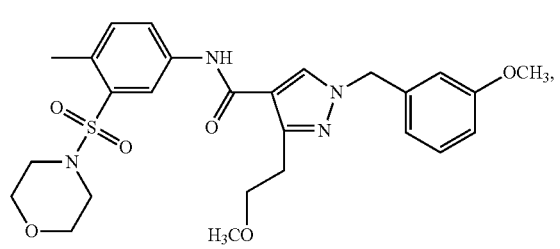
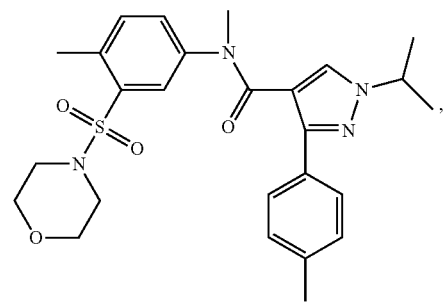
74
-continued
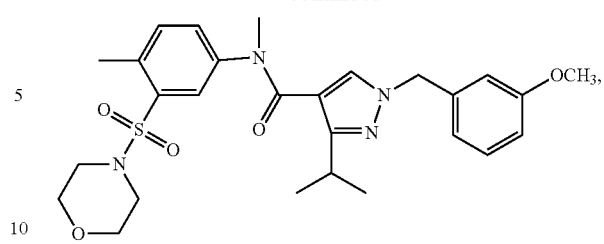
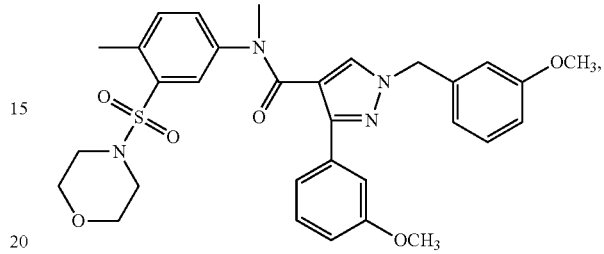
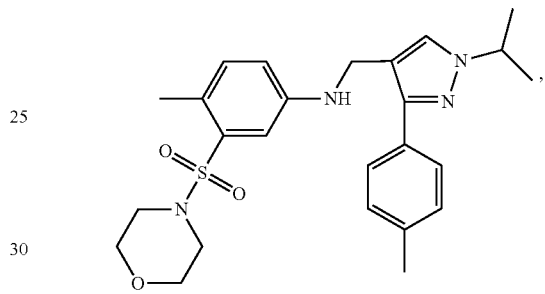
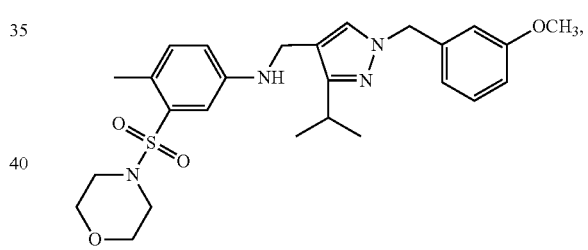
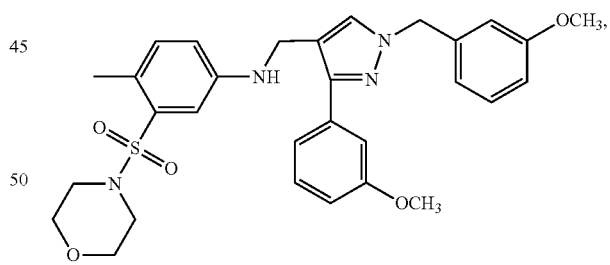
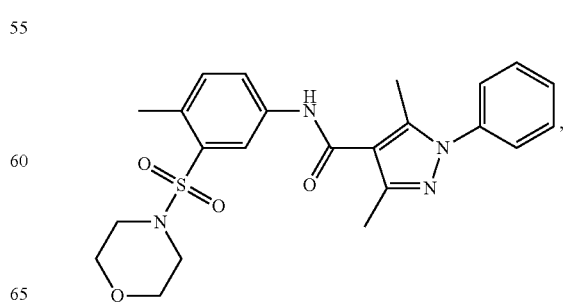

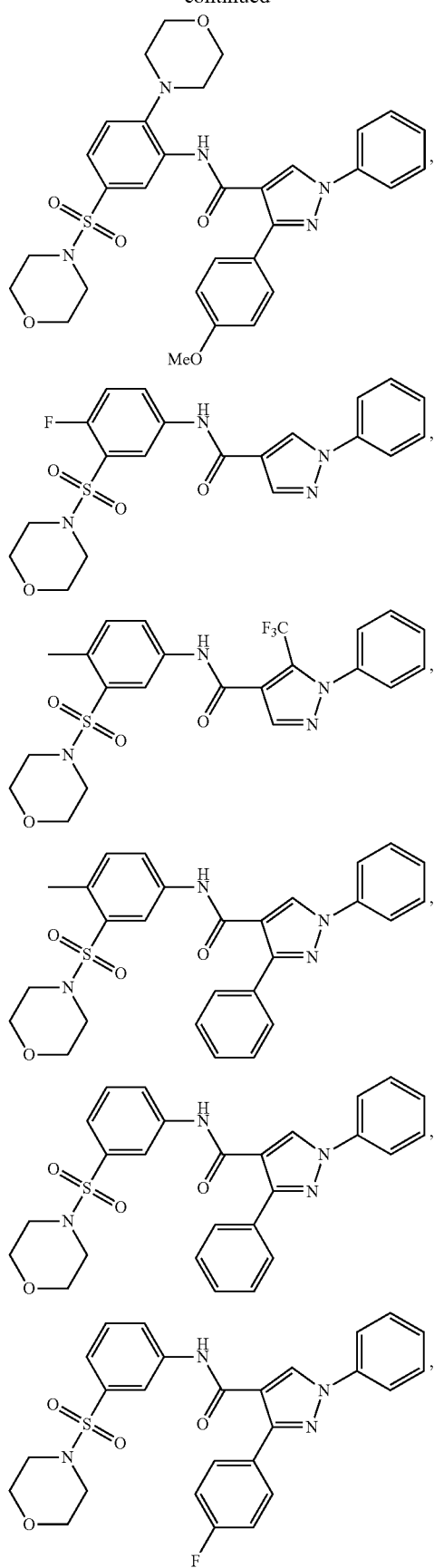
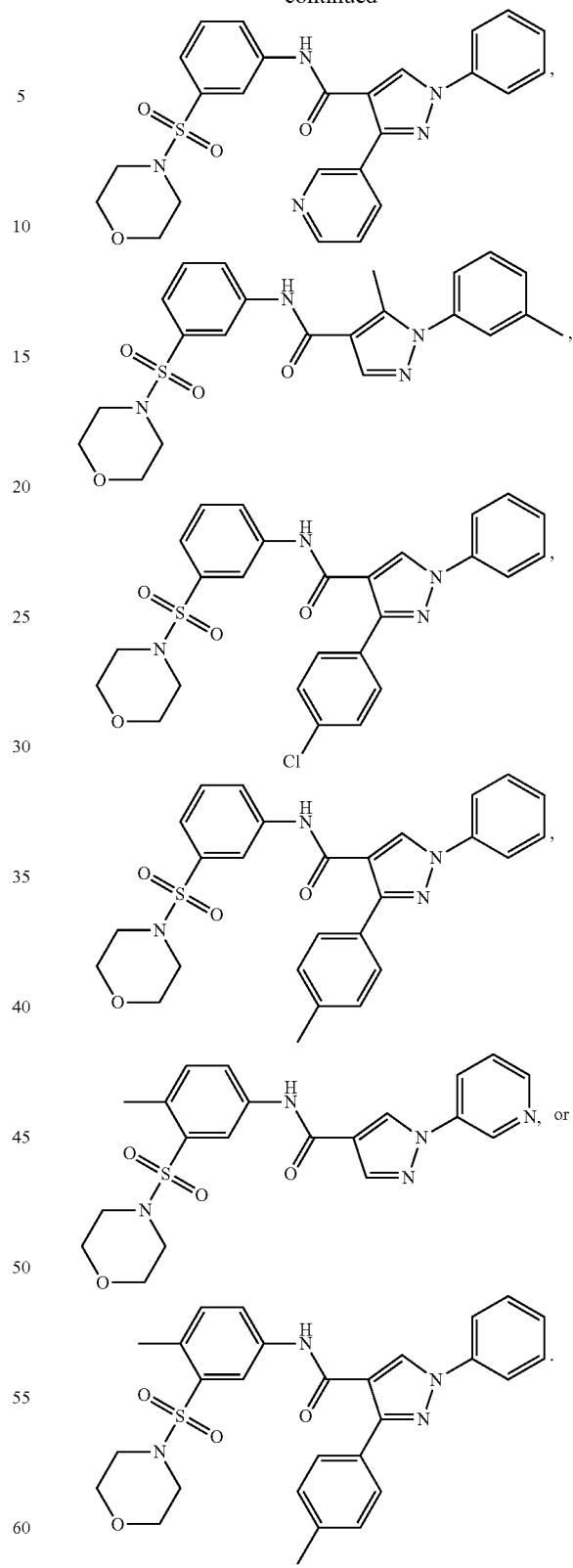
48. The method of any one of embodiments 26 to 47, wherein said metabolic disease comprises dyslipidemia, insulin-resistance, increased blood pressure, visceral obesity, cholestasis, or hypercoagubility.

49. The method of any one of embodiments 26 to 48, wherein said metabolic disease comprises at least cholestasis or at least dyslipidemia.

50. The method of embodiment 48 or 49, wherein said dyslipidemia is hypertriglyceridemia.

EXAMPLES

Modulating FXR may be beneficial for treating all aspects of the metabolic syndrome, a complex cluster of cardiovascular disease with risk factors including dyslipidemia, insulin-resistance, increased blood pressure, visceral obesity and hypercoagubility.[5] Recent findings also suggest that FXR may act as a key metabolic regulator in the liver to maintain the homeostasis of liver metabolites.[6] Synthetic and natural ligands that have either agonistic or antagonistic activity against FXR are powerful chemical tools for controlling the activity of FXR and managing various clinical conditions. FXR ligands have been investigated in preclinical studies for targeted therapy of metabolic diseases, but have shown many limitations.[7] There is, therefore, a need for novel potent and selective modulators as agonists or antagonists of FXR, both for potential clinical applications, as well as for further studies to better understand its biological functions.

Several potent and selective FXR agonists have been reported, such as GW4064 and 6α-ethylchenodeoxycholic acid (6-ECDCA).[8] These agonists have been shown to decrease plasma triglyceride (TG) levels and increase the synthesis of high-density lipoprotein cholesterol.[9] However, preclinical development of FXR agonists is limited by the complex response, including undesirable effects, triggered by activation of FXR in the liver. For example, FXR activation inhibits bile acid synthesis and basolateral efflux of bile by indirectly repressing the expression of cholesterol 7 alpha-hydroxylase, or cytochrome P450 7A1 (CYP7A1), the rate-limiting enzyme of the bile acid synthesis pathway.[10] In addition, activation of FXR, while reducing TG levels in hypertriglyceridemic patients, would also decrease levels of high density lipoprotein (HDL) and lead to accumulation of cholesterol in the body as a consequence of the inhibited bile acid synthesis. Furthermore, FXR agonists interfere with the ability of constitutive androstane receptor (CAR) to regulate basolateral transporters in hepatocytes. These effects might worsen liver injury in a subset of patients with obstructive cholestasis (a severe liver disease that impairs bile flow and causes irreversible liver damage), thereby limiting the preclinical development and possible clinical use of FXR agonists. In contrast, FXR antagonists might be useful for understanding the function of FXR and ultimately for treating liver disorders, if they targeted a specific cluster of genes and thus avoided the detrimental side effects mediated by FXR agonists. The development of a FXR-specific antagonist is needed to possibly validate the clinical relevance of antagonizing FXR.[11]

An antagonist of FXR, if selective for upregulating CYP7A1 expression, may be useful as a therapeutic agent to increase the conversion of cholesterol to bile acids, resulting in lower low density lipoprotein (LDL) levels in hyperlipidemic patients. This activity may occur through FXR's regulation of the expression of small heterodimer partner (SHP).[2] SHP attenuates the expression of CYP7A1 by inhibiting the activity of liver receptor homologue 1 (LRH-1), which augments CYP7A1 expression. Antagonizing FXR decreases SHP levels, which, in turn, would increase CYP7A1 activity, enhance cholesterol metabolism in vivo and reduce serum levels of total cholesterol. In addition, FXR can promote expression of an intestinal bile acid-binding protein (I-BABP) gene.[12] When expression of I-BABP is repressed by an antagonist of FXR, re-absorption of bile acids in the ileum is repressed, which may reduce the amount of bile acid that returns to the liver, and, therefore, promote the expression of CYP7A1. Thus, an FXR antagonist could potentially induce repression of I-BABP expression in the ileum, leading to reduced levels of serum cholesterol, and suggesting potential as a therapeutic agent for hypercholesterolemia in humans.[11]

Despite the potential of FXR as a therapeutic target for metabolic diseases, few FXR antagonists (synthetic small molecules or natural products) are described. Recently, the natural product guggulsterone was identified as the first putative FXR antagonist.[13] However, guggulsterone is not a specific FXR antagonist with low FXR antagonistic potency (ICso of 12-25 µM).[14] In addition, its mechanism of antagonism for FXR is unclear. Thus, rather than being a true antagonist of FXR, guggulsterone is a unique FXR ligand that has antagonistic activity in coactivator association assays and can enhance the action of FXR agonists in vivo.[15]

Furthermore, nonsteroidal antagonists have been reported in the literature, which antagonizes FXR in in vitro reporter assays but acts in a gene-selective manner in vivo; it has an agonistic effect on the expression of CYP7A1, antagonistic effect on the expression of I-BABP, and does not affect SHP expression, the best-characterized FXR target gene.[20] Recent ligand-based virtual screening identified other potential FXR antagonists.[21] However, these antagonists lack potency. 22

FXR antagonists may be discoverable through the use of a time-resolved fluorescence resonance energy transfer (TR-FRET) assay.[23] Identified chemotypes include heterocyclic amide compounds.[24] The pyrazole heterocycle has long been considered a privileged scaffold in drug discovery on the basis of its wide-ranging biological activities, including modulating G-protein coupled receptor modulators, inhibiting cyclooxygenase-2 (COX-2), and p38 MAP kinase.[25] However, investigating pyrazole heterocycles is challenging given the breadth of biological activity. Thus identification of potential FXR antagonists means selecting a structural motif to serve as the scaffold of a focused library, and optimizing to develop more potent and selective FXR antagonists. The antagonistic effect of a substituted pyrazole carboxamide (Z26476908) was examined against FXR. Synthesizing 1,3,4-trisubstituted-pyrazole carboxamides as lead to the development of several novel compounds, exemplified by 4j or 1-(3-Methoxybenzyl)-3-(3-methoxyphenyl)-N-(4-methyl-3-(morpholinosulfonyl) phenyl)-1H-pyrazole-4-carboxamide) with significantly FXR antagonistic activities compared to Z26476908. 4j is the most potent FXR antagonist to date.

Example 2

Figure 2:
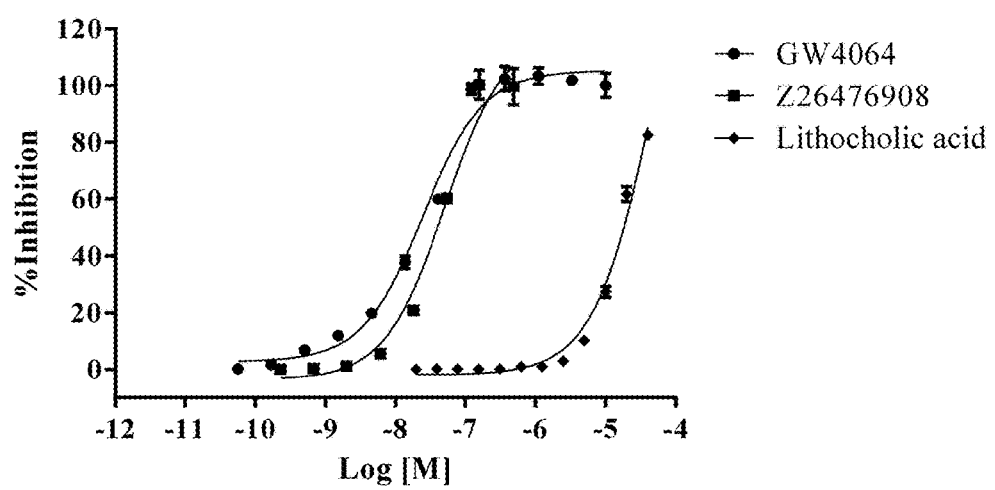
FIG. 2: FXR binding activities of GW4064, Z26476908, and lithocholic acid in an FXR TR-FRET binding assay (2A). FXR agonistic activities (GW4064, Z26476908, or lithocholic acid alone) and antagonistic activities (Z26476908 and lithocholic acid in the presence of 400 nM GW4064) in a cell-based FXR transactivation assay (2B). GW4064 and lithocholic acid were used as agonistic and antagonistic control, respectively.
Figure 2:
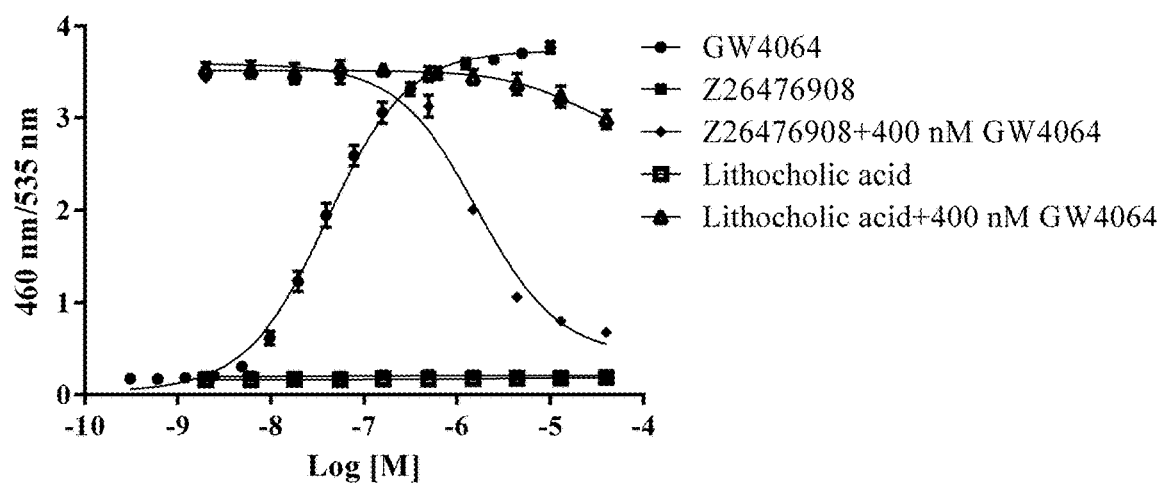

Identification of a Substituted Pyrazole-4-Carboxamide Z26476908 as a Template for Designing Novel FXR Antagonists Sixteen (16) substituted pyrazole carboxamides were examined for any activity through FXR biochemical TR-FRET binding, FXR cell-based agonistic and antagonistic, and cytotoxicity assays. Among the carboxamide analogs, Z26476908, a 1,3,4-trisubstituted-pyrazole carboxamide analog, had the highest FXR binding affinity ($IC_{50}$=47 nM) and appeared as a relatively potent FXR antagonist ($IC_{50}$ of 2.62 µM) (FIG. 2).

Example 3

Design and Synthesis of 1,3,4-Trisubstituted Pyrazole Nonsteroidal FXR Antagonists With the novel substituted pyrazole-4-carboxamide framework in hand, a series of trisubstituted-pyrazole carboxamide analogs were synthesized and evaluated for their receptor binding affinity and antagonistic potency in modulating the transcriptional activity of FXR. No structural information was available on the binding mode of FXR antagonists nor was a co-crystal structure of substituted pyrazole carboxamide framework complexed with the LBD of FXR available. Without being bound by any theory, the flexible nature of FXR side chains suggests the FXR LBD may have considerable flexibility to accommodate ligands of different shapes by changing its conformation in response to ligand binding.[28]

Figure 3:
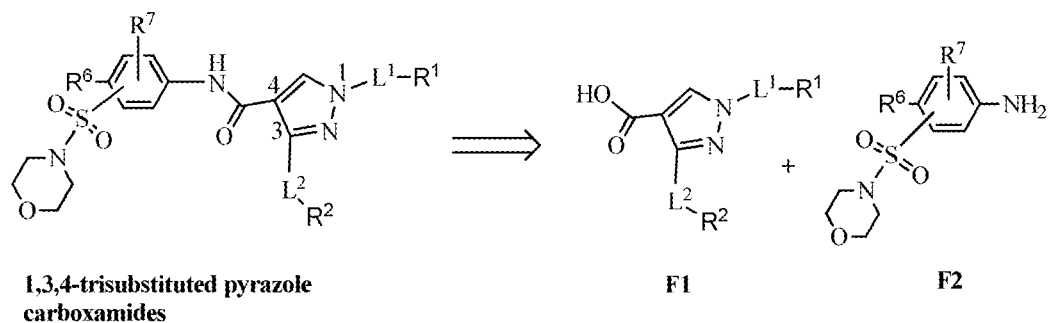
FIG. 3: The retro-analysis of 1,3,4-trisubstituted pyrazole carboxamides.

On the basis of the detailed analysis of the synthesized 16 substituted pyrazole carboxamides as described herein, the substituted morpholinosulfonyl moiety of aniline on the 4-position may be important to improve the antagonistic activity against FXR. The alternative deconstructive hypothesis for fragment binding was investigated the 1,3,4-trisubstituted pyrazole-based molecules.[29] Retrospectively, 1,3,4-trisubstituted-pyrazole carboxamides can be considered formed by two fragments: the substituted-$N^1$—C3-pyrazole core (herein "F1") and substituted morpholinosulfonyl aniline moiety chain (herein "F2") (FIG. 3).

Figure 4:
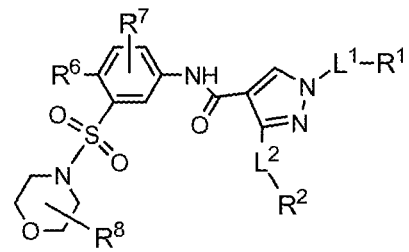
FIG. 4: A focused two-component small array of pyrazoles designed for optimization.

We identified that the substituted $N^1$—C3-pyrazole moiety is sensitive to modifications. Thus various hydrophobic residues, such as alkyl or methoxy residues, substituted in the in $R_1$ or $R_2$ positions of the phenyl-ring significantly improve antagonistic activity. We also determined that the substituted $N^1$—C3-pyrazole core (F1) and morpholinosulfonyl) aniline (F2) could bind separately to FXR by using 2- or 4-methyl-3-(morpholinosulfonyl)aniline and 3-(morpholinosulfonyl)aniline as F2 functionalities. A series of substituted F1 fragments was prepared as described in the Experimental Section (See 3a-3e). The antagonistic effect of F1 fragments and F2 fragments were tested in a cell-based transient transfection assay. F1 failed to show an antagonistic effect against FXR, while F2 had an low antagonistic effect against FXR. However, by connecting F1 moieties to F2 moieties through a linker of just one covalent bond by an amide bridge, the resulting carboxamide compounds had dramatically improved antagonistic activity against FXR, exemplified by compounds 4 series (FIG. 4).

The F2 fragments have a hydrophobic region centered on the double hydrogen bond acceptor (sulfone) and had very weak antagonistic activity against FXR. Such fragments may provide considerable conformational rigidity to the receptor recognition after joining with F1 fragments. Analysis indicated that the position of the morpholinosulfonyl moiety of the F2 phenyl ring is sensitive to modifications. Further analysis of the structural requirements as effective FXR antagonists showed that the meta-position-substituted morpholinosulfonyl moiety on the aniline amide moiety influences the antagonistic activity. Thus the 3-(morpholinosulfonyl)aniline moiety of the amide moiety was fixed to act as a specific anchor in FXR binding recognition.

Variations of $R^3$ on the F2 fragments also affected the antagonistic potency. For example, replacing the 3-(morpholinosulfonyl) aniline with 4-methyl-3-(morpholinosulfonyl) aniline in the final conjugation with selected F1 resulted in higher antagonistic activity. Additionally, replacing the 4-methyl substituent on the aniline ring with a 2-methyl substituent conjugated with the same F1 resulted in lower antagonistic activities. Inclusion of an unmethylated 3-morpholinosulfonyl aniline substantially decreased the antagonistic potency. Taken together, this preliminary analysis provided insight into the structural requirements for effective FXR antagonists—indicating that 4-methyl-3-(morpholinosulfonyl) aniline in the F2 functionality is appropriate factor.

Example 4

F2 fragments were considered as a key pharmacophoric region where a substituent, such as 4-methyl substituted aniline, may be crucial for hydrophobic interaction with FXR. The 4-methyl-3-(morpholinosulfonyl) aniline was fixed and two regions of F1 fragments modified. It was discovered that a subtle optimization between steric/hydrophobic effects of the $R^1$ substituents and fine-tuning of the hydrogen-bonding capability of $R^2$ substituents, resulted in novel FXR antagonists displaying high FXR binding affinity and potent cellular antagonistic effects against FXR.

Figure 5:
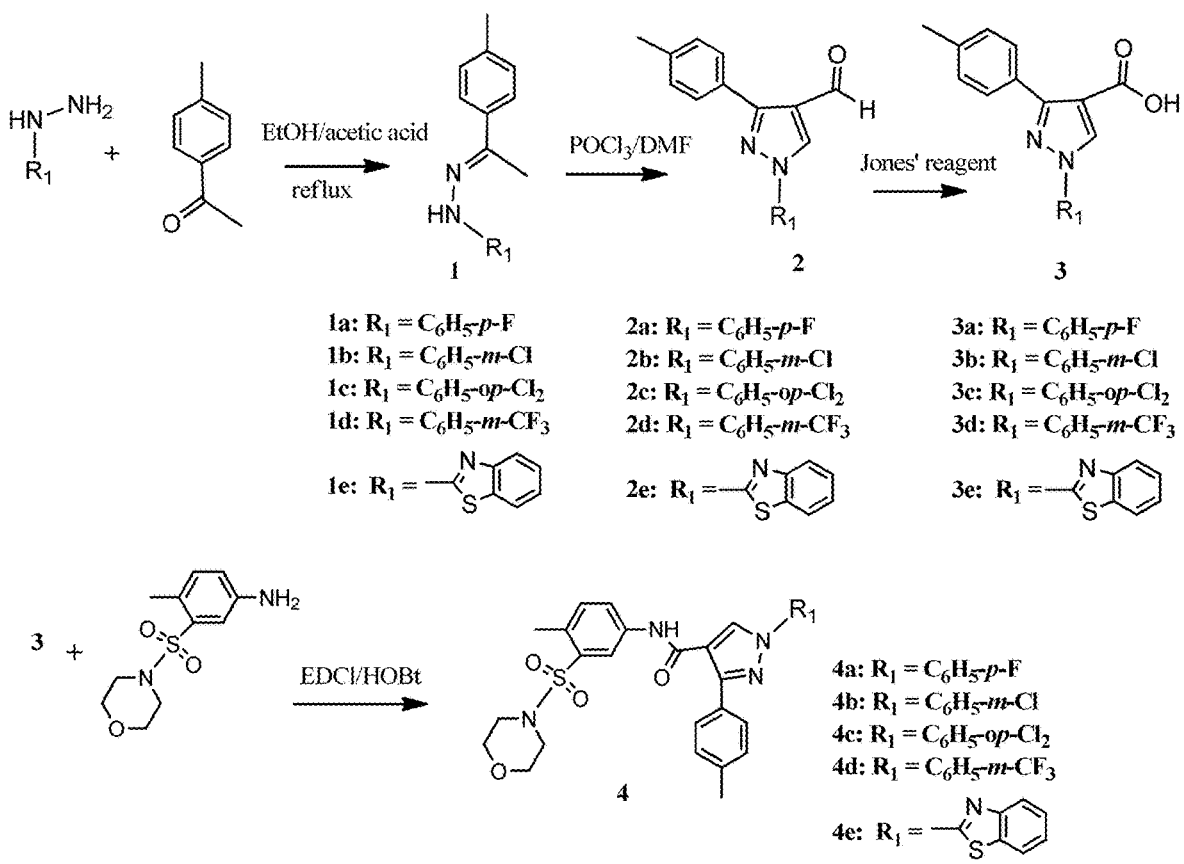
FIG. 5: Initial exploration of pyrazole core via Vilsmeier-Haack reaction to introduce $R_1$ as substituted 1,3-diphenylpyrazole-4-carboxylic acids 4 in the $N^1$-position of pyrazole.

As indicated in FIG. 5, the $N^1$- and C3-pyrazole moieties on the pyrazole core were explored with various electronic and hydrophobic substituted alkyls and phenyls. Without being bound by any particular theory, we reasoned that potent analogs of 1,3,4-trisubstituted-pyrazole carboxamides may have structural features in common. From a parallel library synthesis perspective, compounds of this type are attractive because they contain only two vectors (denoted $R^1$ and $R^2$) that allow the introduction of significant structural diversity. A synthetic strategy was developed to optimize the $N^1$—C3-pyrazole core structure through substitutions at $R^1$ and $R^2$ as a focused two-component small array of pyrazole. Combining structural considerations and chemical feasibility, the initial strategy included a medicinal chemistry parallel approach involving variations in both the electronic and steric properties of the appendages of the central pyrazole nucleus. A scaffold expansion based on two diverse points given by the substituents and their positions on the pyrazole ring, as well as the substituents ($R^1$ and $R^2$) on the $N^1$,C3-pyrazole rings, was therefore designed (FIGS. 5 and 6).

On the basis of the above design, two protocols for preparing the 1,3,4-trisubstituted-pyrazole carboxamides were developed to optimize the synthesis of compounds 4. These protocols included preparing various structural isomers to determine whether the positions of the $R_1$ and $R_2$ could affect compound activity. The intermediates 3 and 7 (FIGS. 5 and 6) were prepared via two possible routes to allow access to final functional analogs. In the first route, lead optimization was initiated through exploration of the phenyl functionality located on the $N^1$-position. A series of para- and meta-substitutions on the $N^1$-pyrazole ring was investigated (FIG. 5). Condensation between substituted acetophenones and substituted phenylhydrazines provides hydrazones 1. A Vilsmeier-Haack reaction assembles the pyrazole nucleus templates.[30] However, these conditions either do not form key aldehydes or have poor yields. The Vilsmeier-Haack reaction was modified by adding the corresponding phenylhydrazones to an excess equivalence of $POCl_3$ and DMF at 0° C., then heated to 60-70° C. with stirring over 18 h under $N_2$ to afford the desired key cyclized aldehydes 2 at a 70-90% yield after hydrolysis. Oxidation of the pyrazole-4-carboxaldehydes with a Jones' reagent[31] yielded the corresponding pyrazole-4-carboxylic acids 3. Finally, the corresponding acids 3 were subsequently coupled with 4-methyl-3-(morpholinosulfonyl) aniline through a Mitsunobu reaction[32] in the presence of an activating coupling agent (i.e., HOBt and EDCI) to produce the desired 4 with amide side bond properly constructed. The synthetic pathways used to obtain the 5 analogs of 1,3,4-trisubstituted-1H-pyrazoles 4 are illustrated in FIG. 5.

Figure 6:
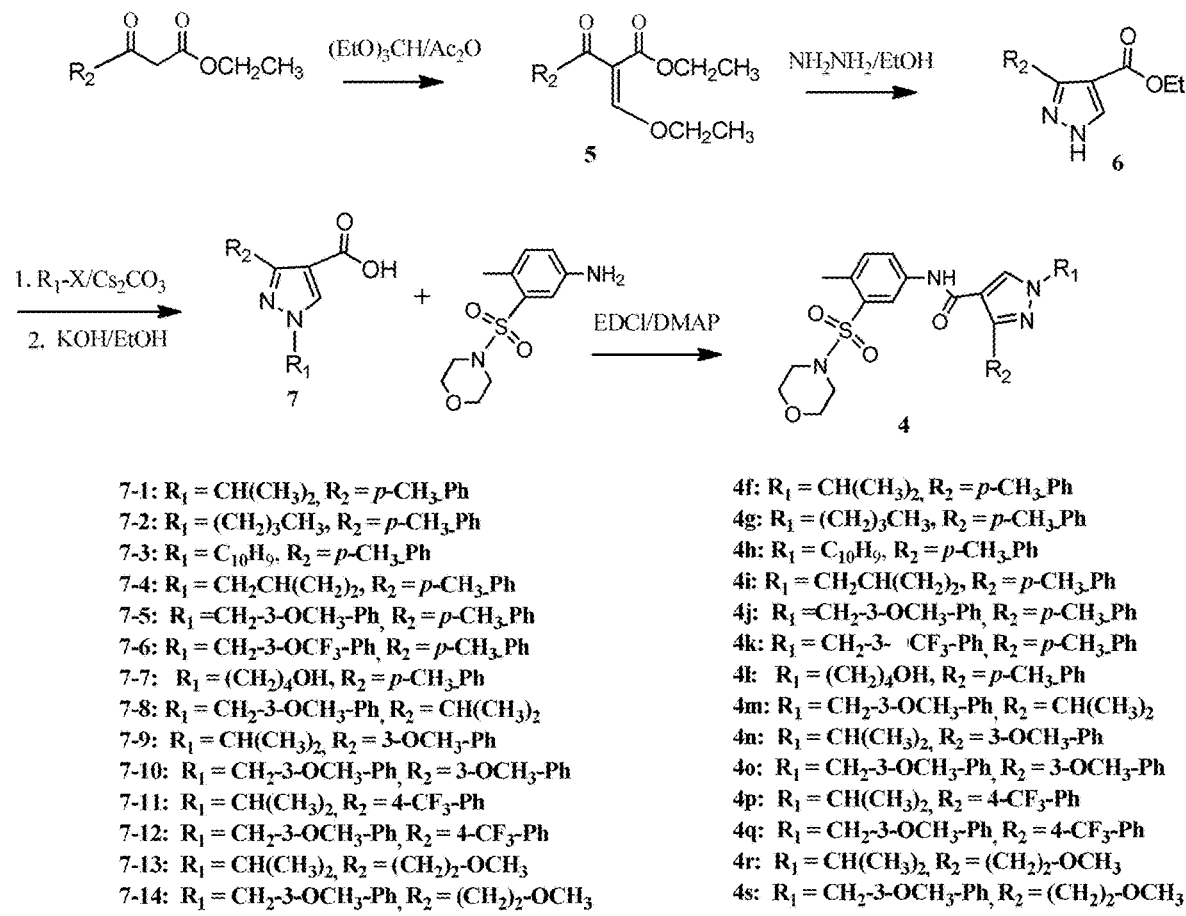
FIG. 6: Alternative exploration of the pyrazole core to introduce $R^1$ and $R^2$ as substituted $N^1$—C3-substituted pyrazoles of 4f-4s.

$R^2$ functional groups were investigated for the structure requirements for FXR antagonistic activity as shown in FIG. 6. The introduction of $R_2$ groups was carried out by treating β-keto esters with triethyl orthoformate in the presence of $Ac_2O$ as a catalyst to provide the corresponding ethoxymethylene intermediate 5. Cyclization of 5 with hydrazine in dry ethanol afforded the pyrazole core 6. The $N^1$-alkylation reaction of 6 with excess appropriate bromoalkyl and bromobenzyl was performed in the presence of cesium carbonate as the base and acetonitrile as solvent. The ethyl esters 6 were hydrolyzed under basic conditions to afford the corresponding carboxylic acid 7. This was followed by a Mitsunobu coupling with 4-methyl-3-(morpholinosulfonyl) aniline in the presence of EDCI/DMAP as a fixed coupling reagent to produce the desired 12 products 4f-4s.

Figure 7:
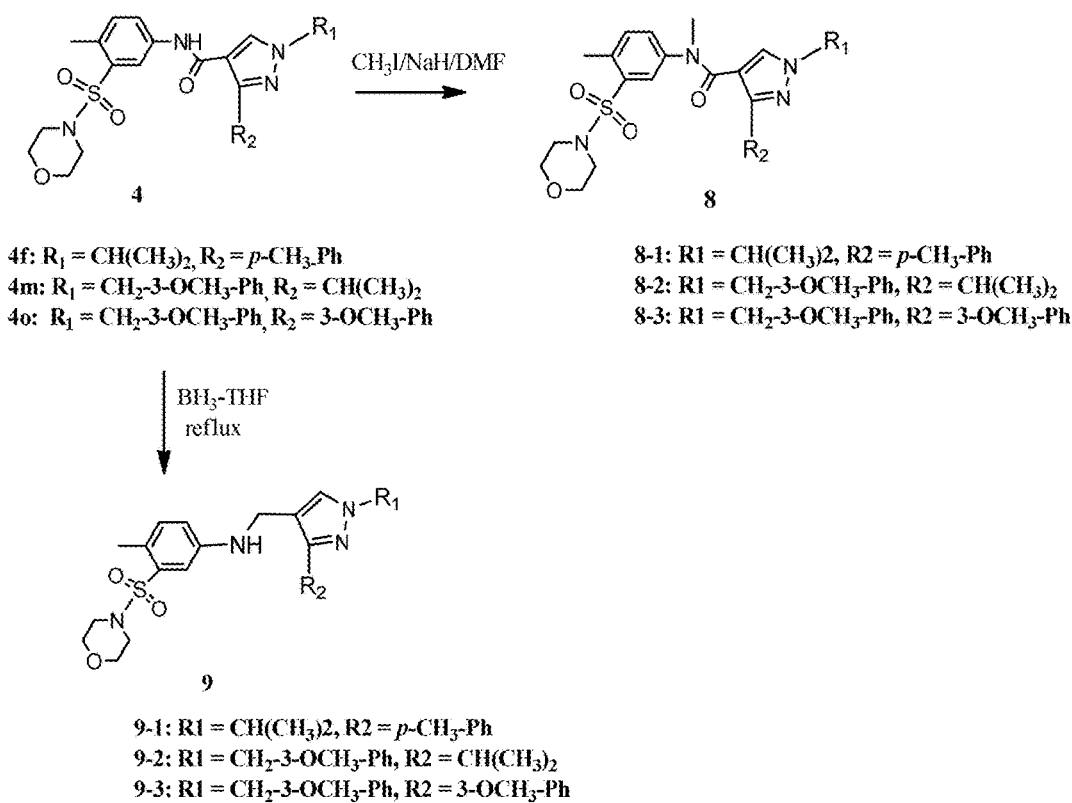
FIG. 7: N-methyl examination and amide reduction of 4f, 4m, and 4o gave corresponding compounds 8 and 9.

The amide moiety was examined to determine if the amide bridge was sensitive to modifications. Three amides of series 4 were varied to generate compounds 8. Compounds 4f, 4m, and 4o were chosen to react with iodomethane in the presence of sodium hydride to give N-alkylation compounds 8 (FIG. 7). The amide position was considered to be a site of potential metabolism.[33] Accordingly, derivatives containing reduced amides were synthesized to investigate. The amide groups in 4f, 4m, and 4o were reduced to corresponding amines with 1N borane-THF complex to yield compounds 9, illustrated in FIG. 7.

Example 5

FXR TR-FRET Binding Assay.

The FXR binding affinities of Z26476908 and the 23 synthesized 1,3,4-trisubstituted-pyrazol-4-carboxamide analogs is shown in FIGS. 5-7, along with control compounds GW4064 and lithocholic acid (LCA). All compounds were tested through an in vitro FXR TR-FRET binding assay using DY246 as the fluorescent probe.[23] TR-FRET assays were chosen due their advantages of low background fluorescence interference and increased sensitivity compared to other fluorescence-based assays, such as FI, FP and FRET assays.[34] DY246 is a derivative of GW4064, which is a potent FXR agonist. DY246 also acts as a potent FXR agonist (EC50 of 550 nM) and has successfully been used as a fluorescent probe in a high throughput screening campaign to identify FXR antagonists.[23] In a representative assay, DMSO (vehicle and negative control), 10 μM GW4064 (positive control), and titrations of GW4064, lithocholic acid or other chemicals were incubated for 20 minutes with appropriate mixture of GST-FXR-LBD, Tb-anti-GST and DY246, after which the TR-FRET signals were collected and activity for each chemical was normalized to DMSO negative control (0% inhibition) and 10 μM GW4064 positive control (100% inhibition). The activities of compounds that displayed inhibitory effects in a dose-dependent manner were fit into a one-site competitive binding equation to derive individual $IC_{50}$ values. The TR-FRET binding activities were summarized in Tables 1, 2, and 3. Many of these compounds had significantly improved FXR binding affinity when compared to Z6908. Noticeably, 4j had an $IC_{50}$ of 7.5 nM in the FXR TR-FRET binding assay, which was 5.26-fold more potent than the control chemical Z26476908 ($IC_{50}$ of 47 nM) (Tables 1, 2, and 3; FIG. 8A).

TABLE 1

The effect of varying the substitution pattern of the 1,3,4-substituted-pyrazole-4-carboxamide derivatives on their biological activities (scaffold A).

Scaffold A

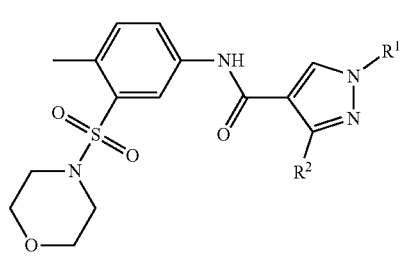

| Compound | $R^1$ | $R^2$ | FXR TR-FRET Binding | | GB FXR Cell Anta. | | GB FXR Cell Cyto | |
|---|---|---|---|---|---|---|---|---|
| | | | % Inh. | $IC_{50}{}^a$ | % Inh. | $IC_{50}{}^a$ | % Inh. | $IC_{50}$ |
| GW4064 | | | 100 ± 4.3 (10 μM) | 19.8 ± 2.5 nM | NA | NA | NT | NA |
| Lithocholic Acid | | | 82.3 ± 0.9 (40 μM) | 18.3 ± 1.2 | 16.1 ± 0.5 (40 μM) | NA | NT | NA |
| Z26476908 | Ph | 4-$CH_3$—Ph | 100.2 ± 5.2 (164 nM) | 47.0 ± 5.1 nM | 77.2 ± 2.2 (40 μM) | 2.62 ± 0.13 μM | 17.9 ± 0.5 (40 μM) | NA |
| 4a | 4-F—Ph | 4-$CH_3$—Ph | 95.0 ± 1.2 (493 nM) | 24.3 ± 0.6 nM | 72.0 ± 2.2 (40 μM) | 2.49 ± 0.006 μM | 18.5 ± 1.0 (40 μM) | |
| 4b | 3-Cl—Ph | 4-$CH_3$—Ph | 99.3 ± 1.1 (164 nM) | 10.4 ± 0.9 nM | 60.6 ± 0.9 (40 μM) | 5.91 ± 0.15 μM | NT | NA |
| 4c | 2,4-Di-Cl—Ph | 4-$CH_3$—Ph | 119.8 ± 7.8 (164 nM) | 14.1 ± 0.3 nM | 89.9 ± 1.9 (40 μM) | 1.24 ± 0.12 μM | NT | NA |
| 4d | 3-$CF_3$—Ph | 4-$CH_3$—Ph | 77.5 ± 4.3 (164 nM) | 23.9 ± 2.1 nM | 54.8 ± 1.3 (40 μM) | 22.29 ± 1.14 μM | 7.3 ± 0.2 (40 μM) | NA |

TABLE 1-continued

The effect of varying the substitution pattern of the 1,3,4-substituted-pyrazole-
4-carboxamide derivatives on their biological activities (scaffold A).

Scaffold A

[Chemical structure: 4-methyl-3-(morpholinosulfonyl)phenyl-N-linked carboxamide with 1,3,4-substituted pyrazole bearing R$^1$ on N1 and R$^2$ on C3]

| Compound | R$^1$ | R$^2$ | FXR TR-FRET Binding % Inh. | IC$_{50}$$^a$ | GB FXR Cell Anta. % Inh. | IC$_{50}$$^a$ | GB FXR Cell Cyto % Inh. | IC$_{50}$ |
|---|---|---|---|---|---|---|---|---|
| 4e | 2-methylbenzothiazol-yl-methyl | 4-CH$_3$—Ph | 101.8 ± 2.8 (164 nM) | 17.7 ± 0.4 nM | 79.1 ± 2.4 (40 μM) | 7.91 ± 1.16 μM | 11.5 ± 0.2 (13.3 μM) | NA |
| 4f | (CH$_3$)$_2$CH | 4-CH$_3$—Ph | 130.6 ± 3.8 (4.4 μM) | 49.1 ± 9.9 nM | 99.1 ± 4.4 (40 μM) | 1.69 ± 0.18 μM | NT | NA |
| 4g | CH$_3$(CH$_2$)$_3$ | 4-CH$_3$—Ph | 130.1 ± 0.7 (1.5 μM) | 52.5 ± 4.1 nM | 97.9 ± 8.1 (20 μM) | 11.51 ± 0.07 μM | 10.3 ± 0.3 (4.4 μM) | NA |
| 4h | 2-naphthylmethyl | 4-CH$_3$—Ph | 97.8 ± 1.2 (164 nM) | 10.2 ± 1.6 nM | 84.4 ± 4.1 (40 μM) | 844.1 ± 10.3 nM | 7.9 ± 0.3 (4.4 μM) | NA |
| 4i | cyclopropylmethyl | 4-CH$_3$—Ph | 105.0 ± 4.9 (1.5 μM) | 76.9 ± 2.7 nM | 100.1 ± 3.2 (40 μM) | 848.8 ± 69.0 nM | NT | NA |
| 4j | 3-methoxybenzyl | 4-CH$_3$—Ph | 130.1 ± 5.4 (164 nM) | 7.5 ± 0.8 nM | 98.9 ± 4.3 (40 μM) | 468.5 ± 8.4 nM | NT | NA |
| 4k | 3-trifluoromethylbenzyl | 4-CH$_3$—Ph | 99.2 ± 6.4 (164 nM) | 18.4 ± 1.2 nM | 93.4 ± 3.9 (40 μM) | 515.0 ± 25.4 nM | NT | NA |
| 4l | HO(CH$_2$)$_4$ | 4-CH$_3$—Ph | 89.3 ± 0.1 (493 nM) | 130.3 ± 16 nM | 97.6 ± 3.7 (40 μM) | 2.61 ± 0.29 μM | 5.9 ± 0.2 (40 μM) | NA |
| 4m | 3-methoxybenzyl | CH(CH$_3$)$_2$ | 100.6 ± 5.6 (4.4 μM) | 199.4 ± 21.2 nM | 99.2 ± 2.7 (40 μM) | 3.11 ± 0.58 μM | NT | NA |
| 4n | (CH$_3$)$_2$CH | 3-CH$_3$O—Ph | 149.8 ± 6.9 (13.3 μM) | 159.7 ± 22.6 nM | 97.8 ± 1.5 (40 μM) | 3.49 ± 0.64 μM | 10.8 ± 0.2 (4.4 μM) | |
| 4o | 3-methoxybenzyl | 3-CH$_3$O—Ph | 114.1 ± 3.3 (493 nM) | 42.8 ± 0.5 nM | 89.4 ± 4.2 (40 μM) | 1.24 ± 0.09 μM | NT | NA |
| 4p | (CH$_3$)$_2$CH | 4-CH$_3$—Ph | 133.2 ± 5.3 (4.4 μM) | 77.5 ± 3.7 nM | 100.0 ± 3.7 (40 μM) | 1.95 ± 0.28 μM | 19.5 ± 1.1 (40 μM) | NA |
| 4q | 3-methoxybenzyl | 4-CH$_3$—Ph | 109.1 ± 3.6 (164 nM) | 30.9 ± 3.6 nM | 97.6 ± 0.9 (40 μM) | 592.7 ± 3.0 nM | NT | NA |

TABLE 1-continued

The effect of varying the substitution pattern of the 1,3,4-substituted-pyrazole-4-carboxamide derivatives on their biological activities (scaffold A).

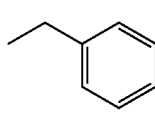

Scaffold A

| Compound | $R^1$ | $R^2$ | FXR TR-FRET Binding % Inh. | FXR TR-FRET Binding $IC_{50}{}^a$ | GB FXR Cell Anta. % Inh. | GB FXR Cell Anta. $IC_{50}{}^a$ | GB FXR Cell Cyto % Inh. | GB FXR Cell Cyto $IC_{50}$ |
|---|---|---|---|---|---|---|---|---|
| 4r | $(CH_3)_2CH$ | $CH_3O(CH_2)_2$ | 98.2 ± 3.8 (40 μM) | 3.42 ± 0.19 μM | 62.5 ± 0.8 (40 μM) | 29.58 ± 1.75 μM | NT | NA |
| 4s | [3-ethyl-phenyl-OCH₃] | $CH_3O(CH_2)_2$ | 113.5 ± 0.8 (13.3 μM) | 389.5 ± 9.4 nM | 95.9 ± 2.4 (40 μM) | 11.1 ± 0.64 μM | NT | NA |

NA: not applicable;
NT: Not toxic (toxicity less than 5%);
GB FXR Cell Anta: GeneBLAzer FXR cell-based antagonistic assay;
GB FXR Cell Cyto: Cytotoxicity assay performed in the GeneBLAzer FXR cells;
$^a$IC50 values represent the means ± SE of at least three independent experiments derived as described in the herein;
% Inh: % Inhibition is presented as the means ± SE of at least three independent experiments calculated as described in the herein, at the herein specified compound concentration.

TABLE 2

The effect of varying the substitution pattern of the 1,3,4-substituted-pyrazole-4-carboxamide derivatives on their biological activities (scaffold B).

Scaffold B

| Compound | $R^1$ | $R^2$ | FXR TR-FRET Binding % Inh. | FXR TR-FRET Binding $IC_{50}$ | GB FXR Cell Anta. % Inh. | GB FXR Cell Anta. $IC_{50}$ | GB FXR Cell Cyto % Inh. | GB FXR Cell Cyto $IC_{50}$ |
|---|---|---|---|---|---|---|---|---|
| 8-1 | $(CH_3)_2CH$ | $4\text{-}CH_3\text{—Ph}$ | 132.9 ± 6.2 (40 μM) | 489.5 ± 21.2 nM | 86.4 ± 2.8 (40 μM) | 16.16 ± 0.28 μM | 15.0 ± 0.7 (40 μM) | NA |
| 8-2 | [3-ethyl-phenyl-OCH₃] | $(CH_3)_2CH$ | 80.3 ± 5.2 (40 μM) | 5.33 ± 0.24 μM | 2.4 ± 0.1 (20 μM) | NA | 13.5 ± 0.4 (40 μM) | NA |
| 8-3 | [3-ethyl-phenyl-OCH₃] | $3\text{-}CH_3O\text{—Ph}$ | 69.7 ± 3.5 (40 μM) | 3.81 ± 0.20 μM | 23.8 ± 0.4 (40 μM) | NA | 19.7 ± 0.4 (40 μM) | NA |

TABLE 3

The effect of varying the substitution pattern of the 1,3,4-substituted-pyrazole-4-carboxamide derivatives on their biological activities (scaffold C).

Scaffold C

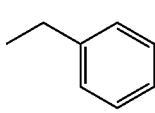

| Compound | R¹ | R² | FXR TR-FRET Binding | | GB FXR Cell Anta. | | GB FXR Cell Cyto | |
|---|---|---|---|---|---|---|---|---|
| | | | % Inh. | IC$_{50}$ | % Inh. | IC$_{50}$ | % Inh. | IC$_{50}$ |
| 9-1 | (CH$_3$)$_2$CH | 4-CH$_3$—Ph | 99.5 ± 2.6 (13.3 μM) | 2.04 ± 0.02 μM | 36.8 ± 0.3 (40 μM) | NA | 10.5 ± 0.3 (40 μM) | NA |
| 9-2 | 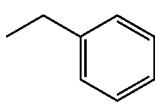 | (CH$_3$)$_2$CH | 72.5 ± 2.7 (4.4 μM) | 2.31 ± 0.32 μM | 64.8 ± 1.9 (40 μM) | 27.83 ± 1.54 μM | 13.9 ± 0.6 (40 μM) | NA |
| 9-3 | (same m-OCH$_3$ benzyl) | 3-CH$_3$O—Ph | 39.8 ± 1.8 (1.48 μM) | NA | 3.1 ± 0.1 (40 μM) | NA | NT | NA |

Example 6

Cell-Based FXR Transactivation Assay.

A GeneBLAzer FXR cell-based assay was used to investigate the cellular activities of the 1,3,4-trisubstituted-pyrazol-4-carboxamide analogs. The assay detects the levels of a β-lactamase reporter controlled by a promoter containing the binding site of the DNA binding domain (DBD) of the GAL4 transcription factor; the Gal4 DBD was fused to the LBD of FXR in this assay.[35]

In typical agonistic tests, DMSO (vehicle and negative control), 10 gtM GW4064 (positive control), and titrations of GW4064, LCA or the 23 synthesized 1,3,4-trisubstituted-pyrazol-4-carboxamide analogs were mixed with GeneBLAzer FXR-UAS-bla HEK 293T cells. The reporter assays were performed after a16 h incubation. No agonistic activities were observed for all the synthesized compounds.

Figure 8:
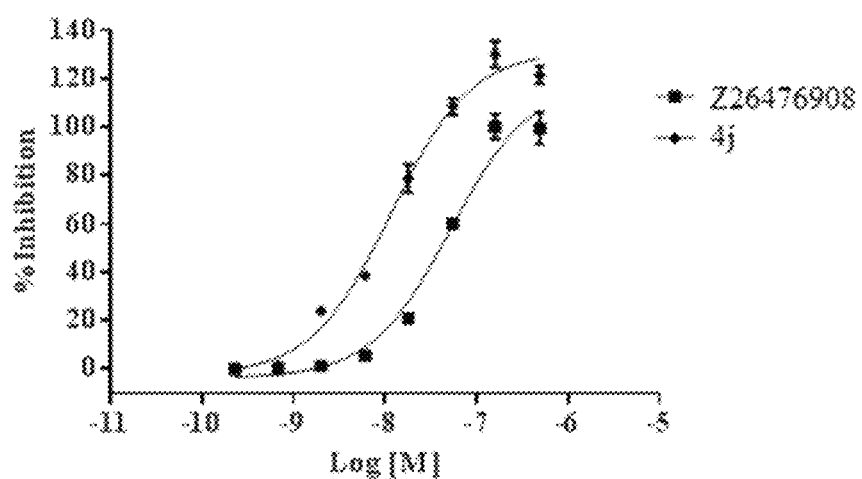
FIG. 8: FXR binding activities of Z26476908 and 4j in a FXR TR-FRET binding assay; Agonistic (Z26476908 and DY268 [4j]) and antagonistic activities (Z26476908 and DY268 [4j]) in an FXR cell-based transactivation assay.
Figure 8:
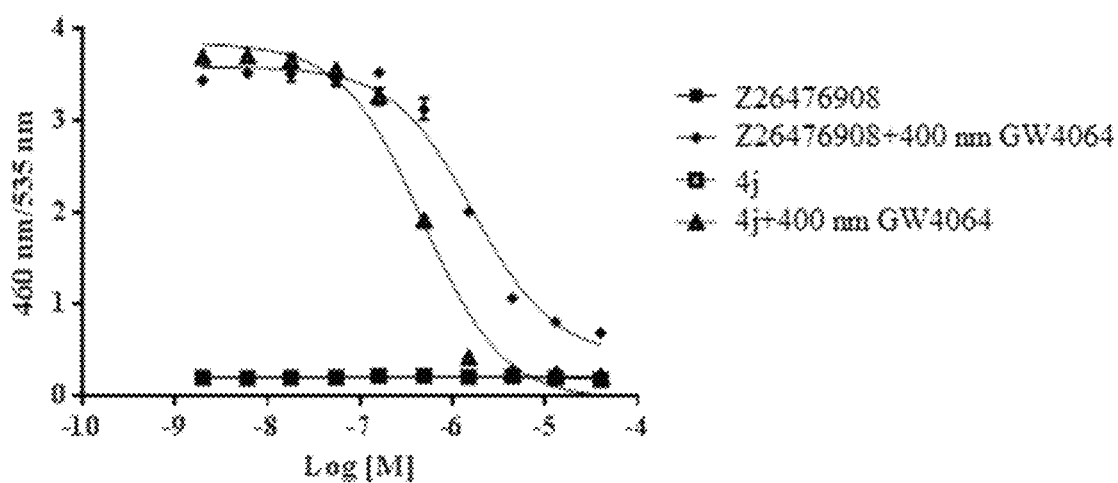
Figure 9:
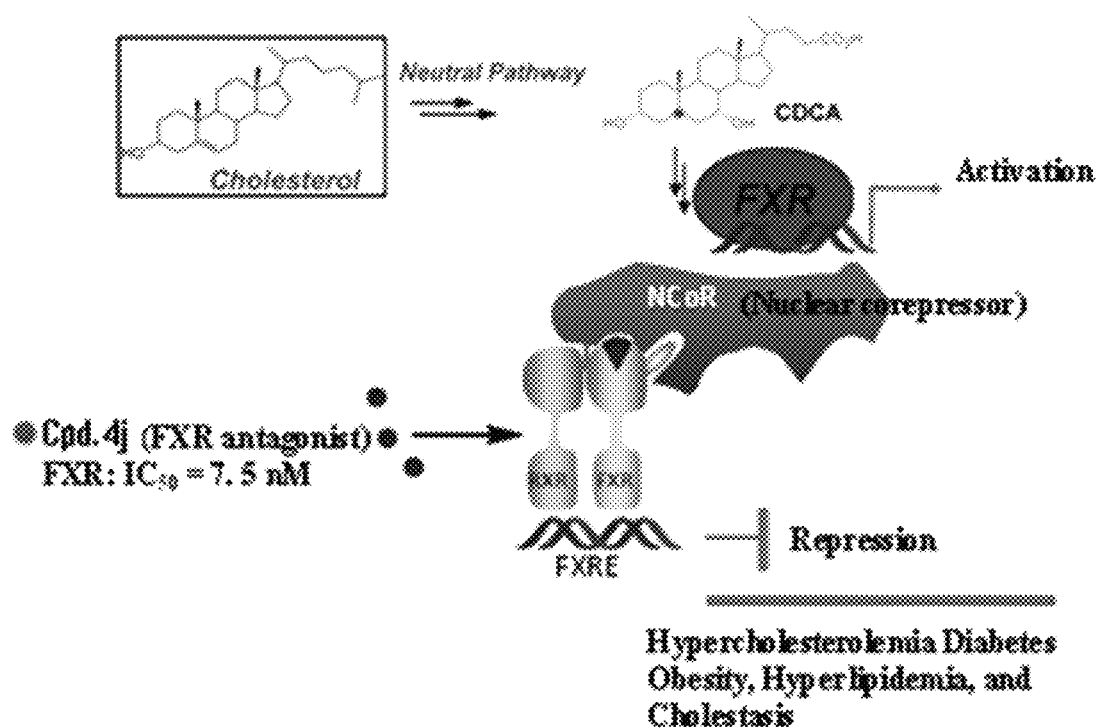
FIG. 9: Cholesterol metabolites act as signaling molecules regulating transcriptional activity of FXR. Bile acids exemplified by CDCA acting at FXR is represented. Hypothetical binding mode of designed FXR antagonist 4j acting at FXR is represented.

For the antagonistic tests, titrations of compounds were tested in the presence of 400 nM GW4064. Assay controls included: DMSO alone (100% inhibition), 400 nM GW4064 alone (0% inhibition), and titrations of LCA in the presence of 400 nM GW4064 (as an assay reference). Activities of compounds that displayed activation or inhibitory activities in a dose-dependent manner were fit into a sigmoidal dose-response equation to derive individual EC$_{50}$ or ICso values. The tested chemicals' FXR activities are summarized in Tables 1, 2, and 3. Many of these compounds had significantly improved antagonistic activity when compared to Z26476908. 4j had an IC$_{50}$ of 468.5 nM, which was 4.59-fold more potent than that of Z26476908 (IC$_{50}$ of 2.62 μM) (Tables 1, 2, and 3; FIG. 8). Without being bound by any particular theory, we hypothesized that the increased antagonistic potency of 4j arose from a hydrophobic group linked to the N$^1$-position of the pyrazole core.

Example 7

Cytotoxicity Assay.

Generally if a tested chemical in the FXR cell-based antagonistic assays caused a signal reduction, it was considered an antagonist. However, signal reduction could also be caused non-specifically if a chemical was cytotoxic (although GeneBLAzer assays are relatively insensitive to cytotoxicity because of their use of ratiometric reading). To examine if certain chemical antagonistic effect was caused by cytotoxicity, the same GeneBLAzer FXR cells were used to perform cytotoxicity assay. This assay was set up like the FXR agonistic assay, with the exception of signal reading. Instead of detecting the reporter activities, CellTiter-Glo® assay was used to detect cell viability. DMSO with cells or without cells group were served as negative (0% Inhibition) or positive (100% Inhibition), respectively. Cytotoxic activities are summarized in Tables 1, 2, and 3. All chemicals tested showed marginal toxicity (% inhibition <5%), therefore the antagonistic effect of the compounds was not caused by non-specific cytotoxicity.

Example 8

The effect of introducing electron withdrawing groups, such as a fluorine, chlorine, dichlorines, and trifluoromethyl atoms, at ortho, meta, or para positions of the N$^1$-phenyl was examined. All of these derivatives (4a, 4b, 4c, 4d, and 4e) improved FXR antagonistic activity by about 3- to 4-fold as compared to Z26476908 (Table 1), indicating that the electron withdrawing groups were well tolerated for antagonistic activity. Without being bound by any particular theory, this observation may be attributed to the higher interaction strength of fluorine or chlorine atoms compared to hydrogen or the slightly larger volume of heterogen which enables a tighter fit. Based on this initial finding, longer benzyl chains or small alkyl groups were introduced to replace the $N^1$-phenyl of the pyrazole moiety. The synthetic methodology for constructing the corresponding pyrazole-4-carboxylic acids was used. Replacing the phenyl ring with small hydrophobic substituents such as isopropyl (4f) or n-butyl (4g) allowed retention of the antagonistic activity toward FXR. Substituting with a methylcyclopropane (4i) decreased the activity by 2-fold for hFXR as compared to Z26476908. Incorporating a bulkier group, such as benzo[d]thiazole (4e), led to higher potency in hFXR by 3-fold. Other substitutions, including longer and bulkier benzyl aromatic substituents such as 2-naphthyl (4h) and benzyl with an electron donating group m-methoxy (4j), enhanced antagonistic activity. Among the $N^1$-alkylated analogs, 4j exhibited the most potent FXR-antagonistic activity, with $IC_{50}$ values of 7.5 nM and 468.5 nM in a FXR TR-FRET binding assay and a FXR cell-based antagonistic assay, respectively. In addition, compound 4j had no FXR agonistic activity and no cytotoxicity.

An expanded hydrophobic moiety at the $N^1$-position and the positive influence of the benzyl-m-methoxy group may be generally preferred at the $N^1$-position of the pyrazole ring. Replacing the original C3-p-methyl phenyl of 4j with the stronger electron-donating m-methoxy phenyl group resulted in analog 4o, which had slightly decreased antagonistic activity (Table 1) compared to 4j. This suggests that the binding pocket of FXR that hosted the m-methoxy phenyl group on the C3 position of pyrazole is not sufficiently wide to accept larger substituents for hydrogen bond interactions with FXR. Replacing the original of C3-p-methyl phenyl ($R_2$) of 4j with a smaller isopropyl group (analog 4m) decreased the potency and affinity, demonstrating that the C3 moiety may be sensitive in terms of steric bulkiness and/or hydrophobicity. For instance, introducing ap-trifluoromethyl phenyl with electron withdrawing properties at the C3 position of the pyrazole ring gave products 4p and 4q which had nanomolar $IC_{50}$ values for in vitro potency. 4p and 4q appeared to have similar antagonistic activities as their parent compounds 4f and 4o. Replacing the p-trifluoromethyl phenyl at the C3 position of the pyrazole ring with a linear 2-methoxy-ethyl group to obtain compounds 4r and 4s, resulted in loss of potency relative to that of 4f and 4o.

In addition to physical and chemical properties, metabolic instability (hydrolysis) of the amide bridge in the carboxamide analogs could contribute to a poor pharmacokinetical profile.[33] The carboxamide nitrogen was methylated to form a tertiary amine 8 and reduction of the amide linker to form a secondary amine 9, was performed. The route described in FIG. 7 rapidly synthesized compounds 4f, 4m, and 4o with amide moieties. The carboxamide nitrogens of 4f, 4m, and 4o were methylated to form N-methyl analogs 8-1, 8-2, and 8-3 (FIG. 7). N-methylation of the amide compounds 8 decreased the antagonistic activity (Table 2 and 3). When compared to the activity of the original amides, 8-1, 8-2, and 8-3 had weak activity at 1 µM against FXR. Similarly, compounds 9 had weak activity at 1 µM. Compound 9 demonstrated more than 300-fold loss in affinity and potency as compared with 4j.

FXR is a nuclear receptor that functions as a physiological receptor for bile acids. A highly potent and selective antagonist of FXR would represent an important novel option that could prove useful for treating dyslipidemia and cholestasis. Thus, there is considerable need to identify lead structures and pharmacorphones in this relatively unexplored area. The strategies and results herein led to optimization of 1,3,4-trisubstituted-pyrazole carboxamides as FXR antagonists.

The series of 1,3,4-trisubstituted-pyrazole carboxamide analogues were developed herein and analyzed for physicochemical properties based on in vitro data. All of these compounds were evaluated for FXR binding affinities in biochemical assay and antagonistic activity in cell-based transactivation assays. All amide compounds reported here behaved as potent FXR antagonists, and showed no FXR agonistic activity. Compound 4j was identified as a promising candidate that had $IC_{50}$ values of 7.5 nM and 468.5 nM in FXR TR-FRET binding assays and FXR cell-based antagonistic assay, respectively.

Example 9

General Procedures:

Organic reagents were purchased from commercial suppliers unless otherwise noted and were used without further purification. All solvents were analytical or reagent grade. All reactions were carried out in flame-dried glassware under argon or nitrogen. Melting points were determined and reported automatically by an optoelectronic sensor in open capillary tubes and were uncorrected. $^1$H NMR and $^{13}$C NMR spectra were measured at 500 MHz and 125 MHz, respectively, using $CDCl_3$ or $CD_3OD$ as solvents and tetramethylsilane ($Me_4Si$) as the internal standard. Flash column chromatography was performed using Sigma-Aldrich silica gel 60 (200-400 mesh), carried out under moderate pressure with columns of an appropriate size packed and eluted with appropriate eluents. All reactions were monitored by thin layer chromatography (TLC) on precoated plates (silica gel HLF). TLC spots were visualized either by exposure to iodine vapor or by irradiation with UV light. Organic solvents were removed under vacuum by a rotary evaporator. Elemental analyses were performed by Columbia Analytical Services Inc, Tucson, Ariz.

(E)-1-(4-fluorophenyl)-2-(1-p-tolylethylidene)hydrazine (1a). To a solution of 4'-methylacetophenone (0.5 g, 3.73 mmol) in 8 mL of acetic acid and 5 mL of water/MeOH, 4-fluorophenylhydrazine hydrochloride (0.6 g, 3.73 mmol) was added. The reaction mixture was stirred at room temperature for 18 h. The reaction mixture was diluted with an additional 30 mL of water and subsequently filtered and the solid was dried in vacuo to afford 0.63 g of beige solid 1a (70% yield): mp 101.8° C. $^1$H NMR ($CDCl_3$) δ 7.68 (d, 2H), 7.19 (d, 3H), 7.07 (t, 2H), 6.98 (d, 2H), 2.37 (s, 3H), 2.23 (s, 3H).

(E)-1-(3-Chlorophenyl)-2-(1-p-tolylethylidene)hydrazine (1b). To a solution of 4'-methylacetophenone (0.5 g, 3.73 mmol) in 8 mL of acetic acid and 5 mL of water/MeOH, 3-chlorophenylhydrazine hydrochloride (0.67 g, 3.73 mmol) was added. The reaction mixture was stirred at room temperature for 18 h. The reaction mixture was diluted with an additional 30 mL of water and subsequently filtered and the solid was dried in vacuo to afford 0.58 g of beige solid 1b (60% yield): mp 100.5° C. $^1$H NMR ($CDCl_3$) δ 7.68 (t, 2H), 7.20 (t, 5H), 6.98 (s, 1H), 6.83 (d, 1H), 2.38 (s, 3H), 2.28 (s, 3H).

(E)-1-(2,4-dichlorophenyl)-2-(1-p-tolylethylidene)hydrazine (1c). To a solution of 4'-methylacetophenone (0.5 g, 3.73 mmol) in 8 mL of acetic acid and 5 mL of water/MeOH, 2,4-dichlorophenylhydrazine hydrochloride (0.8 g, 3.73 mmol) was added. The reaction mixture was stirred at room temperature for 18 h. The reaction mixture was diluted with an additional 30 mL of water and subsequently filtered and the solid was dried in vacuo to afford 0.98 g of beige solid 1c (90% yield): mp 122.7° C. $^1$H NMR (CDCl$_3$) δ 7.71 (t, 2H), 7.61 (d, 2H), 7.29 (s, 1H), 7.021 (d, 3H), 2.38 (s, 3H), 2.28 (s, 3H).

(E)-1-(3-Trifluromethylphenyl)-2-(1-p-tolylethylidene) hydrazine (1d). To a solution of 4'-methylacetophenone (0.5 g, 3.73 mmol) in 8 mL of acetic acid and 5 mL of water/MeOH, 3-trifluoromethylphenylhydrazine hydrochloride (0.66 g, 3.73 mmol) was added. The reaction mixture was stirred at room temperature for 18 h. The reaction mixture was diluted with an additional 30 mL of water and subsequently filtered and the solid was dried in vacuo to afford 1.01 g of beige solid 1d (93% yield): mp 103.7° C. $^1$H NMR (CDCl$_3$) δ 7.72 (d, 2H), 7.44 (m, 4H), 7.28 (d, 2H), 7.14 (s, 1H), 2.41 (s, 3H), 2.27 (s, 3H).

(E)-2-(2-(1-(p-tolyl)ethylidene)hydrazinyl)benzo[d]thiazole (1e). To a solution of 4'-methylacetophenone (0.5 g, 3.73 mmol) in 8 mL of acetic acid and 1 mL of water, 2-hydrazinobenthiazole (0.62 g, 3.73 mmol) was added. The reaction mixture was stirred at room temperature for 18 h. The reaction mixture was diluted with an additional 20 mL of water and subsequently filtered and the solid was dried in vacuo to afford 1 g of beige solid 1e (99% yield): mp 112.6° C. $^1$H NMR (CDCl$_3$) δ 7.74 (d, 2H), 7.68 (d, 1H), 7.53 (d, 1H), 7.36 (d, 1H), 7.25 (d, 2H), 7.16 (d, 1H), 2.41 (s, 3H), 2.17 (s, 3H).

1-(4-fluorophenyl)-3-p-tolyl-1H-pyrazole-4-carbaldehyde (2a). To a solution of a mixture of DMF (3 mL) and POCl$_3$ (1.5 mL, 16.4 mmol) in an ice bath under argon which was stirred for 10 min, was added 1a (0.21 g, 0.87 mmol) dissolved in dichloroethane (5 mL); the mixture was raised to 70° C. and stirred for an additional 18 h. The reaction mixture was then cooled to room temperature, slowly poured into saturated aqueous NaHCO$_3$ (200 mL) under ice cold conditions, and then warmed to room temperature and stirred for 3 h. The aqueous layer was extracted with EtOAc. The organic layers were washed with water and brine, dried over Na$_2$SO$_4$ and concentrated in vacuo to yield 0.21 g (88%) of the title compound: mp 143.8° C., which was used without further purification. $^1$H NMR (CDCl$_3$) δ 10.05 (s, 1H), 8.47 (s, 1H), 7.78 (m, 1H), 7.71 (d, 2H), 7.33 (d, 2H), 7.19 (m, 3H), 2.44 (s, 3H). $^{13}$C NMR (CDCl$_3$) δ 187.0, 156.5, 132.7, 130.9, 130.2, 129.8, 123.9, 123.1, 118.1, 117.8, 23.3.

1-(3-Chlorophenyl)-3-p-tolyl-1H-pyrazole-4-carbaldehyde (2b). To a solution of a mixture of DMF (5 mL) and POCl$_3$ (1.5 mL, 16.4 mmol) in an ice bath under argon which was stirred for 10 min, was added 1b (0.58 g, 2.24 mmol) dissolved in dichloroethane (5 mL); the mixture was raised to 70° C. and stirred for an additional 18 h. The reaction mixture was then cooled to room temperature and slowly poured into saturated aqueous NaHCO$_3$ (200 mL) under ice cold conditions which was warmed to room temperature and stirred for 3 h. The aqueous layer was extracted with EtOAc. The organic layers were washed with water, brine, dried over Na$_2$SO$_4$ and concentrated in vacuo to yield 0.64 g (88%) of the title compound: mp 118.7° C., which was used without further purification. $^1$H NMR (CDCl$_3$) δ 10.05 (s, 1H), 8.53 (s, 1H), 7.88 (s, 1H), 7.67 (d, 3H), 7.46 (t, 1H), 7.31 (d, 3H), 2.44 (s, 3H). $^{13}$C NMR (CDCl$_3$) δ 186.5, 159.3, 141.1, 132.1, 130.9, 130.2, 129.3, 121.6, 118.8, 23.0.

1-(2,4-Dichlorophenyl)-3-p-tolyl-1H-pyrazole-4-carbaldehyde (2c). To a solution of a mixture of DMF (5 mL) and POCl$_3$ (1.5 mL, 16.4 mmol) in an ice bath under argon which was stirred for 10 min, was added 1c (0.61 g, 2.08 mmol) dissolved in dichloroethane (5 mL); the mixture was raised to 70° C. and stirred for an additional 18 h. The reaction mixture was then cooled to room temperature and slowly poured into saturated aqueous NaHCO$_3$ (200 mL) under ice cold conditions which was warmed to room temperature and stirred for 3 h. The aqueous layer was extracted with EtOAc. The organic layers were washed with water, brine, dried over Na$_2$SO$_4$ and concentrated in vacuo to yield 0.53 g (78%) of the title compound: mp 85.8° C., which was used without further purification. $^1$H NMR (CDCl$_3$) δ 10.05 (s, 1H), 8.48 (s, 1H), 7.66 (m, 3H), 7.54 (s, 1H), 7.42 (d, 1H), 7.37 (d, 2H), 2.38 (s, 3H). $^{13}$C NMR (CDCl$_3$) δ 186.6, 156.59 140.9, 137.4, 136.8, 134.1, 132.0, 131.7, 130.8, 129.4, 127.2, 105.7, 22.7.

3-p-Tolyl-1-(3-(trifluoromethyl)phenyl)-1H-pyrazole-4-carbaldehyde (2d). To a solution of a mixture of DMF (5 mL) and POCl$_3$ (1.5 mL, 16.4 mmol) in an ice bath under argon which was stirred for 20 min, was added 1d (0.75 g, 2.56 mmol) dissolved in dichloroethane (7 mL); the mixture was raised to 70° C. and stirred for an additional 18 h. The reaction mixture was then cooled to room temperature and slowly poured into saturated aqueous NaHCO$_3$ (200 mL) under ice cold conditions which was warmed to room temperature and stirred for 3 h. The aqueous layer was extracted with EtOAc. The organic layers were washed with water and brine, dried over Na$_2$SO$_4$ and concentrated in vacuo to yield 0.79 g (93%) of the title compound (mp 155.1° C.), which was used without further purification. $^1$H NMR (CDCl$_3$) δ 10.08 (s, 1H), 8.60 (s, 1H), 8.13 (s, 1H), 7.99 (q, 1H), 7.74 (d, 2H), 7.67 (d, 2H), 7.35 (d, 2H), 2.45 (s, 3H). $^{13}$C NMR (CDCl$_3$) δ 186.6, 157.3, 141.7, 140.8, 132.3, 131.8, 130.9, 130.3, 126.6, 126.2, 123.8, 22.8.

1-(2,3-Dihydro-1H-inden-1-yl)-3-(p-tolyl)-1H-pyrazole-4-carbaldehyde (2f). To a solution of a mixture of DMF (5 mL) and POCl$_3$ (1.5 mL, 16.4 mmol) in an ice bath under argon which was stirred for 20 min, was added 1f (1.0 g, 3.55 mmol) dissolved in dichloroethane (5 mL); the mixture was raised to 60° C. and stirred for an additional 18 h. The reaction mixture was then cooled to room temperature and slowly poured into saturated aqueous NaHCO$_3$ (200 mL) under ice cold conditions which was warmed to room temperature and stirred for an additional 5 h. The aqueous layer was extracted with EtOAc. The organic layers were washed with water, brine, dried over Na$_2$SO$_4$ and concentrated in vacuo to yield 0.74 g (70%) of the title compound: mp 145.3° C., which was used without further purification. $^1$H NMR (CDCl$_3$) δ 10.11 (s, 1H), 9.08 (s, 1H), 7.98 (d, 1H), 7.89 (d, 1H), 7.79 (d, 2H), 7.55 (t, 1H), 7.44 (t, 1H), 7.35 (d, 2H), 2.41 (s, 3H). $^{13}$C NMR (CDCl$_3$) δ 186.0, 157.1, 152.0, 141.5, 134.0, 130.9, 130.3, 128.3, 124.4, 123.2, 23.4.

1-(4-fluorophenyl)-3-p-tolyl-1H-pyrazole-4-carboxylic acid (3a). To a solution of 2a (0.21 g, 0.75 mmol) dissolved in 16 mL of acetone, 5 mL of Jones' reagent was added. The reaction mixture was stirred at room temperature and monitored by TLC. The reaction mixture was poured into water and extracted with EtOAc. The combined organic layers were washed with water and brine, dried over Na$_2$SO$_4$, and concentrated in vacuo to afford 0.16 g (72%) of the title acid: mp 202.0° C. $^1$H NMR (CDCl$_3$) δ 8.51 (s, 1H), 7.75 (m, 3H), 7.32 (d, 2H), 7.18 (t, 4H), 2.41 (s, 3H). $^{13}$C NMR (CDCl$_3$) δ 170.7, 164.5, 155.9, 140.6, 135.1, 132.6, 130.9, 130.6, 130.2, 130.1, 122.8, 118.2, 22.7. Anal. Calcd for C$_{17}$H$_{13}$FN$_2$O$_2$: C, 68.91; H, 4.41; N, 9.45. Found: C, 68.13; H, 4.43; N, 8.94.

1-(3-Chlorophenyl)-3-p-tolyl-1H-pyrazole-4-carboxylic acid (3b). To a solution of 2b (0.51 g, 1.72 mmol) dissolved in 16 mL of acetone, 5 mL of Jones' reagent was added. The reaction mixture was stirred at room temperature and monitored by TLC. The reaction mixture was poured into water and extracted with EtOAc. The combined organic layers were washed with water and brine, dried over Na$_2$SO$_4$, and concentrated in vacuo to afford 0.51 g (95%) of the title acid: mp 194.4° C. $^1$H NMR (CDCl$_3$) δ 8.57 (s, 1H), 7.86 (d, 1H), 7.77 (t, 2H), 7.66 (d, 1H), 7.44 (t, 1H), 7.34 (d, 1H), 7.28 (m, 2H), 2.41 (s, 3H). $^{13}$C NMR (CDCl$_3$) δ 168.8, 156.9, 147.7, 141.6, 140.3, 137.2, 134.7, 132.1, 130.6, 129.1, 121.3, 118.7, 22.8. Anal. Calcd for C$_{17}$H$_{13}$FC$_1$N$_2$O$_2$: C, 65.29; H, 4.19; N, 8.96. Found: C, 64.65; H, 3.37; N, 8.80.

1-(2,4-Dichlorophenyl)-3-p-tolyl-1H-pyrazole-4-carboxylic acid (3c). To a solution of 2c (0.53 g, 1.6 mmol) dissolved in 16 mL of acetone, 5 mL of Jones' reagent was added. The reaction mixture was stirred at room temperature and monitored by TLC. The reaction mixture was poured into water and extracted with EtOAc. The combined organic layers were washed with water and brine, dried over Na$_2$SO$_4$, and concentrated in vacuo to afford 0.51 g (91%) of the title acid: mp 211.7° C. $^1$H NMR (CDCl$_3$) δ 8.52 (s, 1H), 7.75 (d, 2H), 7.66 (d, 1H), 7.58 (s, 1H), 7.41 (d, 1H), 7.24 (d, 2H), 2.43 (s, 3H). $^{13}$C NMR (CDCl$_3$) δ 171.6, 155.7, 139.3, 131.9, 130.6, 130.2, 134.7, 132.1, 130.6, 129.8, 22.7. Anal. Calcd for C$_{17}$H$_{12}$C$_{12}$N$_2$O$_2$: C, 58.81; H, 3.48, N, 8.07. Found: C, 58.46; H, 3.40, N, 7.68.

3-(p-Tolyl)-1-(3-(trifluoromethyl)phenyl)-1H-pyrazole-4-carboxylic acid (3d). To a solution of 2d (0.79 g, 2.39 mmol) dissolved in 16 mL of acetone, 5 mL of Jones' reagent was added. The reaction mixture was stirred at room temperature and monitored by TLC. The reaction mixture was poured into water and extracted with EtOAc. The combined organic layers were washed with water and brine, dried over Na$_2$SO$_4$, and concentrated in vacuo to afford 0.81 g (98%) of the title acid: mp 181.8° C. $^1$H NMR (CDCl$_3$) δ 8.64 (s, 1H), 8.09 (s, 1H), 7.98 (d, 1H), 7.79 (d, 2H), 7.63 (d, 2H), 7.31 (t, 2H), 2.45 (s, 3H). $^{13}$C NMR (CDCl$_3$) δ 168.2, 155.7, 140.8, 140.5, 134.8, 131.7, 130.7, 130.2, 129.8, 125.5, 123.7, 117.9, 114.5, 22.8. Anal. Calcd for C$_{18}$H$_{13}$F$_3$N$_2$O$_2$: C, 62.43; H, 3.78; N, 8.09. Found: C, 61.95; H, 3.74; N, 7.62.

1-(Benzo[d]thiazol-2-yl)-3-(p-tolyl)-1H-pyrazole-4-carboxylic acid (3e). To a solution of 2e (0.71 g, 2.31 mmol) dissolved in 16 mL of acetone, 5 mL of Jones' reagent was added. The reaction mixture was stirred at room temperature and monitored by TLC. The reaction mixture was poured into water and extracted with EtOAc. The combined organic layers were washed with water and brine, dried over Na$_2$SO$_4$, and concentrated in vacuo to afford 0.41 g (57%) of the title acid: mp 208.0° C. $^1$H NMR (CDCl$_3$) δ 9.09 (s, 1H), 7.98 (d, 1H), 7.90 (d, 1H), 7.81 (d, 2H), 7.54 (d, 1H), 7.43 (d, 1H), 7.35 (d, 2H), 2.45 (s, 3H). $^{13}$C NMR (CDCl$_3$) δ 171.2, 160.1, 151.6, 141.3, 134.0, 131.3, 130.3, 129.0, 126.9, 124.2, 123.5, 23.0.

General Procedure of Mitsunobu Reaction

To a solution of 3 in CH$_2$Cl$_2$ was added EDCI and HOBT. The reaction mixture was stirred for 1-2 h. To the reaction were added 4-methyl-3-(morpholinosulfonyl)aniline and the reaction mixture was stirred at room temperature for overnight and quenched with water. Layers were separated and the aqueous layer was extracted with EtOAc. The combined organic solution was dried over Na$_2$SO$_4$ and then evaporated under a vacuum. The resulting yellow solids were purified by flash column chromatography to afford 4a-4e.

1-(4-fluorophenyl)-N-(4-methyl-3-(morpholinosulfonyl) phenyl)-3-p-tolyl-1H-pyrarazole-4-carboxamide (4a). To a solution of 3a (0.2 g, 0.67 mmol) in CH$_2$Cl$_2$ (10 mL) was added EDCI (0.22 g, 1.16 mmol) and HOBT (0.16 g, 1.16 mmol). The reaction mixture was stirred for 1 h. To the reaction were added 4-methyl-3-(morpholinosulfonyl)aniline (0.17 g, 0.68 mmol) and the reaction mixture was stirred at room temperature for 12 h and quenched with water. Layers were separated and the aqueous layer was extracted with EtOAc. The combined organic solution was dried over Na$_2$SO$_4$ and then evaporated under a vacuum. The resulting yellow solid was purified by flash column chromatography (H/EtOAc 1:1) to afford 4a as a white solid (0.09 g, 26% yield), mp 95.9° C. $^1$H NMR (CDCl$_3$) δ 8.52 (s, 1H), 7.73 (s, 1H), 7.72 (d, 2H), 7.64 (t, 2H), 7.54 (d, 2H), 7.36 (d, 2H), 7.27 (d, 3H), 3.72 (d, 4H), 3.17 (d, 4H), 2.57 (s, 3H), 2.47 (s, 3H). $^{13}$C NMR (CDCl$_3$) δ 162.1, 152.6, 141.4, 137.5, 137.4, 134.8, 134.6, 132.7, 131.2, 130.7, 130.2, 125.2, 122.7, 122.3, 119.5, 117.9, 117.7, 67.7, 46.8, 23.9, 22.6. Anal. Calcd for C$_{28}$H$_{27}$FN$_4$O$_4$S: C, 62.91; H, 5.09; N, 10.48; F, 3.55. Found: C, 62.75; H, 4.57; N, 10.46; F, 3.4.

1-(3-Chlorophenyl)-N-(4-methyl-3-(morpholinosulfonyl) phenyl)-3-(p-tolyl)-1H-pyrazole-4-carboxamide (4b). To a solution of 3b (0.2 g, 0.67 mmol) in CH$_2$Cl$_2$ (10 mL) was added EDCI (0.22 g, 1.16 mmol) and HOBT (0.15 g, 1.16 mmol). The reaction mixture was stirred for 1 h. To the reaction were added 4-methyl-3-(morpholinosulfonyl)aniline (0.17 g, 0.68 mmol) and the reaction mixture was stirred at room temperature for 12 h and quenched with water. The organic layer was collected and the aqueous layer was extracted with EtoAc. The combined organic solution was dried over Na$_2$SO$_4$, evaporated under a vacuum. The resulting yellow solid was purified by flash column chromatography (H/EtOAc 1:1) to afford 4b as a white solid (0.07 g, 19% yield), mp 204.9° C. $^1$H NMR (CDCl$_3$) δ 8.60 (s, 1H), 7.88 (s, 1H), 7.72 (d, 1H), 7.62 (m, 3H), 7.45 (d, 2H), 7.41 (m, 3H), 7.24 (d, 2H), 3.75 (d, 4H), 3.21 (d, 4H), 2.59 (s, 3H), 2.50 (s, 3H). $^{13}$C NMR (CDCl$_3$) δ 162.1, 152.7, 147.6, 141.7, 137.9, 134.8, 132.8, 132.0, 131.3, 130.7, 128.9, 125.1, 122.3, 121.3, 118.5, 67.7, 64.9, 23.0, 21.5, Anal. Calcd for C$_{28}$H$_{27}$ClN$_4$O$_4$S: C, 61.03; H, 4.94; N, 10.17; Cl, 6.43. Found: C, 60.78; H, 4.61; N, 9.94; Cl, 6.7.

1-(2,4-Dichlorophenyl)-N-(4-methyl-3-(morpholinosulfonyl)phenyl)-3-(p-tolyl)-1H-pyrazole-4-carboxamide (4c). To a solution of 3c (0.2 g, 0.58 mmol) in CH$_2$Cl$_2$ (5 mL) was added EDCI (0.22 g, 1.16 mmol) and HOBT (0.16 g, 1.16 mmol). The reaction mixture was stirred for 1 h. To the reaction were added 4-methyl-3-(morpholinosulfonyl)aniline (0.15 g, 0.58 mmol) and the reaction mixture was stirred at room temperature for 12 h and quenched with water. The organic layer was collected and the aqueous layer was extracted with EtoAc. The combined organic solution was dried over Na$_2$SO$_4$, evaporated under a vacuum. The resulting yellow solid was purified by flash column chromatography (H/EtOAc 1:1) to afford 4c as a white solid (0.06 g, 20% yield), mp 99.8° C. $^1$H NMR (CDCl$_3$) δ 8.52 (s, 1H), 7.73 (s, 1H), 7.62 (m, 3H), 7.45 (d, 2H), 7.38 (m, 3H), 7.24 (d, 2H), 3.73 (d, 4H), 3.19 (d, 4H), 2.57 (s, 3H), 2.46 (s, 3H). $^{13}$C NMR (CDCl$_3$) δ 162.0, 152.6, 141.9, 139.9, 137.7, 134.7, 134.3, 132.0, 131.3, 130.8, 129.5, 127.4, 125.2, 122.0, 118.3, 116.6, 67.7, 46.8, 22.9, 21.8. Anal. Calcd for C$_{28}$H$_{26}$Cl$_2$N$_4$O$_4$S: C, 57.44; H, 4.48; N, 9.57; Cl, 12.22. Found: C, 57.11; H, 4.27; N, 8.91; Cl, 12.2.

N-(4-Methyl-3-(morpholinosulfonyl)phenyl)-3-(p-tolyl)-1-(3-(trifluoromethyl) phenyl)-1H-pyrazole-4-carboxamide (4d). To a solution of 3d (0.2 g, 0.58 mmol) in CH$_2$Cl$_2$ (10 mL) was added EDCI (0.34 g, 1.76 mmol) and HOBT (0.24 g, 1.76 mmol). The reaction mixture was stirred for 1 h. To the reaction were added 4-methyl-3-(morpholinosulfonyl) aniline (0.2 g, 0.78 mmol) and the reaction mixture was stirred at room temperature for 16 h and quenched with water. The organic layer was collected and the aqueous layer was extracted with EtOAc. The combined organic solution was dried over Na$_2$SO$_4$, evaporated under a vacuum. The resulting yellow solid was purified by flash column chromatography (H/EtOAc 1:1) to afford 4d as a white solid (0.1 g, 31% yield), mp 192.7° C. $^1$H NMR (CDCl$_3$) δ 8.67 (s, 1H), 8.12 (s, 1H), 7.92 (d, 1H), 7.72 (s, 1H), 7.64 (d, 4H), 7.51 (t, 3H), 7.41 (d, 2H), 3.74 (d, 4H), 3.19 (d, 4H), 2.58 (s, 3H), 2.50 (s, 3H). $^{13}$C NMR (CDCl$_3$) δ 165.0, 151.6, 141.9, 139.9, 137.7, 134.7, 134.3, 132.0, 131.3, 130.8, 129.5, 127.4, 125.2, 124.1, 118.3, 116.6, 67.8, 46.9, 23.9, 23.6. Anal. Calcd for C$_{29}$H$_{27}$F$_3$N$_4$O$_4$S: C, 59.58; H, 4.66; N, 9.58; F, 9.75. Found: C, 60.07; H, 4.38; N, 9.53; F, 10.

1-(Benzo[d]thiazol-2-yl)-N-(4-methyl-3-(morpholinosulfonyl)phenyl)-3-(p-tolyl)-1H-pyrazole-4-carboxamide (4e). To a solution of 3e (0.2 g, 0.59 mmol) in CH$_2$Cl$_2$ (5 mL) was added EDCI (0.14 g, 0.71 mmol) and HOBT (0.1 g, 0.7 mmol). The reaction mixture was stirred for 1 h. To the reaction were added 4-methyl-3-(morpholinosulfonyl)aniline (0.15 g, 0.59 mmol) and the reaction mixture was stirred at room temperature for 12 h and quenched with water. The organic layer was collected and the aqueous layer was extracted with EtOAc. The combined organic solution was dried over Na$_2$SO$_4$, evaporated under a vacuum. The resulting yellow oil was purified by flash column chromatography (H/EtOAc 1:1) to afford 4e as a pale-yellow solid (0.07 g, 21% yield), mp 153.1° C. $^1$H NMR (CDCl$_3$) δ 8.51 (s, 1H), 8.02 (s, 1H), 7.97 (d, 2H), 7.79 (d, 1H), 7.71 (t, 2H), 7.55 (t, 1H), 7.40 (dd, 4H), 3.74 (d, 4H), 3.19 (d, 4H), 2.63 (s, 3H), 2.44 (s, 3H). $^{13}$C NMR (CDCl$_3$) δ 165.0, 159.6, 144.5, 135.4, 137.7, 131.3, 131.0, 130.7, 130.2, 128.5, 126.1, 123.1, 123.0, 67.7, 47.7, 23.0, 21.7. Anal. Calcd for C$_{29}$H$_{27}$N$_5$O$_4$S$_2$: C, 60.71; H, 4.74; N, 12.21. Found: C, 60.57; H, 4.2; N, 12.6.

General Procedure of Mitsunobu Reaction for Producing 4f-4s

To a solution of 7 in CH$_2$Cl$_2$ was added EDCI and DMAP. To the reaction was added 4-methyl-3-(morpholinosulfonyl) aniline and the reaction mixture was stirred at room temperature for 6 h and quenched with water and then treated with 10% HCl. The organic layer was collected and the aqueous layer was extracted with EtOAc. The combined organic solution was dried over Na$_2$SO$_4$, evaporated under a vacuum. The resulting yellow oil was purified by flash column chromatography to afford 4f-4s.

1-Isopropyl-N-(4-methyl-3-(morpholinosulfonyl)phenyl)-3-(p-tolyl)-1H-pyrazole-4-carboxamide (4f). To a solution of 7-1 (0.11 g, 0.43 mmol) in CH$_2$Cl$_2$ (5 mL) was added EDCI (0.14 g, 0.73 mmol) and DMAP (0.09 g, 0.73 mmol). To the reaction was added 4-methyl-3-(morpholinosulfonyl)aniline (0.11 g, 0.43 mmol) and the reaction mixture was stirred at room temperature for 6 h and quenched with water and then treated with 10% HCl. The organic layer was collected and the aqueous layer was extracted with EtOAc. The combined organic solution was dried over Na$_2$SO$_4$, evaporated under a vacuum. The resulting yellow oil was purified by flash column chromatography (H/EtOAc 1:1) to afford 4f as a white solid (0.11 g, 50% yield), mp 198.2° C. $^1$H NMR (CDCl$_3$) δ 8.13 (s, 1H), 7.69 (s, 1H), 7.54 (d, 2H), 7.44 (d, 2H), 7.35 (d, 2H), 7.26 (d, 1H), 4.55 (m, 1H), 3.74 (d, 4H), 3.17 (d, 4H), 2.56 (s, 3H), 2.46 (s, 3H), 1.59 (d, 6H). $^{13}$C NMR (CDCl$_3$) δ 163.2, 145.3, 140.8, 135.2, 134.7, 130.3, 130.1, 126.1, 121.8, 120.9, 117.9, 109.9, 67.7, 56.5, 46.7, 24.1, 22.9, 21.1. Anal. Calcd for C$_{25}$H$_{30}$N$_4$O$_4$S. ½ H$_2$O: C, 61.07; H, 6.15; N, 11.39. Found: C, 61.26; H, 6.31; N, 11.29.

1-Butyl-N-(4-methyl-3-(morpholinosulfonyl)phenyl)-3-(p-tolyl)-1H-pyrazole-4-carboxamide (4g). To a solution of 7-2 (0.2 g, 0.77 mmol) in CH$_2$Cl$_2$ (10 mL) was added EDCI (0.18 g, 0.92 mmol) and HOBT (0.12 g, 0.92 mmol). The reaction mixture was stirred for 1 h. To the reaction were added 4-methyl-3-(morpholinosulfonyl)aniline (0.2 g, 0.77 mmol) and the reaction mixture was stirred at room temperature for 12 h and quenched with water. The organic layer was collected and the aqueous layer was extracted with EtOAc. The combined organic solution was dried over Na$_2$SO$_4$, evaporated under a vacuum. The resulting yellow oil was purified by flash column chromatography (H/EtOAc 1:1) to afford 4g as a white solid (0.2 g, 53% yield), mp 177.4° C. $^1$H NMR (CDCl$_3$) δ 8.07 (s, 1H), 7.69 (s, 1H), 7.54 (d, 2H), 7.44 (d, 2H), 7.35 (d, 2H), 7.23 (s, 1H), 4.18 (m, 2H), 3.74 (d, 4H), 3.17 (d, 4H), 2.56 (s, 3H), 2.46 (s, 3H), 1.92 (t, 2H), 1.41 (t, 2H), 0.98 (t, 3H). $^{13}$C NMR (CDCl$_3$) δ 162.7, 151.3, 140.9, 137.6, 134.8, 131.7, 131.5, 130.7, 125.2, 122.1, 120.9, 116.9, 67.7, 53.9, 46.8, 33.5, 22.8, 21.4, 21.1, 14.9. Anal. Calcd for C$_{26}$H$_{32}$N$_4$O$_4$S: C, 62.88; H, 6.49; N, 11.28. Found: C, 62.65; H, 6.27; N, 11.08.

N-(4-Methyl-3-(morpholinosulfonyl)phenyl)-1-(naphthalen-2-ylmethyl)-3-(p-tolyl)-1H-pyrazole-4-carboxamide (4h). To a solution of 7-3 (0.2 g, 0.78 mmol) in CH$_2$Cl$_2$ (10 mL) was added EDCI (0.18 g, 0.94 mmol) and DMAP (0.11 g, 0.94 mmol). To the reaction was added 4-methyl-3-(morpholinosulfonyl)aniline (0.2 g, 0.78 mmol) in one portion and the reaction mixture was stirred at room temperature for 6 h and then treated with 10% HCl. The organic layer was collected and the aqueous layer was extracted with EtOAc. The combined organic solution was dried over Na$_2$SO$_4$, evaporated under a vacuum. The resulting yellow oil was purified by flash column chromatography (H/EtOAc 1:1) to afford 4g as a white solid (0.2 g, 50% yield), mp 144.9° C. $^1$H NMR (CDCl$_3$) δ 8.13 (s, 1H), 7.85 (m, 4H), 7.68 (s, 1H), 7.53 (m, 4H), 7.45 (m, 2H), 7.35 (d, 2H), 7.20 (d, 2H), 5.51 (s, 2H), 3.72 (t, 4H), 3.15 (t, 4H), 2.51 (s, 3H), 2.46 (s, 3H). $^{13}$C NMR (CDCl$_3$) δ 162.2, 151.2, 141.2, 137.4, 136.9, 135.6, 134.8, 133.7, 131.3, 130.8, 130.4, 129.4, 129.2, 129.1, 128.1, 127.1, 125.1, 122.1, 67.8, 58.4, 46.9, 22.9, 21.6. Anal. Calcd for C$_{33}$H$_{32}$N$_4$O$_4$S: C, 68.25; H, 5.55; N, 9.65. Found: C, 68.00; H, 6.04; N, 9.48.

1-(Cyclopropylmethyl)-N-(4-methyl-3-(morpholinosulfonyl)phenyl)-3-(p-tolyl)-1H-pyrazole-4-carboxamide (4i). To a solution of 7-4 (0.2 g, 0.78 mmol) in CH$_2$Cl$_2$ (10 mL) was added EDCI (0.18 g, 0.94 mmol) and DMAP (0.11 g, 0.94 mmol). To the reaction was added 4-methyl-3-(morpholinosulfonyl)aniline (0.2 g, 0.78 mmol) in one portion and the reaction mixture was stirred at room temperature for 6 h and then treated with 10% HCl. The organic layer was collected and the aqueous layer was extracted with EtOAc. The combined organic solution was dried over Na$_2$SO$_4$, evaporated under a vacuum. The resulting yellow solid was purified by crystallization from EtOAc gave 4i as a white solid (0.3 g, 78% yield), mp 210.0° C. $^1$H NMR (CDCl$_3$) δ 8.23 (s, 1H), 7.71 (d, 1H), 7.54 (d, 2H), 7.46 (d, 2H), 7.35 (d, 2H), 7.21 (d, 1H), 4.05 (d, 2H), 3.74 (t, 4H), 3.17 (t, 4H), 2.51 (s, 3H), 1.36 (brs, 1H), 0.74 (q, 2H), 0.45 (t, 2H). $^{13}$C NMR (CDCl$_3$) δ 162.5, 150.8, 141.0, 137.6, 137.1, 131.3, 130.8, 125.0, 122.1, 67.8, 58.9, 46.9, 23.2, 21.9, 12.0, 5.6. Anal. Calcd for C$_{26}$H$_{30}$N$_4$O$_4$S.¼ H$_2$O: C, 61.98; H, 6.00; N, 11.02. Found: C, 61.63; H, 5.82; N, 10.84.

1-(3-Methoxybenzyl)-N-(4-methyl-3-(morpholinosulfonyl)phenyl)-3-(p-tolyl)-1H-pyrazole-4-carboxamide (4j, DY268). To a solution of 7-5 (0.1 g, 0.31 mmol) in CH$_2$Cl$_2$ (8 mL) was added EDCI (0.071 g, 0.37 mmol) and DMAP (0.045 g, 0.37 mmol). To the reaction was added 4-methyl-3-(morpholinosulfonyl)aniline (0.08 g, 0.31 mmol) in one portion and the reaction mixture was stirred at room temperature for 6 h and then treated with 10% HCl. The organic layer was collected and the aqueous layer was extracted with EtOAc. The combined organic solution was dried over Na₂SO₄, evaporated under a vacuum. The resulting yellow oil was purified by flash column chromatography (H/EtOAc 1:1) to afford 4j as a white solid (0.08 g, 47% yield), mp 183.3° C. $^1$H NMR (CDCl₃) δ 8.01 (s, 1H), 7.69 (s, 1H), 7.55 (d, 2H), 7.44 (d, 2H), 7.34 (m, 3H), 7.22 (d, 2H), 6.93 (d, 1H), 6.87 (s, 1H), 5.32 (s, 2H), 3.85 (s, 3H), 3.74 (t, 4H), 3.17 (t, 4H), 2.56 (s, 3H), 2.46 (s, 3H). $^{13}$C NMR (CDCl₃) δ 162.6, 160.0, 141.4, 137.1, 135.5, 134.8, 131.5, 131.3, 130.8, 125.1, 122.1, 115.5, 115.4, 67.7, 58.0, 56.7, 46.8, 22.8, 21.6. Anal. Calcd for C₃₀H₃₂N₄O₅S: C, 64.27; H, 5.75; N, 9.99. Found: C, 64.01; H, 5.77; N, 9.63.

N-(4-methyl-3-(morpholinosulfonyl)phenyl)-3-(p-tolyl)-1-(3-(trifluoromethyl)benzyl)-1H-pyrazole-4-carboxamide (4k). To a solution of 7-6 (0.11 g, 0.34 mmol) in CH₂Cl₂ (5 mL) was added EDCI (0.078 g, 0.41 mmol) and DMAP (0.05 g, 0.41 mmol). To the reaction was added 4-methyl-3-(morpholinosulfonyl)aniline (0.087 g, 0.34 mmol) in one portion and the reaction mixture was stirred at room temperature for 6 h and then treated with 10% HCl. The organic layer was collected and the aqueous layer was extracted with EtOAc. The combined organic solution was dried over Na₂SO₄, evaporated under a vacuum. The resulting yellow solid was purified by crystallization from EtOAc gave 4k as a white solid (0.1 g, 56% yield), mp 179.3° C. $^1$H NMR (CDCl₃) δ 8.07 (s, 1H), 7.68 (s, 1H), 7.59 (s, 1H), 7.51 (t, 4H), 7.45 (t, 2H), 7.43 (d, 2H), 7.21 (d, 2H), 5.41 (s, 2H), 3.72 (t, 4H), 3.15 (t, 4H), 2.51 (s, 3H), 2.46 (s, 3H). $^{13}$C NMR (CDCl₃) δ 162.4, 151.6, 141.4, 137.3, 135.7, 134.8, 134.6, 132.8, 131.3, 130.8, 126.2, 125.1, 122.2, 118.4, 67.7, 57.4, 46.8, 22.8, 21.6. Anal. Calcd for C₃₀H₂₉F₃N₄O₄S: C, 60.19; H, 4.88; N, 9.36, F, 9.52. Found: C, 60.45; H, 4.70; N, 9.15, F, 9.20.

1-(4-Hydroxybutyl)-N-(4-methyl-3-(morpholinosulfonyl)phenyl)-3-(p-tolyl)-1H-pyrazole-4-carboxamide (4l). To a solution of 7-7 (0.09 g, 0.34 mmol) in CH₂Cl₂ (5 mL) was added EDCI (0.078 g, 0.41 mmol) and DMAP (0.05 g, 0.41 mmol). To the reaction was added 4-methyl-3-(morpholinosulfonyl)aniline (0.087 g, 0.34 mmol) in one portion and the reaction mixture was stirred at room temperature for 6 h and then treated with 10% HCl. The organic layer was collected and the aqueous layer was extracted with EtOAc. The combined organic solution was dried over Na₂SO₄, evaporated under a vacuum. The resulting yellow oil was purified by flash column chromatography (CHCl₃/MeOH 95:5) to afford 4l as a white solid (0.05 g, 27% yield), mp 57.8° C. $^1$H NMR (CDCl₃) δ 8.01 (s, 1H), 7.68 (s, 1H), 7.50 (d, 2H), 7.49 (t, 1H), 7.15 (t, 4H), 4.21 (d, 2H), 4.20 (d, 2H), 3.72 (t, 4H), 3.11 (t, 4H), 2.51 (s, 3H), 2.46 (s, 3H), 1.94 (t, 2H), 1.26 (t, 2H). $^{13}$C NMR (CDCl₃) δ 162.2, 154.9, 141.3, 139.8, 137.6, 135.2, 134.8, 131.8, 131.3, 130.6, 129.9, 125.2, 122.3, 67.7, 63.3, 53.8, 46.8, 30.7, 27.2, 21.6. Anal. Calcd for C₂₆H₃₂N₄O₄S: C, 60.71; H, 4.74; N, 12.21. Found: C, 60.57; H, 4.2; N, 12.26.

(Z)-Ethyl 3-ethoxy-2-(4-methylbenzoyl)acrylate (5-1)

Ethyl 3-oxo-3-(p-tolyl)propanoate (1.0 g, 4.85 mmol) and triethylorthoformate (1.15 g, 7.76 mmol) were heated to reflux and stirred for 30 min. Acetic anhydride (1.5 g, 14.55 mmol) was then added, and refluxing continued for about 12 h. Then the mixture was cooled and diluted with EtOAc and water was added to the solution, which was then stirred for 10 min to decompose excess triethylorthoformate. The aqueous layer was extracted with EtOAc. The organic layers were washed with water, brine, dried over Na₂SO₄ and concentrated in vacuo to yield 1.21 g (94%) of the title compound which was used without further purification. $^1$H NMR (CDCl₃) δ 7.82 (d, 2H), 7.69 (s, 1H), 7.27 (d, 2H), 4.17 (q, 2H), 4.11 (q, 2H), 2.40 (s, 3H), 1.28 (t, 3H), 1.17 (t, 3H). $^{13}$C NMR (CDCl₃) δ 192.9, 162.7, 145.5, 136.2, 130.8, 130.5, 130.3, 113.7, 73.1, 61.9, 23.1, 16.6, 15.6.

(Z)-Ethyl 2-(ethoxymethylene)-4-methyl-3-oxopentanoate (5-2)

Ethyl isobutyryl acetate (2.0 g, 12.64 mmol) and triethylorthoformate (3.0 g, 20.22 mmol) were heated to reflux for 30 min. Acetic anhydride (3.8 g, 37.92 mmol) was then added, and refluxing continued for about 12 h. The reaction mixture was cooled and diluted with EtOAc and water was added to the solution, which was then stirred for 10 min to decompose excess triethylorthoformate. The aqueous layer was extracted with EtOAc. The organic layers were washed with water, brine, dried over Na₂SO₄ and concentrated in vacuo to yield 2.49 g (92%) of the title compound which was used without further purification. $^1$H NMR (CDCl₃) δ 7.52 (s, 1H), 4.29 (q, 2H), 4.19 (q, 2H), 3.14 (m, 1H), 1.37 (t, 3H), 1.32 (t, 3H), 1.16 (s, 3H), 1.11 (s, 3H). $^{13}$C NMR (CDCl₃) δ 203.4, 165.8, 163.1, 114.7, 73.4, 62.2, 42.1, 20.2, 19.3, 16.6, 15.6.

(Z)-Ethyl 3-ethoxy-2-(3-methoxybenzoyl)acrylate (5-3)

Ethyl (3-methoxybenzoyl) acetate (1.0 g, 4.5 mmol) and triethylorthoformate (1.07 g, 7.2 mmol) were heated to reflux for 30 min. Acetic anhydride (1.37 g, 13.5 mmol) was then added, and refluxing continued for about 12 h. The reaction mixture was cooled and diluted with EtOAc and water was added to the solution, which was then stirred for 10 min to decompose excess triethylorthoformate. The aqueous layer was extracted with EtOAc. The organic layers were washed with water, brine, dried over Na₂SO₄ and concentrated in vacuo to yield 1.1 g (88%) of the title compound which was used without further purification. $^1$H NMR (CDCl₃) δ 7.68 (s, 1H), 7.47 (t, 2H), 7.35 (t, 1H), 7.11 (t, 1H), 4.17 (q, 2H), 4.11 (q, 2H), 1.16 (t, 3H), 1.06 (t, 3H). $^{13}$C NMR (CDCl₃) δ 193.3, 167.1, 162.9, 161.2, 140.1, 130.7, 130.5, 123.7, 121.4, 114.1, 73.2, 62.0, 56.8, 16.6, 15.6.

(Z)-Ethyl 3-ethoxy-2-(3-(trifluoromethyl)benzoyl)acrylate (5-4). Ethyl (4-trifluoromethylbenzoyl) acetate (1.0 g, 3.84 mmol) and triethylorthoformate (0.91 g, 6.15 mmol) were heated to reflux for 30 min. Acetic anhydride (1.18 g, 11.53 mmol) was then added, and refluxing continued for about 12 h. The reaction mixture was cooled and diluted with EtOAc and water was added to the solution, which was then stirred for 10 min to decompose excess triethylorthoformate. The aqueous layer was extracted with EtOAc. The organic layers were washed with water, brine, dried over Na₂SO₄ and concentrated in vacuo to yield 1.08 g (89%) of the title compound which was used without further purification. $^1$H NMR (CDCl₃) δ 8.06 (d, 1H), 7.97 (d, 1H), 7.87 (s, 1H), 7.74 (d, 2H), 4.16 (q, 2H), 4.11 (q, 2H), 1.27 (t, 6H). $^{13}$C NMR (CDCl₃) δ 193.2, 164.1, 130.7, 130.3, 127.8, 127.3, 126.8, 114.1, 73.6, 62.1, 16.6, 15.5.

(Z)-Methyl 2-(ethoxymethylene)-5-methoxy-3-oxopentanoate (5-5). Methyl 5-methoxy-3-oxovalerate (2.0 g, 12.48 mmol) and triethylorthoformate (3.0 g, 19.96 mmol) were heated to reflux for 30 min. Acetic anhydride (3.82 g, 37.44 mmol) was then added, and refluxing continued for about 6 h. The reaction mixture was cooled and diluted with EtOAc and water was added to the solution, which was then stirred for 10 min to decompose excess triethylorthoformate. The aqueous layer was extracted with EtOAc. The organic layers were washed with water, brine, dried over $Na_2SO_4$ and concentrated in vacuo to yield 2.27 g (84%) of the title compound which was used without further purification. $^1H$ NMR (CDCl$_3$) δ 7.90 (s, 1H), 4.25 (q, 2H), 3.66 (t, 2H), 3.35 (s, 3H), 3.23 (t, 2H), 1.31 (t, 3H). $^{13}C$ NMR (CDCl$_3$) δ 200.5, 185.9, 165.7, 108.1, 67.7, 67.6, 60.3, 51.4, 38.8, 15.2.

Ethyl 3-(p-tolyl)-1H-pyrazole-4-carboxylate (6-1)

A solution of hydrazine monohydrate (0.2 ml, 4.2 mmol) in dry ethanol (1 ml) was added dropwise at 0° C. to a solution of (Z)-Ethyl 3-ethoxy-2-(4-methylbenzoyl)acrylate (5-1) (1.0 g, 3.81 mmol) in ethanol (5 ml). The reaction mixture was stirred at rt for 12 h and the resulting solid was filtered, washed with water and cold ethanol, and dried to afford 0.77 g (88%) of 6-1 as a white solid, mp 83.5° C. $^1H$ NMR (CDCl$_3$) δ 8.04 (s, 1H), 7.59 (d, 2H), 7.27 (d, 2H), 4.27 (q, 2H), 2.40 (s, 3H), 1.31 (t, 3H). $^{13}C$ NMR (CDCl$_3$) δ 164.8, 149.3, 142.8, 140.8, 130.4, 130.3, 127.9, 113.1, 61.6, 22.8, 15.7.

Ethyl 3-isopropyl-1H-pyrazole-4-carboxylate (6-2)

A solution of hydrazine monohydrate (0.67 g, 13.40 mmol) in dry ethanol (1 ml) was added dropwise at 0° C. to a solution of (Z)-ethyl 2-(ethoxymethylene)-4-methyl-3-oxopentanoate (5-2) (2.49 g, 11.62 mmol) in ethanol (10 ml). The reaction mixture was stirred at rt for 12 h and the solvent was removed, solidified by pet. ether to afford 1.28 g (61%) of 6-2 as a white solid, mp 71.5° C. $^1H$ NMR (CDCl$_3$) δ 11.46 (brs, 1H), 7.96 (s, 1H), 4.32 (q, 2H), 3.69 (m, 1H), 1.36 (s, 6H), 1.33 (t, 3H). $^{13}C$ NMR (CDCl$_3$) δ 165.1, 142.1, 111.6, 61.3, 27.1, 22.9, 15.8.

Ethyl 3-(3-methoxyphenyl)-1H-pyrazole-4-carboxylate (6-3)

A solution of hydrazine monohydrate (0.22 g, 4.35 mmol) in dry ethanol (1 ml) was added dropwise at 0° C. to a solution of (Z)-ethyl 3-ethoxy-2-(3-methoxybenzoyl)acrylate (5-3) (1.1 g, 3.95 mmol) in ethanol (5 ml). The reaction mixture was stirred at rt for 12 h and the solvent was removed. The crude was resolved in EtOAc, washed with water, and concentrated to afford 0.97 g (98%) of 6-3 as a red oil which was used without further purification. $^1H$ NMR (CDCl$_3$) δ 8.05 (s, 1H), 7.36 (t, 1H), 7.29 (t, 3H), 6.98 (d, 1H), 4.28 (q, 2H), 3.81 (s, 3H), 1.30 (t, 3H). $^{13}C$ NMR (CDCl$_3$) δ 164.6, 160.7, 141.6, 132.2, 130.7, 122.8, 116.5, 116.2, 112.8, 61.6, 56.8, 15.7.

Ethyl 3-(4-(trifluoromethyl)phenyl)-1H-pyrazole-4-carboxylate (6-4). A solution of hydrazine monohydrate (0.22 g, 4.35 mmol) in dry ethanol (1 ml) was added dropwise at 0° C. to a solution of (Z)-ethyl 3-ethoxy-2-(3-methoxybenzoyl)acrylate (5-4) (1.08 g, 3.41 mmol) in ethanol (5 ml). The reaction mixture was stirred at rt for 12 h and the solvent was removed. The crude was resolved in EtOAc, washed with water, and concentrated to afford a red oil which was solidified by EtOAc to give 0.79 g (82%) of 6-4 as a pale red solid, mp 177.2° C. $^1H$ NMR (MeOD) δ 8.12 (s, 1H), 7.84 (d, 2H), 7.67 (d, 2H), 4.28 (q, 2H), 1.29 (t, 3H). $^{13}C$ NMR (MeOD) δ 164.7, 136.1, 131.2, 131.1, 130.7, 127.4, 126.7, 126.2, 125.7, 112.6, 61.4, 14.4.

Methyl 3-(2-methoxyethyl)-1H-pyrazole-4-carboxylate (6-5). A solution of hydrazine monohydrate (0.57 g, 11.54 mmol) in dry ethanol (1 ml) was added dropwise at 0° C. to a solution of (Z)-methyl 2-(ethoxymethylene)-5-methoxy-3-oxopentanoate (5-5) (2.27 g, 10.49 mmol) in ethanol (7 ml). The reaction mixture was stirred at rt for 12 h and the solvent was removed. The crude was resolved in EtOAc, washed with water, and concentrated to afford a red oil which was solidified by EtOAc to give 1.72 g (89%) of 6-5 as a yellow oil. $^1H$ NMR (CDCl$_3$) δ 7.90 (s, 1H), 4.24 (q, 2H), 3.76 (s, 1H), 3.65 (t, 2H), 3.33 (s, 3H), 1.28 (t, 3H). $^{13}C$ NMR (CDCl$_3$) δ 165.2, 148.3, 141.5, 122.4, 72.1, 60.3, 52.5, 27.3.

1-Isopropyl-3-(p-tolyl)-1H-pyrazole-4-carboxylic acid (7-1). A solution of 6-1 (0.5 g, 2.17 mmol), 1-Bromo-2-methyl-propane (0.55 g, 3.25 mmol) and cesium carbonate (2.12 g, 6.51 mmol) in acetonitrile (10 ml) was stirred at room temperature for 16 hrs and the reaction was stopped. Water (10 ml) was added into the reaction mixture and the aqueous layer was extracted with ethyl acetate (3×15 ml). The combined organic layers were washed with brine (3×10 ml), dried over $Na_2SO_4$, filtered and concentrated to give crude. $^1H$ NMR (CDCl$_3$) δ 8.00 (s, 1H), 7.67 (d, 2H), 7.22 (d, 2H), 4.54 (m, 1H), 4.25 (q, 2H), 2.38 (s, 3H), 1.56 (d, 6H), 1.31 (t, 3H). The crude residue in ethanol (12 mL) was treated with 1N aqueous potassium hydroxide (7.5 mL) at 75° C. for 2.5 hours. The reaction was cooled, acidified with 5N HCl and the ethanol removed in vacuo. The solids were filtered, washed with water, hexanes and dried in vacuo to afford 0.31 g (58%) of 7-1 as a beige powder, mp 129.0° C. $^1H$ NMR (CDCl$_3$) δ 8.06 (s, 1H), 7.66 (d, 2H), 7.21 (d, 2H), 4.53 (m, 1H), 2.38 (s, 3H), 1.56 (d, 6H). $^{13}C$ NMR (CDCl$_3$) δ 169.8, 154.6, 139.7, 134.6, 131.0, 130.6, 130.1, 55.9, 24.1, 24.0, 22.9.

1-Butyl-3-(p-tolyl)-1H-pyrazole-4-carboxylic acid (7-2). A solution of 6-1 (0.5 g, 2.17 mmol), 1-Bromobutane (0.29 g, 3.25 mmol) and cesium carbonate (2.12 g, 6.51 mmol) in acetonitrile (10 ml) was stirred at room temperature for 16 hrs and the reaction was stopped. Water (10 ml) was added into the reaction mixture and the aqueous layer was extracted with ethyl acetate (3×15 ml). The combined organic layers were washed with brine (3×10 ml), dried over $Na_2SO_4$, filtered and concentrated. The crude residue in ethanol (12 mL) was treated with 1N aqueous potassium hydroxide (7.5 mL) at 75° C. for 3.5 hours. The reaction was cooled, acidified with 5N HCl and the ethanol removed in vacuo. Solvent was removed and the resulting yellow oil was purified by flash column chromatography (CHCl$_3$/MeOH 9:1) to afford 7-2 as pale-yellow oil (0.5 g, 50% yield). $^1H$ NMR (CDCl$_3$) δ 8.06 (s, 1H), 7.66 (d, 2H), 7.21 (d, 2H), 4.53 (m, 1H), 2.38 (s, 3H), 1.56 (d, 6H). $^{13}C$ NMR (CDCl$_3$) δ 169.8, 154.6, 139.7, 134.6, 131.0, 130.6, 130.1, 55.9, 24.1, 24.0, 22.9.

1-(Naphthalen-2-ylmethyl)-3-(p-tolyl)-1H-pyrazole-4-carboxylic acid (7-3). A solution of 6-1 (0.18 g, 0.78 mmol), 2-(bromomethyl)naphthalene (0.26 g, 1.17 mmol) and cesium carbonate (0.76 g, 2.34 mmol) in acetonitrile (5 ml) was stirred at room temperature for 16 hrs and the reaction was stopped. Water (10 ml) was added into the reaction mixture and the aqueous layer was extracted with ethyl acetate (3×15 ml). The combined organic layers were washed with brine (3×10 ml), dried over $Na_2SO_4$, filtered and concentrated. The crude residue in ethanol (10 mL) was treated with 1N aqueous potassium hydroxide (7.5 mL) at 75° C. for 3.5 hours. The reaction was cooled, acidified with 5N HCl and the ethanol removed in vacuo to afford 7-3 as a pale-yellow solid (0.2 g, 77% yield), mp 151.2° C. $^1H$ NMR (CDCl$_3$) δ 8.06 (s, 1H), 7.75 (m, 3H), 7.71 (d, 2H), 7.53 (d, 2H), 7.48 (m, 1H), 7.20 (m, 3H), 5.45 (s, 2H), 2.40

(s, 3H). $^{13}$C NMR (CDCl$_3$) δ 169.3, 155.2, 139.8, 134.7, 131.3, 130.6, 130.5, 130.4, 129.9, 129.7, 129.6, 129.3, 129.2, 129.1, 128.9, 128.0, 59.9, 22.8.

1-(Cyclopropylmethyl)-3-(p-tolyl)-1H-pyrazole-4-carboxylic acid (7-4). A solution of 6-1 (0.5 g, 2.17 mmol), bromomethylcyclopropane (0.43 g, 3.25 mmol) and cesium carbonate (2.12 g, 6.51 mmol) in acetonitrile (10 ml) was stirred at room temperature for 16 hrs and the reaction was stopped. Water (10 ml) was added into the reaction mixture and the aqueous layer was extracted with ethyl acetate (3×15 ml). The combined organic layers were washed with brine (3×10 ml), dried over Na$_2$SO$_4$, filtered and concentrated to give the crude. $^1$H NMR (CDCl$_3$) δ 8.09 (s, 1H), 7.68 (d, 2H), 7.26 (d, 2H), 4.24 (q, 2H), 4.02 (t, 2H), 2.42 (s, 3H), 1.33 (brs, 1H), 1.22 (t, 3H), 0.72 (t, 2H), 0.48 (t, 2H). The crude residue in ethanol (10 mL) was treated with 1N aqueous potassium hydroxide (7.5 mL) at 75° C. for 3.5 hours. The reaction was cooled, acidified with 5N HCl and the ethanol removed in vacuo. The solids were filtered, washed with water hexanes and dried over in vacuo to afford 7-4 as a pale-yellow solid (0.3 g, 55% yield), mp 142.6° C. $^1$H NMR (CDCl$_3$) δ 8.18 (s, 1H), 7.69 (d, 2H), 7.23 (d, 2H), 4.04 (d, 2H), 2.44 (s, 3H), 1.36 (brs, 1H), 0.74 (t, 2H), 0.44 (t, 2H). $^{13}$C NMR (CDCl$_3$) δ 169.7, 154.9, 143.7, 139.7, 136.6, 130.6, 130.5, 130.1, 112.0, 58.7, 22.8, 12.0, 5.5, 5.3.

1-(3-Methoxybenzyl)-3-(p-tolyl)-1H-pyrazole-4-carboxylic acid (7-5). A solution of 6-1 (0.1 g, 0.43 mmol), 3-methoxybenzyl bromide (0.13 g, 0.65 mmol) and cesium carbonate (0.42 g, 1.29 mmol) in acetonitrile (5 ml) was stirred at room temperature for 16 hrs and the reaction was stopped. Water (10 ml) was added into the reaction mixture and the aqueous layer was extracted with ethyl acetate (3×15 ml). The combined organic layers were washed with brine (3×10 ml), dried over Na$_2$SO$_4$, filtered and concentrated to give the crude. $^1$H NMR (CDCl$_3$) δ 8.05 (s, 1H), 7.90 (d, 2H), 7.24 (m, 3H), 6.89 (d, 2H). 6.84 (s, 1H), 5.29 (s, 2H), 4.21 (q, 2H), 3.75 (s, 3H), 2.41 (s, 3H), 1.21 (t, 3H). The crude residue in ethanol (5 mL) was treated with 1N aqueous potassium hydroxide (3.5 mL) at 75° C. for 3.5 hours. The reaction was cooled, acidified with 5N HCl and the ethanol removed in vacuo. The solids were filtered, washed with water hexanes and dried over in vacuo to afford 7e as a white solid (0.1 g, 77% yield), mp 169.6° C. $^1$H NMR (CDCl$_3$) δ 7.95 (s, 1H), 7.68 (d, 2H), 7.31 (t, 1H), 7.22 (t, 2H), 6.90 (d, 2H), 6.84 (s, 1H), 5.29 (b, 2H), 3.73 (s, 3H), 2.41 (s, 3H). $^{13}$C NMR (CDCl$_3$) δ 168.9, 155.2, 139.8, 137.3, 131.5, 131.2, 130.6, 130.5, 130.1, 121.8, 115.4, 115.3, 57.8, 56.7, 22.7.

3-(p-Tolyl)-1-(3-(trifluoromethyl)benzyl)-1H-pyrazole-4-carboxylic acid (7-6). A solution of 6-1 (0.1 g, 0.43 mmol), 3-(trifluoromethyl)benzyl bromide (0.15 g, 0.65 mmol) and cesium carbonate (0.42 g, 1.29 mmol) in acetonitrile (5 ml) was stirred at room temperature for 6 hrs and the reaction was stopped. Water (10 ml) was added into the reaction mixture and the aqueous layer was extracted with ethyl acetate (3×15 ml). The combined organic layers were washed with brine (3×10 ml), dried over Na$_2$SO$_4$, filtered and concentrated to give the crude. $^1$H NMR (CDCl$_3$) δ 7.97 (s, 1H), 7.68 (d, 2H), 7.58 (s, 1H), 7.51 (m, 3H). 7.23 (d, 2H), 5.39 (s, 2H), 4.26 (q, 2H), 2.41 (s, 3H), 1.26 (t, 3H). The crude residue in ethanol (5 mL) was treated with 1N aqueous potassium hydroxide (3.5 mL) at 75° C. for 5.5 hours. The reaction was cooled, acidified with 5N HCl and the ethanol removed in vacuo. The solids were filtered, washed with water hexanes and dried over in vacuo to afford 7f as a white solid (0.11 g, 77% yield), mp 149.9 OC. $^1$H NMR (CDCl$_3$) δ 8.01 (s, 1H), 7.67 (d, 2H), 7.52 (s, 1H), 7.49 (d, 2H), 7.21 (m, 3H), 5.39 (s, 2H), 2.41 (s, 3H). $^{13}$C NMR (CDCl$_3$) δ 169.2, 156.4, 143.9, 140.1, 137.65 132.7, 131.1, 130.7, 130.6, 130.1, 126.8, 126.2, 119.5, 118.5, 57.2, 22.7.

1-(4-Hydroxybutyl)-3-(p-tolyl)-1H-pyrazole-4-carboxylic acid (7-7). A solution of 6-1 (0.1 g, 0.43 mmol), 4-bromo-1-butanol (0.10 g, 0.65 mmol) and cesium carbonate (0.42 g, 1.29 mmol) in acetonitrile (5 ml) was stirred at room temperature for 6 hrs and the reaction was stopped. Water (10 ml) was added into the reaction mixture and the aqueous layer was extracted with ethyl acetate (3×15 ml). The combined organic layers were washed with brine (3×10 ml), dried over Na$_2$SO$_4$, filtered and concentrated to give the crude. $^1$H NMR (CDCl$_3$) δ 7.98 (s, 1H), 7.65 (d, 2H), 7.20 (d, 2H), 4.24 (q, 2H). 4.09 (t, 2H), 3.45 (t, 2H), 2.41 (s, 3H), 1.67 (t, 2H), 1.57 (t, 2H), 1.42 (t, 3H). The crude residue in ethanol (5 mL) was treated with 1N aqueous potassium hydroxide (3.5 mL) at 75° C. for 5.5 hours. The reaction was cooled; the ethanol was removed in vacuo, acidified with 5N HCl, and dried over in vacuo to afford 7-7 as an oil (0.09 g, 82% yield). $^1$H NMR (CDCl$_3$) δ 7.99 (s, 1H), 7.65 (d, 2H), 7.19 (d, 2H), 4.14 (q, 2H), 3.62 (t, 2H), 2.40 (s, 3H), 1.96 (t, 2H), 1.55 (t, 2H). $^{13}$C NMR (CDCl$_3$) δ 168.8, 154.9, 139.7, 137.3, 131.1, 130.6, 130.1, 130.7, 112.0, 63.1, 53.7, 30.5, 27.9, 22.8.

3-Isopropyl-1-(3-methoxybenzyl)-1H-pyrazole-4-carboxylic acid (7-8). A solution of 6-2 (0.5 g, 2.74 mmol), 3-methoxybenzyl bromide (0.83 g, 4.11 mmol) and cesium carbonate (2.68 g, 8.22 mmol) in acetonitrile (10 ml) was stirred at room temperature for 16 hrs and the reaction was stopped. Water (10 ml) was added into the reaction mixture and the aqueous layer was extracted with ethyl acetate (3×15 ml). The combined organic layers were washed with brine (3×10 ml), dried over Na$_2$SO$_4$, filtered and concentrated to give crude. $^1$H NMR (CDCl$_3$) δ 7.73 (s, 1H), 7.29 (d, 1H), 6.87 (t, 1H), 6.83 (d, 1H), 6.77 (s, 1H), 5.22 (s, 2H), 4.26 (q, 2H), 3.82 (s, 3H), 3.54 (m, 1H), 1.35 (d, 6H), 1.26 (t, 3H). The crude residue in ethanol (12 mL) was treated with 1N aqueous potassium hydroxide (7.5 mL) at 75° C. for 4.5 hours. The reaction was cooled, the ethanol was removed in vacuo, acidified with 5N HCl, and dried over in vacuo to afford 7-8 as an white solid (0.59 g, 78% yield), mp 111.9° C. $^1$H NMR (CDCl$_3$) δ 7.79 (s, 1H), 7.29 (t, 1H), 6.88 (d, 1H), 6.84 (d, 1H), 6.78 (s, 1H), 5.23 (s, 2H), 3.79 (s, 3H), 3.55 (m, 1H), 1.32 (d, 6H). $^{13}$C NMR (CDCl$_3$) δ 169.6, 163.0, 161.5, 138.0, 136.4, 131.4, 121.7, 115.3, 115.1, 111.8, 57.5, 56.7, 28.0, 23.3.

3-Isopropyl-1-(3-methoxybenzyl)-1H-pyrazole-4-carboxylic acid (7-9). A solution of 6-3 (0.3 g, 1.22 mmol), 2-iodopropane (0.31 g, 1.83 mmol) and cesium carbonate (1.19 g, 3.66 mmol) in acetonitrile (5 ml) was stirred at room temperature for 16 hrs and the reaction was stopped. Water (10 ml) was added into the reaction mixture and the aqueous layer was extracted with ethyl acetate (3×15 ml). The combined organic layers were washed with brine (3×10 ml), dried over Na$_2$SO$_4$, filtered and concentrated to give crude. $^1$H NMR (CDCl$_3$) δ 8.01 (s, 1H), 7.39 (d, 1H), 7.32 (t, 2H), 6.92 (d, 1H), 4.26 (q, 2H), 4.14 (m, 1H), 3.85 (s, 3H), 1.43 (d, 6H), 1.17 (t, 3H). $^{13}$C NMR (CDCl$_3$) δ 164.6, 161.6, 142.5, 133.5, 130.8, 123.5, 117.0, 116.1, 61.4, 56.7, 55.8, 51.9, 24.2, 15.7. The crude residue in ethanol (12 mL) was treated with 1N aqueous potassium hydroxide (7.5 mL) at 75° C. for 12 hours. The reaction was cooled; the ethanol was removed in vacuo, acidified with 5N HCl, and dried over in vacuo to afford 7-9 as a yellow oil (0.25 g, 78% yield). $^1$H NMR (CDCl$_3$) δ 8.08 (s, 1H), 7.39 (d, 2H), 7.32 (t, 1H), 6.95 (d, 1H), 4.51 (m, 1H), 3.85 (s, 3H), 1.58 (d, 6H).

$^{13}$C NMR (CDCl$_3$) δ 169.6, 160.6, 154.3, 143.5, 134.9, 134.7, 130.9, 123.3, 116.9, 115.9, 56.7, 55.9, 24.1, 24.0.

1-(3-Methoxybenzyl)-3-(3-methoxyphenyl)-1H-pyrazole-4-carboxylic acid (7-10). A solution of 6-3 (0.3 g, 1.22 mmol), benzyl-3-methoxybenzene (0.37 g, 1.83 mmol) and cesium carbonate (1.19 g, 3.66 mmol) in acetonitrile (5 ml) was stirred at room temperature for 6 hrs and the reaction was stopped. Water (10 ml) was added into the reaction mixture and the aqueous layer was extracted with ethyl acetate (3×15 ml). The combined organic layers were washed with brine (3×10 ml), dried over Na$_2$SO$_4$, filtered and concentrated to give crude. $^1$H NMR (CDCl$_3$) δ 7.92 (s, 1H), 7.39 (s, 1H), 7.32 (t, 3H), 6.94 (d, 3H), 6.84 (s, 1H), 5.31 (s, 2H), 4.24 (q, 2H), 3.85 (s, 3H), 3.76 (s, 3H), 1.86 (t, 3H). The crude residue in ethanol (12 mL) was treated with 1N aqueous potassium hydroxide (7.5 mL) at 75° C. for 12 hours. The reaction was cooled; the ethanol was removed in vacuo, acidified with 5N HCl, and dried over in vacuo to afford 7-10 as a yellow oil (0.27 g, 66% yield). $^1$H NMR (CDCl$_3$) δ 7.96 (s, 1H), 7.38 (d, 2H), 7.32 (t, 3H), 6.92 (d, 2H), 6.84 (s, 1H), 5.29 (s, 2H), 3.83 (s, 3H), 3.73 (s, 3H). $^{13}$C NMR (CDCl$_3$) δ 168.7, 160.6, 161.1, 143.5, 137.7, 137.4, 134.6, 131.5, 130.4, 123.2, 121.8, 116.2, 115.9, 115.4, 115.3, 57.9, 56.7.

1-Isopropyl-3-(4-(trifluoromethyl)phenyl)-1H-pyrazole-4-carboxylic acid (7-11). A solution of 6-4 (0.3 g, 1.06 mmol), 2-iodopropane (0.36 g, 1.83 mmol) and cesium carbonate (1.19 g, 3.66 mmol) in acetonitrile (5 ml) was stirred at room temperature for 6 hrs and the reaction was stopped. Water (10 ml) was added into the reaction mixture and the aqueous layer was extracted with ethyl acetate (3×15 ml). The combined organic layers were washed with brine (3×10 ml), dried over Na$_2$SO$_4$, filtered and concentrated to give crude. $^1$H NMR (CDCl$_3$) δ 8.00 (s, 1H), 7.92 (s, 1H), 7.93 (d, 2H), 7.64 (d, 2H), 4.25 (q, 2H), 4.10 (m, 1H), 1.61 (d, 6H), 1.28 (t, 3H). The crude residue in ethanol (10 mL) was treated with 2N aqueous potassium hydroxide (5.5 mL) at 75° C. for 12 hours. The reaction was cooled; the ethanol was removed in vacuo. The residue was taken up with EtOAc/water and acidified with 5N HCl to PH3. Organic phases were dried over Na$_2$SO$_4$, filtered and concentrated in vacuo to afford 7-11 as a yellow solid (0.21 g, 67% yield), mp 161.1° C. $^1$H NMR (CDCl$_3$) δ 10.17 (brs, 1H), 8.10 (s, 1H), 7.93 (d, 2H), 7.62 (d, 2H), 4.51 (brs, 1H), 1.52 (s, 6H). $^{13}$C NMR (CDCl$_3$) δ 168.1, 151.5, 143.9, 142.1, 135.9, 133.5, 132.7, 130.3, 129.6, 125.3, 54.7, 22.4, 22.3.

1-(3-Methoxybenzyl)-3-(4-(trifluoromethyl)phenyl)-1H-pyrazole-4-carboxylic acid (7-12). A solution of 6-4 (0.2 g, 0.7 mmol), 3-methoxy benzyl bromide (0.21 g, 1.05 mmol) and cesium carbonate (0.68 g, 2.1 mmol) in acetonitrile (5 ml) was stirred at room temperature for 12 hrs and the reaction was stopped. Water (10 ml) was added into the reaction mixture and the aqueous layer was extracted with ethyl acetate (3×15 ml). The combined organic layers were washed with brine (3×10 ml), dried over Na$_2$SO$_4$, filtered and concentrated to give crude. $^1$H NMR (CDCl$_3$) δ 7.96 (t, 2H), 7.66 (d, 2H), 7.29 (d, 2H), 6.88 (d, 2H), 6.83 (s, 1H), 5.28 (s, 2H), 4.23 (q, 2H), 3.79 (s, 3H), 1.26 (t, 3H). The crude residue in ethanol (5 mL) was treated with 2N aqueous potassium hydroxide (4 mL) at 75° C. for 12 hours. The reaction was cooled; the ethanol was removed in vacuo. The residue was taken up with EtOAc/water and acidified with 5N HCl to PH3. Organic phases were dried over Na$_2$SO$_4$, filtered and concentrated in vacuo to afford 7-12 as a yellow solid (0.21 g, 80% yield), mp 141.7° C. $^1$H NMR (CDCl$_3$) δ 7.92 (s, 1H), 7.87 (d, 2H), 7.23 (t, 1H), 6.84 (d, 2H), 6.77 (s, 1H), 5.24 (s, 2H), 3.74 (s, 3H). $^{13}$C NMR (CDCl$_3$) δ 166.1, 160.8, 159.6, 142.4, 139.2, 135.9, 135.6, 130.0, 129.5, 129.1, 125.4, 119.8, 113.6, 113.0, 112.7, 64.8, 55.0.

3-Isopropyl-1-(3-methoxybenzyl)-N-(4-methyl-3-(morpholinosulfonyl)phenyl)-1H-pyrazole-4-carboxamide (4m, DY271). To a solution of 7-8 (0.12 g, 0.44 mmol) in CH$_2$Cl$_2$ (5 mL) was added EDCI (0.1 g, 0.53 mmol) and DMAP (0.07 g, 0.53 mmol). To the reaction was added 4-methyl-3-(morpholinosulfonyl)aniline (0.11 g, 0.44 mmol) in one portion and the reaction mixture was stirred at room temperature for 6 h and then treated with 10% HCl. The organic layer was collected and the aqueous layer was extracted with EtOAc. The combined organic solution was dried over Na$_2$SO$_4$, evaporated under a vacuum. The resulting yellow oil was purified by flash column chromatography (H/EtOAc 1:1) to afford 4m as a white solid (0.18 g, 83% yield), mp 179.7° C. $^1$H NMR (CDCl$_3$) δ 8.10 (s, 1H), 7.79 (dd, 3H), 7.31 (m, 2H), 6.83 (t, 2H), 6.82 (s, 1H), 5.28 (s, 2H), 3.81 (s, 3H), 3.66 (t, 4H), 3.59 (m, 1H), 3.11 (t, 4H), 2.60 (s, 3H), 1.39 (d, 6H). $^{13}$C NMR (CDCl$_3$) δ 163.2, 161.2, 160.0, 138.8, 138.5, 136.3, 134.5, 135.1, 131.8, 131.4, 126.1, 122.6, 122.7, 121.7, 115.2, 115.1, 67.6, 57.4, 56.7, 46.8, 28.4, 23.6, 21.5. Anal. Calcd for C$_{26}$H$_{32}$N$_4$O$_5$S: C, 60.92; H, 6.29; N, 10.93. Found: C, 60.45; H, 5.97; N, 10.51.

1-Isopropyl-3-(3-methoxyphenyl)-N-(4-methyl-3-(morpholinosulfonyl)phenyl)-1H-pyrazole-4-carboxamide (4n). To a solution of 7-9 (0.25 g, 0.96 mmol) in CH$_2$Cl$_2$ (5 mL) was added EDCI (0.22 g, 1.15 mmol) and DMAP (1.15 g, 1.15 mmol). To the reaction was added 4-methyl-3-(morpholinosulfonyl)aniline (0.25 g, 0.96 mmol) in one portion and the reaction mixture was stirred at room temperature for 12 h and then treated with 10% HCl. The organic layer was collected and the aqueous layer was extracted with EtOAc. The combined organic solution was dried over Na$_2$SO$_4$, evaporated under a vacuum. The resulting yellow oil was purified by flash column chromatography (H/EtOAc 1:1) to afford 4n as a white solid (0.26 g, 55% yield), mp 158.0° C. $^1$H NMR (CDCl$_3$) δ 8.15 (s, 1H), 7.72 (s, 1H), 7.53 (s, 1H), 7.47 (d, 2H), 7.24 (d, 2H), 7.19 (s, 1H), 7.05 (m, 1H), 4.57 (m, 1H), 3.86 (s, 3H), 3.74 (t, 4H), 3.17 (t, 4H), 2.57 (s, 3H), 1.61 (s, 6H). $^{13}$C NMR (CDCl$_3$) δ 163.2, 161.7, 150.6, 142.2, 137.7, 136.9, 134.8, 134.5, 132.9, 132.6, 131.7, 125.6, 123.6, 123.1, 122.0, 117.6, 67.7, 56.8, 56.0, 46.9, 24.2, 21.7. Anal. Calcd for C$_{25}$H$_{30}$N$_4$O$_5$S.¼ H$_2$O: C, 59.53; H, 5.92; N, 11.10. Found: C, 59.76; H, 5.67; N, 11.10.

1-(3-Methoxybenzyl)-3-(3-methoxyphenyl)-N-(4-methyl-3-(morpholinosulfonyl)phenyl)-1H-pyrazole-4-carboxamide (4o). To a solution of 7-10 (0.25 g, 0.73 mmol) in CH$_2$Cl$_2$ (5 mL) was added EDCI (0.17 g, 0.88 mmol) and DMAP (0.11 g, 0.88 mmol). To the reaction was added 4-methyl-3-(morpholinosulfonyl)aniline (0.19 g, 0.73 mmol) in one portion and the reaction mixture was stirred at room temperature for 12 h and then treated with 10% HCl. The organic layer was collected and the aqueous layer was extracted with EtOAc. The combined organic solution was dried over Na$_2$SO$_4$, evaporated under a vacuum. The resulting yellow oil was solidified by MeOH to afford 4o as a white solid (0.31 g, 74% yield), mp 190.1° C. $^1$H NMR (CDCl$_3$) δ 8.04 (s, 1H), 7.72 (s, 1H), 7.54 (s, 1H), 7.48 (t, 2H), 7.34 (s, 1H), 7.28 (m, 3H), 7.20 (d, 1H), 6.94 (t, 1H), 6.88 (s, 1H), 3.82 (s, 3H), 3.80 (s, 3H), 3.74 (t, 4H), 3.17 (t, 4H), 2.57 (s, 3H). $^{13}$C NMR (CDCl$_3$) δ 163.2, 161.6, 160.0, 151.4, 137.7, 137.4, 135.7, 134.9, 134.5, 131.7, 131.6, 125.0, 123.1, 122.1, 122.0, 116.9, 116.2, 115.5, 115.4, 67.8, 58.1, 56.9, 56.7, 46.9, 21.7. Anal. Calcd for C$_{30}$H$_{32}$N$_4$O$_5$S.½ H$_2$O: C, 61.51; H, 5.50; N, 9.56. Found: C, 61.50; H, 5.28; N, 9.39.

1-Isopropyl-N-(4-methyl-3-(morpholinosulfonyl)phenyl)-3-(4-(trifluoromethyl)phenyl)-1H-pyrazole-4-carboxamide (4p). To a solution of 7-11 (0.2 g, 0.67 mmol) in $CH_2Cl_2$ (5 mL) was added EDCI (0.15 g, 0.81 mmol) and DMAP (0.08 g, 0.81 mmol). To the reaction was added 4-methyl-3-(morpholinosulfonyl)aniline (0.17 g, 0.67 mmol) and the reaction mixture was stirred at room temperature for 12 h and quenched with water and then treated with 10% HCl. The organic layer was collected and the aqueous layer was extracted with EtOAc. The combined organic solution was dried over $Na_2SO_4$, evaporated under a vacuum. The resulting yellow oil was purified by flash column chromatography (H/EtOAc 1:1) to afford 4p as a yellow solid (0.18 g, 51% yield), mp 192.2° C. $^1$H NMR ($CDCl_3$) δ 8.12 (s, 1H), 8.09 (s, 1H), 7.87 (d, 2H), 7.81 (d, 2H), 7.65 (d, 2H), 7.24 (d, 1H), 4.53 (m, 1H), 3.64 (t, 4H), 3.07 (t, 4H), 2.54 (s, 3H), 1.53 (s, 6H). $^{13}$C NMR ($CDCl_3$) δ 161.5, 148.8, 138.6, 136.2, 134.9, 133.7, 133.3, 130.4, 129.3, 125.7, 119.4, 66.2, 66.1, 45.3, 45.2, 22.5, 20.1, 20.0. Anal. Calcd for $C_{25}H_{27}F_3N_4O_4S \cdot \frac{1}{2} H_2O$: C, 55.03; H, 4.98; N, 10.44. Found: C, 55.23; H, 5.03; N, 10.26.

1-(3-Methoxybenzyl)-N-(4-methyl-3-(morpholinosulfonyl)phenyl)-3-(4-(trifluoromethyl)phenyl)-1H-pyrazole-4-carboxamide (4q). To a solution of 7-12 (0.06 g, 0.16 mmol) in $CH_2Cl_2$ (2 mL) was added EDCI (0.04 g, 0.019 mmol) and DMAP (0.02 g, 0.019 mmol). To the reaction was added 4-methyl-3-(morpholinosulfonyl)aniline (0.04 g, 0.16 mmol) and the reaction mixture was stirred at room temperature for 12 h and quenched with water and then treated with 10% HCl. The organic layer was collected and an aqueous layer was extracted with EtOAc. The combined organic solution was dried over $Na_2SO_4$, evaporated under a vacuum. The resulting yellow oil was purified by flash column chromatography (H/EtOAc 1:1) to afford 4q as a yellow solid (0.022 g, 61% yield), mp 208.2° C. $^1$H NMR ($CDCl_3$) δ 7.98 (s, 1H), 7.89 (d, 2H), 7.81 (s, 1H), 7.74 (d, 2H), 7.62 (d, 1H), 7.47 (s, 1H), 7.27 (t, 1H), 7.26 (t, 1H), 6.94 9m, 3H), 5.34 (s, 2H), 3.82 (s, 3H), 3.72 (t, 4H), 3.15 (t, 4H), 2.58 (s, 3H). $^{13}$C NMR ($CDCl_3$) δ 161.5, 148.8, 138.6, 136.2, 134.9, 133.7, 133.3, 130.4, 129.3, 125.7, 119.4, 66.2, 66.1, 45.3, 45.2, 22.5, 20.1, 20.0. Anal. Calcd for $C_{30}H_{29}F3N_4O_5S \cdot \frac{1}{2} H_2O$: C, 57.77; H, 4.68; N, 8.98. Found: C, 58.08; H, 4.64; N, 8.64.

1-Isopropyl-N-methyl-N-(4-methyl-3-(morpholinosulfonyl)phenyl)-3-(p-tolyl)-1H-pyrazole-4-carboxamide (8-1). A mixture of 4f (0.1 g, 0.21 mmol), NaH (60% dispersion in oil) (0.018 g, 0.46 mmol) and anhydrous DMF (10 ml) was stirred at room temperature for 30 min. The reaction mixture was cooled to 0° C., and iodomethane (0.1 mL, 1.47 mmol) was added to it. The resulting mixture was stirred at room temperature under an atmosphere of $N_2$ and monitored by TLC. The reaction was stopped, water (30 ml) was added into the reaction mixture and the aqueous layer was extracted with ethyl acetate (3×15 ml). The combined organic layers were washed with water and brine (3×10 ml), dried over $Na_2SO_4$, filtered and concentrated. The resulting yellow oil was purified by flash column chromatography (H/EtOAc 1:1) to afford 8-1 as a clear oil (0.07 g, 70% yield). $^1$H NMR ($CDCl_3$) δ 7.34 (s, 1H), 7.15 (d, 2H), 7.09 (t, 2H), 6.94 (d, 2H), 6.87 (d, 1H), 4.26 (m, 1H), 3.67 (t, 4H), 3.27 (s, 3H), 3.05 (t, 4H), 2.55 (s, 3H), 2.41 (s, 3H), 1.31 (d, 6H). $^{13}$C NMR ($CDCl_3$) δ 166.5, 144.0, 140.8, 136.8, 134.4, 131.6, 130.8, 130.7, 130.4, 129.6, 129.3, 128.5, 127.4, 67.6, 51.5, 46.6, 39.0, 22.8, 22.7, 21.6. HRMS (ESI); Calcd for $C_{26}H_{32}N_4O_4S$ (M+1): 497.2217. Found: 497.2215.

3-Isopropyl-1-(3-methoxybenzyl)-N-methyl-N-(4-methyl-3-(morpholinosulfonyl)phenyl)-1H-pyrazole-4-carboxamide (8-2). A mixture of 4m (0.3 g, 0.58 mmol), NaH (60% dispersion in oil) (0.046 g, 1.27 mmol) and anhydrous DMF (15 ml) was stirred at room temperature for 30 min. The reaction mixture was cooled to 0° C., and iodomethane (0.25 mL, 4.09 mmol) was added to it. The resulting mixture was stirred at room temperature under an atmosphere of $N_2$ and monitored by TLC. The reaction was stopped, water (50 ml) was added into the reaction mixture and the aqueous layer was extracted with ethyl acetate (3×25 ml). The combined organic layers were washed with water and brine (3×10 ml), dried over $Na_2SO_4$, filtered and concentrated. The resulting yellow oil was purified by flash column chromatography (H/EtOAc 1:1) to afford 8-2 as a clear oil (0.27 g, 87% yield). $^1$H NMR ($CDCl_3$) δ 7.45 (s, 1H), 7.18 (dd, 3H), 6.78 (d, 1H), 6.52 (d, 2H), 6.50 (d, 1H), 4.95 (s, 2H), 3.71 (s, 3H), 3.63 (t, 4H), 3.34 (s, 3H), 3.31 (m, 1H), 2.82 (t, 4H), 2.53 (s, 3H), 1.23 (d, 6H). $^{13}$C NMR ($CDCl_3$) δ 166.5, 144.0, 140.8, 136.8, 134.4, 131.6, 130.8, 130.7, 130.4, 129.6, 129.3, 128.5, 127.4, 67.6, 51.5, 46.6, 39.0, 22.8, 22.7, 21.6. HRMS (ESI); Calcd for $C_{27}H_{34}N_4O_5S$ (M+1): 527.2323. Found: 527.2321.

1-(3-Methoxybenzyl)-3-(3-methoxyphenyl)-N-methyl-N-(4-methyl-3-(morpholinosulfonyl)phenyl)-1H-pyrazole-4-carboxamide (8-3). A mixture of 4o (0.1 g, 0.17 mmol), NaH (60% dispersion in oil) (0.02 g, 0.51 mmol) and anhydrous DMF (10 ml) was stirred at room temperature for 30 min. The reaction mixture was cooled to 0° C., and iodomethane (0.075 mL, 1.21 mmol) was added to it. The resulting mixture was stirred at room temperature under an atmosphere of $N_2$ and monitored by TLC. The reaction was stopped, water (50 ml) was added into the reaction mixture and the aqueous layer was extracted with ethyl acetate (3×25 ml). The combined organic layers were washed with water and brine (3×10 ml), dried over $Na_2SO_4$, filtered and concentrated. The resulting yellow oil was purified by flash column chromatography (H/EtOAc 1:1) to afford 8-2 as a clear oil (0.08 g, 87% yield). $^1$H NMR ($CDCl_3$) δ 7.45 (s, 1H), 7.21 (t, 2H), 7.14 (t, 1H), 6.85 (d, 2H), 6.80 (t, 3H), 6.72 (d, 2H), 6.70 (s, 1H), 5.12 (s, 2H), 3.72 (s, 6H), 3.58 (t, 4H), 3.26 (s, 3H), 2.84 (t, 4H), 2.41 (s, 3H). $^{13}$C NMR ($CDCl_3$) δ 164.3, 159.0, 158.6, 148.3, 140.8, 135.5, 134.4, 133.9, 132.6, 131.6, 131.3, 129.0, 128.3, 127.0, 119.3, 118.8, 113.3, 112.8, 111.3, 65.2, 54.3, 54.2, 44.0, 19.0. HRMS (ESI); Calcd for $C_{31}H_{34}N_4O_6S$ (M+1): 591.2272. Found: 591.2270.

N-((1-Isopropyl-3-(p-tolyl)-1H-pyrazol-4-yl)methyl)-4-methyl-3-(morpholinosulfonyl)aniline (9-1). To a solution of 4f (0.1 g, 0.21 mmol) in anhydrous THF (5 mL), 1 N borane-THF complex (7 mL) was added at 0° C. under $N_2$. The reaction mixture was heated to reflux for 3 h. After it was cooled to 0° C., 1N methanolic HCl (3 ml) was very carefully added dropwise to quench excess borane reagent and addition MeOH was added. The reaction mixture was heated to reflux for 2 h. The solvent was evaporated at reduced pressure. The oily residue was dissolved in EtOAc and neutralized with 2N NaOH. The resulting mixture was extracted with EtOAc (3×15 ml). The combined extracts were washed with 0.5 N KOH, dried over $Na_2SO_4$, and evaporated in vacuo. The resulting yellow oil was purified by flash column chromatography (H/EtOAc 1:1) to afford 9-1 as colorless oil (0.08 g, 81% yield). $^1$H NMR ($CDCl_3$) δ 7.55 (d, 2H), 7.47 (s, 1H), 7.20 (d, 2H), 7.14 (s, 1H), 7.10 (d, 1H), 6.72 (d, 1H), 4.52 (m, 1H), 4.27 (s, 2H), 3.71 (t, 4H), 3.12 (t, 4H), 2.51 (s, 3H), 2.36 (s, 3H), 1.53 (d, 6H), $^{13}$C NMR ($CDCl_3$) δ 150.5, 147.6, 138.8, 136.7, 135.1, 130.7, 128.8, 128.5, 127.6, 118.7, 115.7, 69.0, 46.7, 33.1, 24.1, 24.0. HRMS (ESI); Calcd for $C_{25}H_{32}N_4O_3S$ (M+1): 469.6116. Found: 469.2715.

N-((3-Isopropyl-1-(3-methoxybenzyl)-1H-pyrazol-4-yl)methyl)-4-methyl-3-(morpholinosulfonyl)aniline (9-2). To a solution of 4m (0.1 g, 0.19 mmol) in anhydrous THF (5 mL), 1 N borane-THF complex (7 mL) was added at 0° C. under $N_2$. The reaction mixture was heated to reflux for 3 h. After it was cooled to 0° C., 1N methanolic HCl (3 ml) was very carefully added dropwise to quench excess borane reagent and additional MeOH was added. The reaction mixture was heated to reflux for 3 h. The solvent was evaporated at reduced pressure. The oily residue was dissolved in EtOAc and neutralized with 2N NaOH. The resulting mixture was extracted with EtOAc (3×15 ml). The combined extracts were washed with 0.5 N KOH, dried over $Na_2SO_4$, and evaporated in vacuo. The resulting yellow oil was purified by flash column chromatography (H/EtOAc 1:1) to afford 9-2 as colorless oil (0.07 g, 77% yield). $^1$H NMR (CDCl$_3$) δ 7.22 (d, 2H), 7.21 (s, 1H), 7.12 (s, 1H), 7.10 (d, 1H), 6.83 (d, 1H), 6.77 (d, 1H), 6.72 (t, 2H), 5.18 (s, 2H), 4.11 (t, 2H), 3.76 (s, 3H), 3.69 (t, 4H), 3.11 (t, 4H), 3.05 (m, 1H), 2.48 (s, 3H), 1.26 (d, 6H). $^{13}$C NMR (CDCl$_3$) δ 161.3, 157.7, 147.6, 139.6, 136.4, 135.1, 131.2, 130.5, 127.1, 121.3, 118.5, 116.6, 115.6, 114.8, 114.7, 67.7, 57.1, 56.6, 46.7, 39.8, 26.5, 24.0, 23.6, 21.1. HRMS (ESI); Calcd for $C_{26}H_{34}N_4O_4S$ (M+1): 499.6376. Found: 499.3676.

N-((1-(3-Methoxybenzyl)-3-(3-methoxyphenyl)-1H-pyrazol-4-yl)methyl)-4-methyl-3-(morpholinosulfonyl)aniline (9-3). To a solution of 4o (0.1 g, 0.17 mmol) in anhydrous THF (5 mL), 1 N borane-THF complex (8 mL) was added at 0° C. under $N_2$. The reaction mixture was heated to reflux for 3 h. After it was cooled to 0° C., 1N methanolic HCl (3 ml) was very carefully added dropwise to quench excess borane reagent and additional MeOH was added. The reaction mixture was heated to reflux for 2 h. The solvent was evaporated at reduced pressure. The oily residue was dissolved in EtOAc and neutralized with 2N NaOH. The resulting mixture was extracted with EtOAc (3×15 ml). The combined extracts were washed with 0.5 N KOH, dried over $Na_2SO_4$, and evaporated in vacuo. The resulting yellow oil was purified by flash column chromatography (H/EtOAc 1:1) to afford 9-3 as colorless oil (0.065 g, 72% yield). $^1$H NMR (CDCl$_3$) δ 7.38 (s, 1H), 7.32 (m, 5H), 7.18 (d, 1H), 7.11 (s, 1H), 6.89 (t, 2H), 6.81 (d, 2H), 6.69 (t, 1H), 5.28 (s, 2H), 4.26 (s, 2H), 3.81 (s, 3H), 3.76 (s, 3H), 3.71 (t, 4H), 3.11 (t, 4H), 2.49 (s, 3H). $^{13}$C NMR (CDCl$_3$) δ 161.3, 161.2, 151.1, 147.3, 139.1, 136.4, 135.1, 131.7, 131.3, 127.4, 121.5, 118.6, 117.7, 115.7, 115.3, 115.1, 116.2, 114.8, 114.1, 67.7, 57.5, 56.6, 46.7, 40.5, 21.2. HRMS (ESI); Calcd for $C_{30}H_{34}N_4O_5S$ (M+Na): 565.6798. Found: 585.2798.

Example 10

Biology

DMSO and charcoal/dextran-treated FBS were obtained from Fisher Scientific (Pittsburgh, Pa.). GW4064 was purchased from R&D Systems, Inc. (Minneapolis, Minn.); lithocholic acid and rifampicin were purchased from Sigma-Aldrich (St. Louis, Mo.); TO901317 was obtained from Cayman Chemical Company (Ann Arbor, Mich.); Z26476908 was purchased from Enamine LLC (Monmouth Junction, N.J.). Black polypropylene 384-well plates were purchased from Matrical Bioscience (Spokane, Wash.). Black 384-well tissue culture-treated clear bottom plates were obtained from Corning Incorporated (Corning, N.Y.). White tissue culture-treated 384-well plates were purchased from PerkinElmer (Waltham, Mass.). GST-hFXR-LBD, Tb-anti-GST antibody, coregulator buffer G, 1 M DTT, GeneBLAzer FXR-UAS-bla HEK 293T cells, DMEM, phenol red-free DMEM, dialyzed FBS, non-essential amino acids, sodium pyruvate, HEPES, hygromycin B, zeocin, penicillin/streptomycin, G418 and CCF4-AM substrate were purchased from Invitrogen (Carlsbad, Calif.).

All chemicals were initially solubilized in DMSO as 10 mM stocks and then diluted in corresponding assay buffer or medium to indicated concentrations. All experiments were repeated in triplicate and representative results were reported.

FXR TR-FRET Binding Assay

The FXR TR-FRET binding assay was performed as previously described[23] with modifications. Briefly, in a black polypropylene 384-well plate (Matrical Bioscience, Spokane, Wash.), DMSO, 10 μM GW4064, and titrations of GW4064, lithocholic acid or the synthesized chemicals were mixed with 10 nM GST-hFXR-LBD, 1.5 nM Tb-anti-GST antibody (Invitrogen, Carlsbad, Calif.), and 10 nM DY246 in a 20 μl/well of coregulator buffer G supplemented with 10 mM DTT. The final DMSO concentration was 0.4% for all wells. The plate was spun down after a brief shake and incubated at room temperature for 20 min. The TR-FRET emission signals at 520 nm and 490 nm for each well was then collected using a PHERAstar plate reader (BMG LABTECH, Cary, N.C.) with an excitation wavelength of 337 nm, 100-μs delay time, and 200-μs integration time. The 520 nm/490 nm ratio from each well was then calculated. The DMSO group and 10 μM GW4064 group were served as negative (0% inhibition) and positive (100% inhibition) controls, respectively. The % inhibition of tested chemicals at given concentration was calculated based on negative and positive controls using equation 1.

$$\%\text{Inhibition} = 100\% - 100\% \times \frac{\text{Chemical}_{520\,nm/490\,nm} - 10\,\mu M\ GW\ 4064_{520\,nm/490\,nm}}{DMSO_{520\,nm/490\,nm} - 10\,\mu M\ GW\ 4064_{520\,nm/490\,nm}} \quad \text{Equation 1}$$

For those chemicals with a maximal % inhibition >50% and activities that behaved in a dose-dependent manner, their inhibitory activities at different concentrations were fit into a one-site competitive binding equation with GraphPad PRISM 6.01 (GraphPad Software, Inc., La Jolla, Calif.) to derive $IC_{50}$ values.

FXR Cell-Based Transactivation Assay

FXR transactivation assays were performed using GeneBLAzer FXR-UAS-bla HEK 293T cells (Invitrogen). Cells were maintained according to the manufacturer's instructions. Briefly, cells were grown in DMEM supplemented with 10% dialyzed FBS, 0.1 mM non-essential amino acids, 25 mM HEPES, 100 μg/ml of hygromycin B, 100 μg/ml of zeocin, 100 units/ml penicillin and 100 μg/ml streptomycin in regular tissue culture flasks. Upon transactivation assay, DMSO, 400 nM GW4064, 10 μM GW4064, and titrations of GW4064, LCA or chemicals without 400 nM GW4064 (for FXR agonistic activity determination) or with 400 nM GW4064 (for FXR antagonistic activity determination) were mixed with cells (20,000 cells/well in a 30 μL) in assay medium (phenol red-free DMEM supplemented with 2% charcoal/dextran-treated FBS, 0.1 mM non-essential amino acids, 1 mM sodium pyruvate, 100 units/ml penicillin and 100 μg/ml streptomycin) in black 384-well tissue culture-treated clear bottom plates (Corning Incorporated, Corning, N.Y.). As a background control, the wells in column 24 of each plate were filled with 30 µL assay medium along with 0.5% DMSO. The final DMSO concentration was 0.5% in each assay well. After a 16 h incubation in a cell culture incubator at 37° C., 6 µl/well of loading solution with CCF4-AM substrate was added. Plates were then incubated in dark for 90 min at room temperature before measuring the fluorescent emissions at 460 nm and 535 nm (using excitation at 400 nm) with an Envision plate reader with bottom read capacity. After background signal subtraction for individual emission channels, emission signals at 460 and 535 nm from each well were used to determine the ratio of 460 nm/535 nm. For agonist assays, the DMSO group and 10 µM GW4064 group served as negative (0% activation) and positive (100% activation) controls, respectively. The % activation was calculated using equation 2.

$$\%\text{Activation} = 100\% \times \frac{\text{Chemical}_{460\ nm/535\ nm} - \text{DMSO}_{460\ nm/535\ nm}}{10\ \mu M\ GW\ 4064_{460\ nm/535\ nm} - \text{DMSO}_{460\ nm/535\ nm}} \quad \text{Equation 2}$$

For antagonistic assay in which 400 nM GW4064 was included in the assay conditions, the DMSO group and 400 nM GW4064 group served as positive (100% inhibition) and negative (0% inhibition) controls, respectively. The % inhibition was calculated using equation 3.

$$\%\text{Inhibition} = 100\% - 100\% \times \frac{(\text{Chemical} + 400\ nM\ GW\ 4064)_{460\ nm/535\ nm} - \text{DMSO}_{460\ nm/535\ nm}}{400\ nM\ GW\ 4064_{460\ nm/535\ nm} - \text{DMSO}_{460\ nm/535\ nm}} \quad \text{Equation 3}$$

For those chemicals with a maximal % inhibition >50% and activities that behaved in a dose-dependent manner, their inhibitory activities at different concentrations were fit into a sigmoidal dose-response equation with GraphPad PRISM 6.01 (GraphPad Software, Inc., La Jolla, Calif.) to derive $IC_{50}$ values.

Cell-Based Cytotoxicity Assay

Cytotoxicity assays were performed side-by-side with the FXR agonistic assay using GeneBLAzer FXR-UAS-bla HEK 293T cells with CellTiter-Glo® Luminescent Cell Viability Assay reagent (Promega). Briefly, cells were maintained in DMEM supplemented with 10% dialyzed FBS, 0.1 mM non-essential amino acids, 25 mM HEPES, 100 µg/ml of hygromycin B, 100 µg/ml of zeocin, 100 units/ml penicillin and 100 µg/ml streptomycin in regular tissue culture flasks. For the cytotoxicity assay, DMSO, titrations of GW4064, LCA or of chemicals were mixed with cells (20,000 cells/well in a 30 µL) in assay medium (phenol red-free DMEM supplemented with 2% charcoal/dextran-treated FBS, 0.1 mM non-essential amino acids, 1 mM sodium pyruvate, 100 units/ml penicillin and 100 µg/ml streptomycin) in black 384-well tissue culture-treated clear bottom plates (Corning Incorporated, Corning, N.Y.). As a positive control, the wells in column 24 of each plate were filled with 30 µL assay medium along with 0.5% DMSO. The final DMSO concentration was 0.5% in each assay well. After a 16 h incubation in a cell culture incubator at 37° C., the cell plates were cooled at room temperature for 20 min and then CellTiter-Glo® reagent 20 µl/well was added followed by an incubation for 20 min in the dark to allow the development of optimal luminescence signal. The luminescence signal from each well in plates was collected with an Envision plate reader equipped with Ultra-sensitive Luminescence detector. The DMSO group and no cell group served as negative (0% activation) and positive (100% activation) controls, respectively. The % inhibition was calculated using equation 4 below.

$$\%\text{Inhibition} = 100\% - 100\% \times \frac{\text{Signal}_{compound} - \text{Signal}_{No\ Cell}}{\text{Signal}_{DMSO} - \text{Signal}_{No\ Cell}} \quad \text{Equation 4}$$

Abbreviations Used

HTS, High-Throughput Screen; FXR, farnesoid X receptor; NRs, nuclear receptors; Cyp7A1, cytochrome 7A1; BAs, bile acids; CDCA, chenodeoxycholic acid; BSEP, bile salt export pump; SHP, small heterodimer partner; SAR, structure-activity relationship: LBD, ligand-binding domain.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

1. Nuclear Receptor Nomenclature Committee. A unified nomenclature system for the nuclear receptor superfamily. *Cell* 1999, 97, 161-163.
2. Forman, B. M.; Goode, E.; Chen, J.; Oro, A. E.; Bradley, D. J.; Perlmann, T.; Noonan, D. J.; Burka, L. T.; McMorris, T.; Lamph, W. W.; Evans, R. M.; Weinberger, C. Identification of a nuclear receptor that is activated by farnesol metabolites. *Cell* 1995, 81, 687-693.
3. Wang, H.; Chen, J.; Hollister, K.; Sower, L. C.; Forman, B. M. Endogenous bile acids are ligands for the nuclear receptor FXR/BAR. *Mol. Cell* 1999, 3, 543-553.
4. Fiorucci, S.; Mencarelli, A.; Distrutti, E.; Palladino, G.; Cipriani, S. Targeting farnresoid-X-receptor: from medicinal chemistry to disease treatment. *Curr. Med. Chem.* 2010, 17, 139-159.
5. Fiorucci, S.; Cipriani, S.; Baldelli, F.; Mencarelli, A. Bile acidactivated receptors in the treatment of dyslipidemia and related disorders. Prog. Lipid Res. 2010, 49, 171-185.
6. Chen, W. D; Wang, Y. D; Zhang, L; Shiah, S; Wang, M; Yang, F; Yu, D; Forman, B. M; Huang, W. (2010). Farnesoid X receptor alleviates age-related proliferation defects in regenerating mouse livers by activating forkhead box mlb transcription. *Hepatology.* 51(3):953-962.
7. Fiorucci., S.; Baldelli, F. Farnesoid X receptor agonists in biliary tract disease. Curr. Opin. Gastroenterol. 2009, 25, 252-259.
8. Donna Yu, Daniell L. Mattem, and Barry M. Forman. An improved synthesis of 6α-ethyl chenodeoxycholic acid (6ECDCA), a potent and selective agonist for the farnesoid X receptor (FXR). *Steroids,* 2012, 77, 1335-1338.

9. Modica, S.; Moschetta, A. Nuclear bile acid receptor FXR as pharmacological target: are we there yet? *FEBS Lett.* 2006, 580, 5492-5499.

10. Renga, B.; Migliorati, M.; Mencarelli, A.; Cipriani, S.; D'Amore, C.; Distrutti, E.; Fiorucci, S. Farnesoid X receptor suppresses constitutive androstane receptor activity at the multidrug resistance protein-4 promoter. *Biochim. Biophys. Acta* 2011, 1809, 157-165.

11. Fiorucci, S.; Zampella, A. Distrutti E. Development of FXR, PXR and CAR agonists and antagonists for treatment of liver disorders. *Curr Top Med Chem.* 2012, 12, 605-24.

12. Makishima, M.; Okamoto, A. Y.; Repa, J. J.; Tu, H.; Learned, R. M.; Luk, A.; Hull, M. V.; Lustig, K. D.; Mangelsdorf, D. J.; Shan, B. Identification of a nuclear receptor for bile acids. *Science* 1999, 284, 1362-1365.

13. Urizar, N. L.; Liverman, A. B.; Dodds, D. T.; Silva, F. V.; Ordentlich, P.; Yan, Y. Z.; Gonzalez, F. J.; Heyman, R. A.; Mangelsdorf, D. J.; Moore, D. D. A natural product that lowers cholesterol as an antagonist ligand for FXR. *Science* 2002, 296, 1703-1706.

14. Urizar, N. L.; Moore, D. D. Guggulipid: a natural cholesterollowering agent. *Annu. Rev. Nutr.* 2003, 23, 303-313.

15. Pellicciari, R.; Costantino, G.; Fiorucci, S. Farnesoid X Receptor: From Structure to Potential Clinical Applications. *J. Med. Chem.* 2005. 17, 1-21.

16. Sepe, V.; Bifulco, G.; Renga, B.; D'Amore, C.; Fiorucci, S.; Zampella, A. Discovery of Sulfated Sterols from Marine Invertebrates as a New Class of Marine Natural Antagonists of Farnesoid-X-Receptor, *J. Med. Chem.*, 2011, 54, 1314-1320.

17. Rengal, B.; Mencarelli, A.; D'Amore, C.; Cipriani, S.; D'Auria, M. V.; Sepe, V.; Chini, M. G.; Monti, M. C.; Bifulco, G.; Zampella, A.; Fiorucci, S. Discovery that theonellasterol a marine sponge sterol is a highly selective FXR antagonist that protects against liver injury in cholestasis. *PLoS ONE.* 2012, 7, e30443.

18. Nam, S. J.; Ko, H.; Shin, M.; Ham, J.; Chin, J.; Kim, Y.; Kim, H.; Shin, K.; Choi, H.; Kang, H. Farnesoid X-activated receptor antagonists from a marine sponge Spongia sp. *Bioorg. Med. Chem. Lett.* 2006, 16, 5398-5402.

19. Di Leva, F. S.; Festa, C.; D'Amore, C.; De Marino, S.; Renga, B.; D'Auria, M. V.; Novellino, E.; Limongelli, V.; Zampella, A.; Fiorucci, S. Binding Mechanism of the Farnesoid X Receptor Marine Antagonist Suvanine Reveals a Strategy To Forestall Drug Modulation on Nuclear Receptors. Design, Synthesis, and Biological Evaluation of Novel Ligands. J. Med. Chem. 2013, 56, 4701-4717.

20. Dussault, I.; Beard, R.; Lin, M.; Hollister, K.; Chen, J.; Xiao, J. H.; Chandraratna, R.; Forman, B. M. Identification of gene selective modulators of the bile acid receptor FXR. *J. Biol. Chem.* 2003, 278, 7027-7033.

21. Huang, H.; Yu, Y.; Gao, Z.; Zhang, Y.; Li, C.; Xu, X.; Jin, H.; Yan, W.; Ma, R.; Zhu, J. Shen, X.; Jiang, H.; Chen, L.; Li, J. Discovery and Optimization of 1,3,4-Trisubstituted-pyrazolone Derivatives as Novel, Potent, and Nonsteroidal Farnesoid X Receptor (FXR) Selective Antagonists. *J. Med. Chem.* 2012, 55, 7037-7053.

22. Sayin, S. I.; Wahlstroem, A.; Felin, J.; Jaentti, S.; Marschall, H-U.; Bamberg, K.; Angelin, B.; Hyoetylaeinen, T.; Oresic, M.; Baeckhed, F. Gut Microbiota Regulates Bile Acid Metabolism by Reducing the Levels of Tauro-beta-muricholic Acid, a Naturally Occurring FXR Antagonist, *Cell Metabolism*, 2013, 17, 225-235.

23. Yu, D. D., Lin, W., Chen, T., Forman, B. M. Development of Time Resolved Fluorescence Resonance Energy Transfer-based Assay for FXR Antagonist Discovery, *Bioorganic & Medicinal Chemistry*, 2013, 21, 4266-4278.

24. Takeda Pharmaceutical Co. Ltd., Heterocyclic amide compound and use thereof, WO/2007/052843, 2007.

25. Lamberth, C. Pyrazole chemistry in crop protection. *Heterocycles,* 2007, 71, 1467.

26. Akwabi-Ameyaw, A.; Caravella, J. A.; Chen, L.; Creech, K. L.; Deaton, D. N.; Madauss, K. P.; Marr, H. B.; Miller, A. B.; Navas, F., III; Parks, D. J.; Spearing, P. K.; Todd, D.; Williams, S. P.; Wisely, G. B. Conformationally constrained farnesoid X receptor (FXR) agonists: alternative replacements of the stilbene. *Bioorg. Med. Chem. Lett.* 2011, 21, 6154-6160.

27. Hashimoto, Y. Retinobenzoic acids and nuclear retinoic acid receptors. *Cell Struct. Funct.* 1991, 16, 113-123.

28. Soisson, S. M; Parthasarathy, G.; Adams, A. D.; Sahoo, S.; Sitlani, A.; Sparrow, C; Cui, J; Becker, J. W. Identification of a potent synthetic FXR agonist with an unexpected mode of binding and activation. *Proc Natl Acad Sci USA.* 2008, 105, 5337-5342.

29. Babaoglu, K.; Shoichet, B. K. Deconstructing fragment-based inhibitor discovery. *Nat. Chem. Biol.* 2006, 2, 720-723.

30. Bebemitz, G. R.; Argentieri, G.; Battle, B.; Brennan, C.; Balkan, B.; Burkey, B. F.; Eckhardt, M.; Gao, J.; Kapa, P.; Strohschein, R. J.; Schuster, H. F.; Wilson, M.; Xu, D. D. The Effect of 1,3-Diaryl-[1H]-pyrazole-4-acetamides on Glucose Utilization in ob/ob Mice. *J Med. Chem.* 2001, 44, 2601-2611.

31. Baraldi, P. G.; Tabrizi, M. A.; Preti, D. Bovero, A.; Fruttarolo, F.; Romagnoli, R.; Zaid, N. A.; Moorman, A. R.; Varani, K.; Borea P. A. New 2-Arylpyrazolo[4,3-c]quinoline Derivatives as Potent and Selective Human $A_3$ Adenosine Receptor Antagonists. *J Med. Chem.* 2005. 48, 5001-5008.

32. Lepore, S. D.; He, Y. Use of sonication for the coupling of sterically hindered substrates in the phenolic Mitsunobu reaction. *J. Org. Chem.* 2003, 68, 8261-8263.

33. Petzinger, E.; Wickboldt, A.; Pagels, P.; Starke, D.; Kramer, W. Hepatobiliary Transport of Bile Acid Amino Acid, Bile Acid Peptide, and Bile Acid Oligonucleotide Conjugates in Rats. *Hepatology* 1999, 30, 1257-1268.

34. Ozers, M. S.; Marks, B. D.; Gowda, K.; Kupcho, K. R.; Ervin, K. M.; De Rosier, T.; Qadir, N.; Eliason, H. C.; Riddle, S. M.; Shekhani, M. S. The Androgen Receptor T877A Mutant Recruits LXXLL and FXXLF Peptides Differently than Wild-Type Androgen Receptor in a Time-Resolved Fluorescence Resonance Energy Transfer Assay, *Biochemistry* 2007, 46, 683-695.

35. Li, G.; Lin, W.; Araya, J. J.; Chen, T.; Timmermann, B. N.; Guo, G. L. A tea catechin, epigallocatechin-3-gallate, is a unique modulator of the farnesoid X receptor. Toxicol Appl Pharmacol. 2012, 258, 268-74.

What is claimed is:

1. A method of antagonizing Farnesoid X Receptor (FXR) protein, said method comprising contacting a FXR protein with the compound having formula (II):

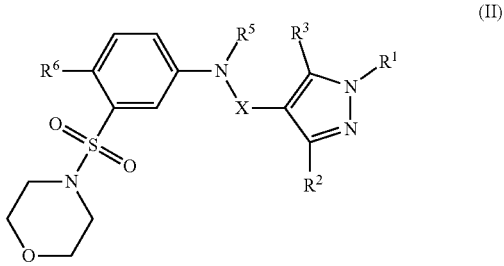

(II)

wherein,

X is —CH$_2$—, —C(O)— or —CY(OH)—;

Y is hydrogen;

R$^1$ is R$^{10}$-substituted or unsubstituted alkyl, R$^{10}$-substituted or unsubstituted cycloalkyl, R$^{10}$-substituted or unsubstituted aryl, or R$^{10}$-substituted or unsubstituted heteroaryl;

R$^{10}$ is hydrogen, halogen, —N$_3$, —CF$_3$, —CCl$_3$, —CBr$_3$, —Cl$_3$, —CN, —CHO, —OR$^{10A}$, —NR$^{10B}$R$^{10C}$, —COOR$^{10A}$, —C(O)NR$^{10B}$R$^{10C}$, —NO$_2$, —S(O)$_{n10}$R$^{10B}$, —S(O)$_{n10}$OR$^{10B}$, —S(O)$_{n10}$NR$^{10B}$R$^{10C}$, —NHNR$^{10B}$R$^{10C}$, —ONR$^{10B}$R$^{10C}$, —NHC(O)NHNR$^{10B}$R$^{10C}$, R$^{13}$-substituted or unsubstituted alkyl, R$^{13}$-substituted or unsubstituted heteroalkyl, R$^{13}$-substituted or unsubstituted cycloalkyl, R$^{13}$-substituted or unsubstituted heterocycloalkyl, R$^{13}$-substituted or unsubstituted aryl, or R$^{13}$-substituted or unsubstituted heteroaryl;

R$^{13}$ is halogen, —N$_3$, —NO$_2$, —CF$_3$, —CCl$_3$, —CBr$_3$, —Cl$_3$, —CN, —OH, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{14}$-substituted or unsubstituted alkyl, R$^{14}$-substituted or unsubstituted heteroalkyl, R$^{14}$-substituted or unsubstituted cycloalkyl, R$^{14}$-substituted or unsubstituted heterocycloalkyl, R$^{14}$-substituted or unsubstituted aryl, or R$^{14}$-substituted or unsubstituted heteroary;

R$^{14}$ is halogen, —N$_3$, —NO$_2$, —CF$_3$, —CCl$_3$, —CBr$_3$, —Cl$_3$, —CN, —OH, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{15}$-substituted or unsubstituted alkyl, R$^{15}$-substituted or unsubstituted heteroalkyl, R$^{15}$-substituted or unsubstituted cycloalkyl, R$^{15}$-substituted or unsubstituted heterocycloalkyl, R$^{15}$-substituted or unsubstituted aryl, or R$^{15}$-substituted or unsubstituted heteroaryl;

R$^{15}$ is halogen, —N$_3$, —NO$_2$, —CF$_3$, —CCl$_3$, —CBr$_3$, —Cl$_3$, —CN, —OH, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{16}$-substituted or unsubstituted alkyl, R$^{16}$-substituted or unsubstituted heteroalkyl, R$^{16}$-substituted or unsubstituted cycloalkyl, R$^{16}$-substituted or unsubstituted heterocycloalkyl, R$^{16}$-substituted or unsubstituted aryl, or R$^{16}$-substituted or unsubstituted heteroaryl;

R$^{16}$ is halogen, —N$_3$, —NO$_2$, —CF$_3$, —CCl$_3$, —CBr$_3$, —Cl$_3$, —CN, —OH, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{14}$-substituted or unsubstituted alkyl, unsubstituted heteroalkyl, unsubstituted cycloalkyl, unsubstituted heterocycloalkyl, unsubstituted aryl, or unsubstituted heteroaryl;

R$^2$ is R$^{17}$-substituted or unsubstituted alkyl, R$^{17}$-substituted or unsubstituted aryl, or R$^{17}$-substituted or unsubstituted heteroaryl;

R$^{17}$ is independently halogen, —N$_3$, —CF$_3$, —CCl$_3$, —CBr$_3$, —Cl$_3$, —CN, —CHO, —OR$^{17A}$, —NR$^{17B}$R$^{17C}$, —COOR$^{17A}$, —C(O)NR$^{17B}$R$^{17C}$, —SR$^{17D}$, —S(O)$_{n17}$R$^{17B}$, —S(O)$_{m17}$OR$^{17B}$, —S(O)$_{n17}$NR$^{17B}$R$^{17C}$, —NHNR$^{17B}$R$^{17C}$, —ONR$^{17B}$R$^{17C}$, —NHC(O)NHNR$^{17B}$R$^{17C}$, R$^{18}$-substituted or unsubstituted alkyl, R$^{18}$-substituted or unsubstituted heteroalkyl, R$^{18}$-substituted or unsubstituted cycloalkyl, R$^{18}$-substituted or unsubstituted heterocycloalkyl, R$^{18}$-substituted or unsubstituted aryl, or R$^{18}$-substituted or unsubstituted heteroaryl;

R$^{18}$ is halogen, —N$_3$, —NO$_2$, —CF$_3$, —CCl$_3$, —CBr$_3$, —Cl$_3$, —CN, —OH, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{19}$-substituted or unsubstituted alkyl, R$^{19}$-substituted or unsubstituted heteroalkyl, R$^{19}$-substituted or unsubstituted cycloalkyl, R$^{19}$-substituted or unsubstituted heterocycloalkyl, R$^{19}$-substituted or unsubstituted aryl, or R$^{19}$-substituted or unsubstituted heteroaryl;

R$^{19}$ is halogen, —N$_3$, —NO$_2$, —CF$_3$, —CCl$_3$, —CBr$_3$, —Cl$_3$, —CN, —OH, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{20}$-substituted or unsubstituted alkyl, R$^{20}$-substituted or unsubstituted heteroalkyl, R$^{20}$-substituted or unsubstituted cycloalkyl, R$^{20}$-substituted or unsubstituted heterocycloalkyl, R$^{20}$-substituted or unsubstituted aryl, or R$^{20}$-substituted or unsubstituted heteroaryl;

R$^{20}$ is halogen, —N$_3$, —NO$_2$, —CF$_3$, —CCl$_3$, —CBr$_3$, —Cl$_3$, —CN, —OH, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl;

R$^3$ is hydrogen or R$^{21}$-substituted or unsubstituted alkyl;

R$^{21}$ is is halogen, —N$_3$, —NO$_2$, —CF$_3$, —CCl$_3$, —CBr$_3$, —Cl$_3$, —CN, —OH, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl;

R$^5$ is hydrogen, or unsubstituted alkyl;

R$^6$ is halogen, or unsubstituted alkyl;

R$^{10A}$, R$^{10B}$, R$^{10C}$, and R$^{10D}$, are independently hydrogen, R$^{13}$-substituted or unsubstituted alkyl, R$^{13}$-substituted or unsubstituted heteroalkyl, R$^{13}$-substituted or unsubstituted cycloalkyl, R$^{13}$-substituted or unsubstituted heterocycloalkyl, R$^{13}$-substituted or unsubstituted aryl, or R$^{13}$-substituted or unsubstituted heteroaryl;

R$^{17A}$, R$^{17B}$, R$^{17C}$, or R$^{17D}$ are independently hydrogen, R$^{18}$-substituted or unsubstituted alkyl, R$^{18}$-substituted or unsubstituted heteroalkyl, R$^{18}$-substituted or unsubstituted cycloalkyl, R$^{18}$-substituted or unsubstituted heterocycloalkyl, R$^{18}$-substituted or unsubstituted aryl, or R$^{18}$-substituted or unsubstituted heteroaryl;

n10 and n17 are independently 1 or 2; and wherein if X is —C(O)— and R$^1$ is unsubstituted phenyl, then R$^2$ is not methyl, p-substituted or unsubstituted phenyl, or unsubstituted pyridine.

2. The method of claim 1, wherein X is —C(O)—.

3. The method of claim 1, wherein $R^1$ is $R^{10}$-substituted or unsubstituted alkyl, $R^{10}$-substituted or unsubstituted aryl or $R^{10}$-substituted or unsubstituted heteroaryl; wherein $R^{10}$ is independently hydrogen, halogen, —$N_3$, —$CF_3$, —$CCl_3$, —$CBr_3$, —$CI_3$, —CN, —CHO, —$OR^{10A}$, substituted or unsubstituted alkyl, substituted or unsubstituted heteroalkyl, substituted or unsubstituted aryl, or substituted or unsubstituted heteroaryl; and $R^{10A}$ is independently hydrogen or unsubstituted alkyl.

4. The method of claim 3, wherein $R^1$ is $R^{10}$-substituted or unsubstituted alkyl, $R^{10}$-substituted or unsubstituted aryl or $R^{10}$-substituted or unsubstituted heteroaryl; wherein $R^{10}$ is independently halogen, —$CF_3$, —$OR^{10A}$, substituted or unsubstituted $C_1$-$C_5$-alkyl or substituted or unsubstituted aryl; and $R^{10A}$ is hydrogen or methyl.

5. The method of claim 1, wherein $R^2$ is hydrogen, $R^{17}$-substituted or unsubstituted alkyl or $R^{17}$-substituted or unsubstituted aryl, wherein $R^{17}$ is independently halogen, —$CF_3$, —$OR^{17A}$, or unsubstituted $C_1$-$C_5$-alkyl; and $R^{17A}$ is hydrogen or unsubstituted $C_1$-$C_5$-alkyl.

6. The method of claim 1, wherein $R^3$ is hydrogen, halogen, —$N_3$, —$CF_3$, —$CCl_3$, —$CBr_3$, —$CI_3$, —CN, —CHO, —$OR^{3A}$, or $R^{21}$-substituted or unsubstituted alkyl, wherein $R^{3A}$ is hydrogen or unsubstituted $C_1$-$C_5$ alkyl; and $R^{21}$ is hydrogen or substituted or unsubstituted $C_1$-$C_5$ alkyl.

7. The method of claim 6, wherein $R^3$ is hydrogen, halogen, —$CF_3$, —OH, or substituted or unsubstituted alkyl.

8. The method of claim 1, wherein $R^5$ is hydrogen or methyl.

9. The method of claim 1, wherein $R^6$ is unsubstituted $C_1$-$C_5$ alkyl.

10. The method of claim 1, wherein the compound is:

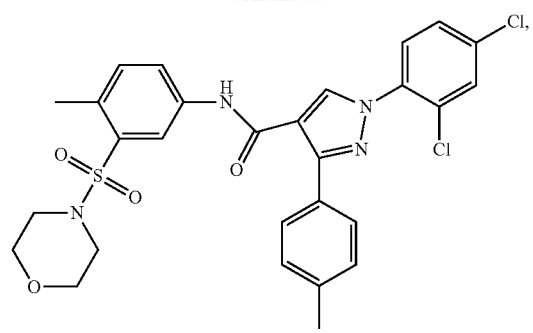

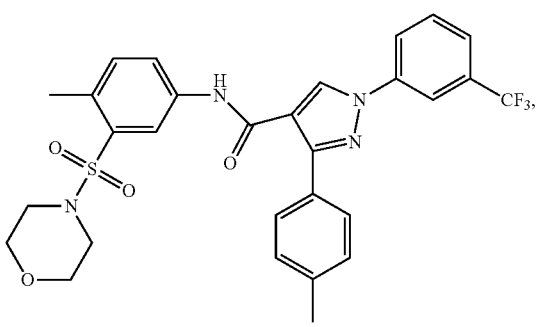

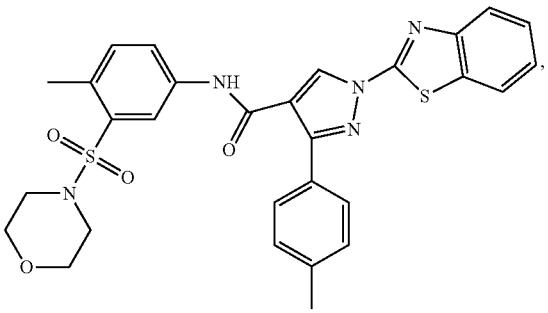

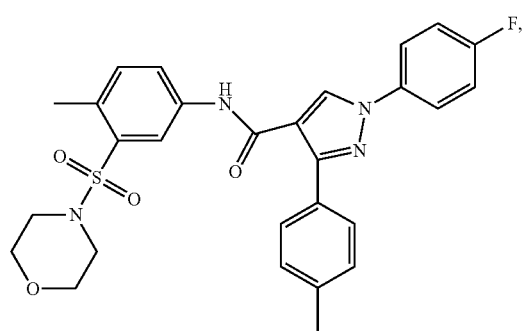

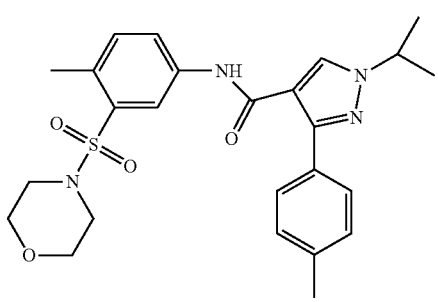

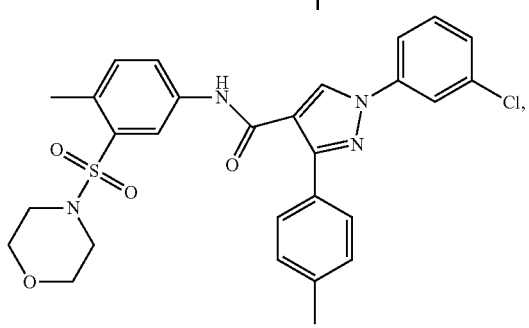

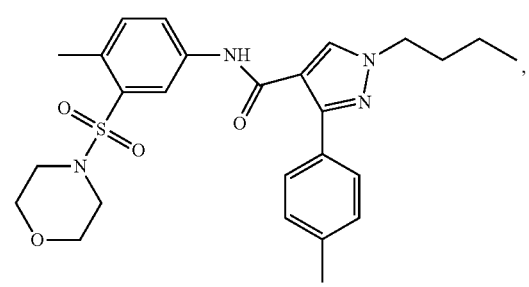

117
-continued
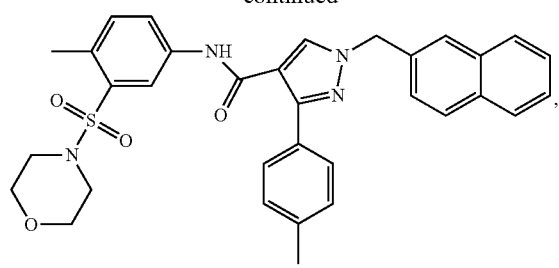
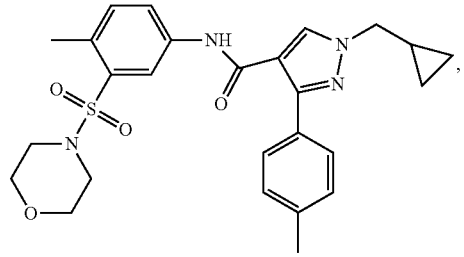
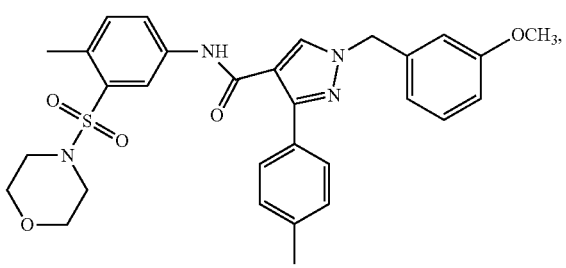
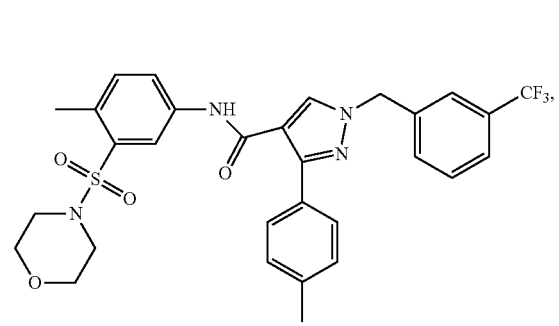
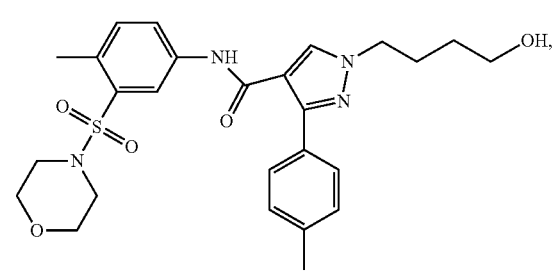
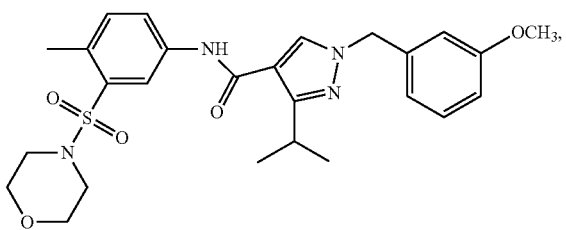
118
-continued
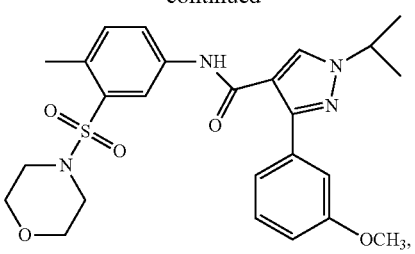
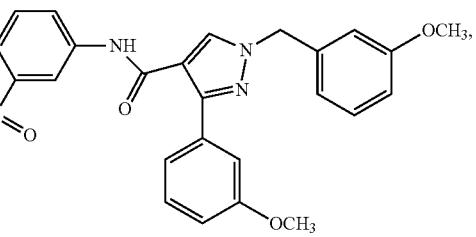
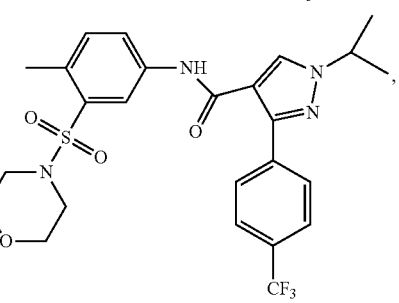
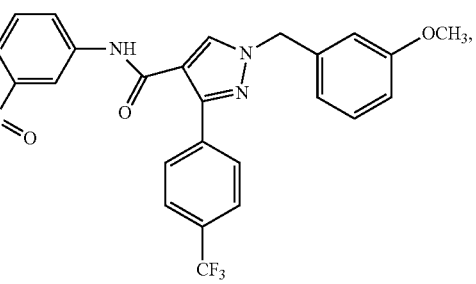
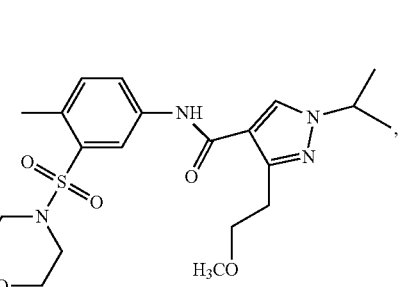
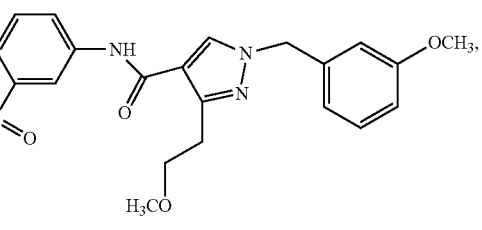

119
-continued
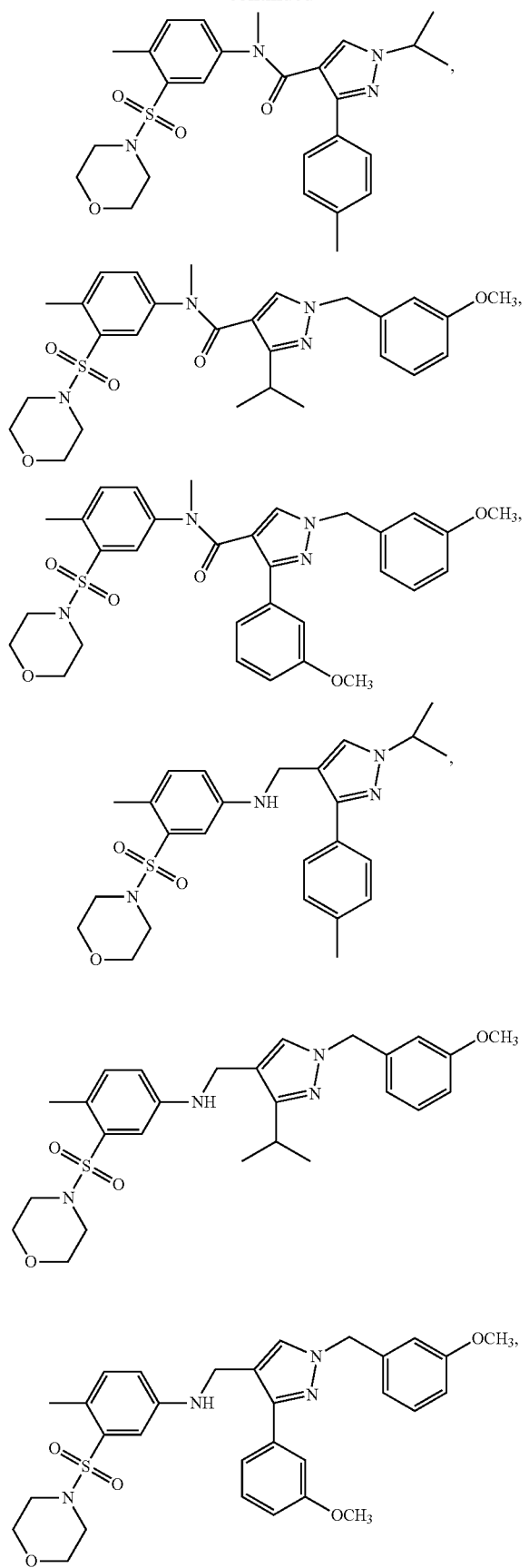
120
-continued
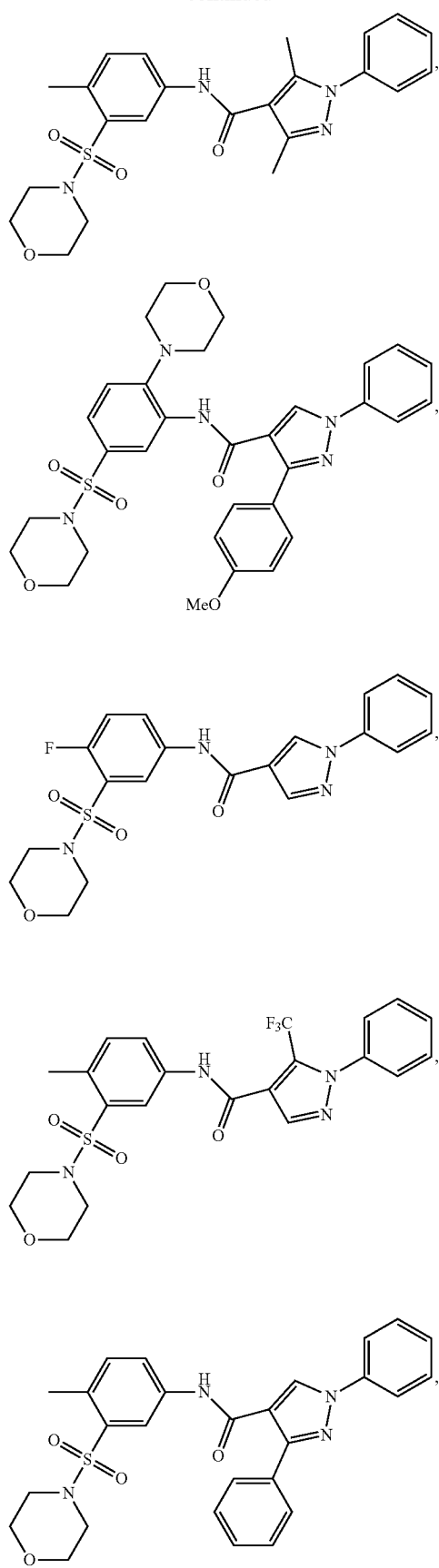

121
-continued
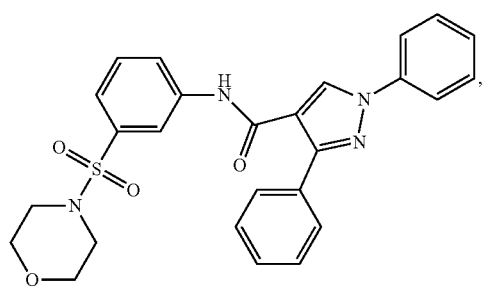
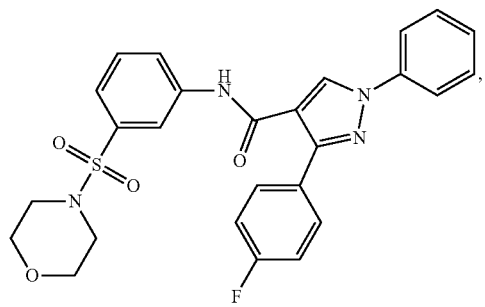
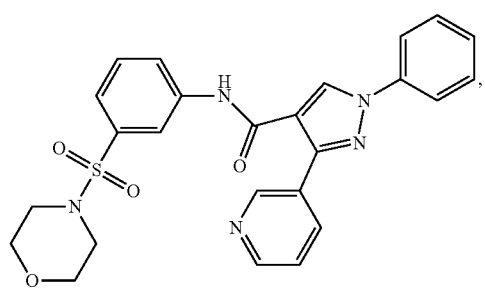
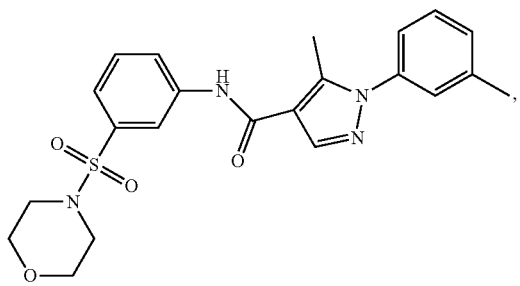
122
-continued
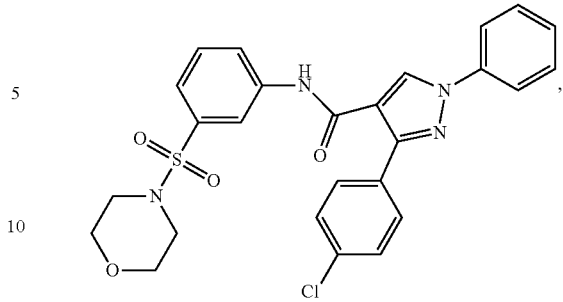
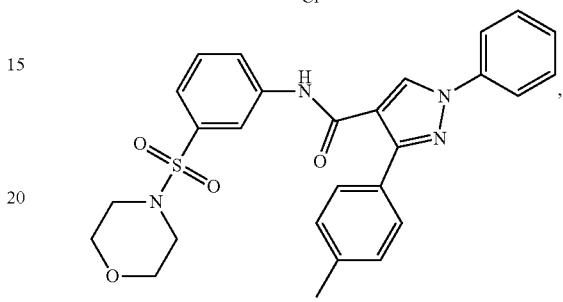
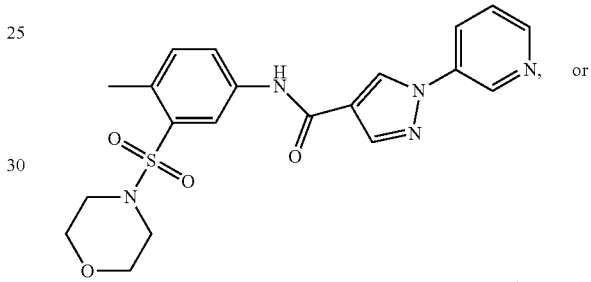, or
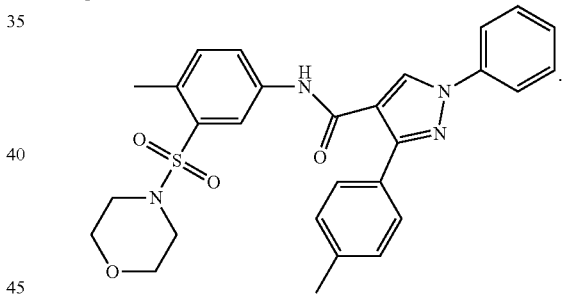.
* * * * *